US011697819B2

(12) United States Patent
Shoseyov et al.

(10) Patent No.: US 11,697,819 B2
(45) Date of Patent: Jul. 11, 2023

(54) COMPOSITIONS AND METHODS FOR PRODUCING POLYPEPTIDES WITH A MODIFIED GLYCOSYLATION PATTERN IN PLANT CELLS

(71) Applicant: Yissum Research Development Company of the Hebrew University of Jerusalem Ltd., Jerusalem (IL)

(72) Inventors: Oded Shoseyov, Karme Yosef (IL); Helena Magrisso, Rehovot (IL); Tzvi Zvirin, Holon (IL); Amit Yaari, Yizrael (IL); Zohar Katz, Modiin-Maccabim-Reut (IL)

(73) Assignee: Yissum Research Development Company of the Hebrew University of Jerusalem Ltd, Jerusalem (IL)

( * ) Notice: Subject to any disclaimer, the term of this patent is extended or adjusted under 35 U.S.C. 154(b) by 376 days.

(21) Appl. No.: 16/437,844

(22) Filed: Jun. 11, 2019

(65) Prior Publication Data

US 2019/0382781 A1  Dec. 19, 2019

Related U.S. Application Data

(63) Continuation of application No. 15/600,193, filed on May 19, 2017, which is a continuation of application No. PCT/IL2015/051112, filed on Nov. 19, 2015.

(60) Provisional application No. 62/082,204, filed on Nov. 20, 2014.

(51) Int. Cl.
| | |
|---|---|
| *C12N 15/82* | (2006.01) |
| *C12N 15/62* | (2006.01) |
| *C12P 21/00* | (2006.01) |
| *C07K 16/22* | (2006.01) |
| *C07K 16/24* | (2006.01) |
| *C12N 9/24* | (2006.01) |

(52) U.S. Cl.
CPC .......... *C12N 15/8258* (2013.01); *C07K 16/22* (2013.01); *C07K 16/241* (2013.01); *C12N 9/2402* (2013.01); *C12N 15/62* (2013.01); *C12N 15/625* (2013.01); *C12N 15/8205* (2013.01); *C12N 15/8218* (2013.01); *C12N 15/8257* (2013.01); *C12P 21/005* (2013.01); *C12Y 302/01037* (2013.01); *C12Y 302/01051* (2013.01); *C07K 2317/13* (2013.01); *C07K 2317/21* (2013.01); *C07K 2317/24* (2013.01); *C07K 2319/02* (2013.01); *C07K 2319/03* (2013.01); *C07K 2319/705* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dryer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzguris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,683,202 A | 7/1987 | Mullis |
| 4,801,531 A | 1/1989 | Frossard |
| 4,855,237 A | 8/1989 | Morinaga et al. |
| 4,879,219 A | 11/1989 | Wands et al. |
| 4,945,050 A | 7/1990 | Sanford et al. |
| 5,011,771 A | 4/1991 | Bellet et al. |
| 5,192,659 A | 3/1993 | Simons |
| 5,202,422 A | 4/1993 | Hiatt et al. |
| 5,272,057 A | 12/1993 | Smulson et al. |
| 5,281,521 A | 1/1994 | Trojanowski et al. |
| 5,316,931 A | 5/1994 | Donson et al. |
| 5,360,726 A | 11/1994 | Raikhel |
| 5,464,765 A | 11/1995 | Coffee et al. |
| 5,637,490 A | 6/1997 | Sano et al. |

(Continued)

FOREIGN PATENT DOCUMENTS

| | | |
|---|---|---|
| CN | 101484585 | 7/2009 |
| DE | 19900635 | 7/2000 |

(Continued)

OTHER PUBLICATIONS

Matsuo et al (J. Biosci. Bioeng., 2014, 118(4): 448-454) (Year: 2014).*
Chen et al (Medicinal Research Reviews, 2005, 25(3): 343-360) (Year: 2005).*
Hussack et al, J. Agric. Food Chem, 2010, 58, 3451-3459.*
Chen et al (2005) Modification of Plant N-glycans Processing: The Future of Producing Therapeutic Protein by Transgenic Plants, Medicinal Research Reviews, 25(3): 343-360.
Zeleny et al (2006) Molecular Cloning and Characterization of α1,3/4-fucosidase based on sequence tags from almond fucosidase 1, Phytochemistry 67, pp. 641-648.

(Continued)

*Primary Examiner* — Jason Deveau Rosen
(74) *Attorney, Agent, or Firm* — Scott H. Blackman; Booth Udall Fuller, PLC

(57) ABSTRACT

A method of modifying a glycosylation pattern of a polypeptide-of-interest in a plant or plant cell is provided. The method comprising expressing in a plant or plant cell transformed to express at least one glycosidase in a subcellular compartment, a nucleic acid sequence encoding the polypeptide-of-interest, such that the at least one glycosidase and the polypeptide-of-interest are co-localized to the subcellular compartment of the plant or plant cell, thereby modifying the glycosylation pattern of the polypeptide-of-interest in the plant or plant cell.

19 Claims, 18 Drawing Sheets

Specification includes a Sequence Listing.

(56) References Cited

U.S. PATENT DOCUMENTS

| | | | | |
|---|---|---|---|---|
| 5,670,623 | A * | 9/1997 | Shoseyov | A01N 25/10 |
| | | | | 530/350 |
| 5,693,507 | A | 12/1997 | Daniell et al. | |
| 5,889,174 | A | 3/1999 | Warren et al. | |
| 6,300,112 | B1 | 10/2001 | De Graaff et al. | |
| 6,331,416 | B1 | 12/2001 | Shani et al. | |
| 6,391,683 | B1 | 5/2002 | Chiu et al. | |
| 7,803,991 | B2 * | 9/2010 | Daniell | C12N 15/8214 |
| | | | | 800/278 |
| 9,506,079 | B2 * | 11/2016 | Mason | C12N 15/8257 |
| 2003/0159178 | A1 | 8/2003 | Ulskov et al. | |
| 2007/0089201 | A1 | 4/2007 | Briggs et al. | |
| 2008/0060092 | A1 | 3/2008 | Dickey et al. | |
| 2009/0203079 | A1 | 8/2009 | Sticklen et al. | |
| 2010/0227828 | A1 | 9/2010 | Gokaraju et al. | |
| 2012/0079627 | A1 | 3/2012 | Gampala et al. | |
| 2014/0090108 | A1 | 3/2014 | Garabagi et al. | |
| 2014/0120578 | A1 * | 5/2014 | Mathis | A01H 1/06 |
| | | | | 435/69.1 |
| 2014/0273235 | A1 * | 9/2014 | Voytas | C12N 9/16 |
| | | | | 435/469 |
| 2015/0176045 | A1 | 6/2015 | Marcel et al. | |

FOREIGN PATENT DOCUMENTS

| | | | |
|---|---|---|---|
| EP | 2090648 | 8/2009 | |
| WO | 8706261 | 10/1987 | |
| WO | 0077175 | 12/2000 | |
| WO | 01029242 | 4/2001 | |
| WO | 03078637 | 9/2003 | |
| WO | 2004074498 | 9/2004 | |
| WO | 2004074499 | 9/2004 | |
| WO | 2004091475 | 10/2004 | |
| WO | 2004096978 | 11/2004 | |
| WO | 2005080544 | 9/2005 | |
| WO | 2006035442 | 4/2006 | |
| WO | 2006040761 | 4/2006 | |
| WO | 2007130638 | 11/2007 | |
| WO | WO-2008056265 A2 * | 5/2008 | ......... C12N 15/8221 |
| WO | 2008128144 | 10/2008 | |
| WO | 2008135991 | 11/2008 | |
| WO | 2008151440 | 12/2008 | |
| WO | 2009069123 | 6/2009 | |
| WO | 2010015722 | 2/2010 | |
| WO | 2012122308 | 9/2012 | |
| WO | 2012170678 | 12/2012 | |
| WO | 2014078475 | 5/2014 | |
| WO | 2015095037 | 6/2015 | |

OTHER PUBLICATIONS

Mena, et al (1998) An endosperm-specific DOF protein from barley, highly conserved in wheat, binds to and activates transcription from the prolamin-box of a native B-hordein promoter in barley endosperm, The Plant Journal, 116 (1):53-62.

Rafalski, et al (1984) Developmentally regulated plant genes: the nucleotide sequence of a wheat gliadin genomic clone, The EMBO Journal, vol. 3, No. 6, pp. 1409-1415.

Mcente-Carbajosa, et al (1998) Barley BLZ1: a bZIP transcriptional activator that interacts with endosperm-specific gene promoters, Plant J. 13:629-640.

Wu, et al (1998) Promoters of Rice Seed Storage Protein Genes Direct Endosperm-Specific Gene Expression in Transgenic Rice, Plant Cell Physiology 39(8):885-889.

Sato, et al (1996) A rice homeobox gene, OSH1, is expressed before organ differentiation in a specific region during early embryogenesis, Proc. Nat. Acad. Sci. USA 93:8117-8122.

Nakase, et al (1997) Characterization of a novel rice bZIP protein which binds to the a-globulin promoter, Plant Mol. Biol. 33:513-522.

Opsahl-Ferstad, et al (1997) ZmEsr, a novel endosperm-specific gene expressed in a restricted region around the maize embryo, Plant J. 12:235-46.

DeRose, et al (1996) Analysis of kafirin promoter activity in transgenic tobacco seeds, PMB 32:1029-35.

Postma-Haarsma, et al (1999) Characterization of the KNOX class homeobox genes Oskn2 and Oskn3 identified in a collection of cDNA libraries covering the early stages of rice embryogenesis, Plant Mol. Biol. 39:257-71.

Wu, et al (1998) Genomic Cloning of 18kDa Oleosin and Detection of Triacylglycerols and Oleosin Isoforms in Maturing Rice and Postgerminative Seedlings, J. Biochem., 123:386.

Albani, et al (1997) The Wheat Transcriptional Activator SPA: A Seed-Specific bZIP Protein that Recognizes the GCN4-like Motif in the Bifactorial Endosperm Box of Prolamin Genes, Plant Cell, 9:171184.

Cummins, et al (1992) cDNA sequence of a sunflower oleosin and transcript tissue specificity, Plant Mol. Biol. 19:873-876.

Van der Meer, et al, Promoter analysis of the chaicone synthase (chsA) gene of Petunia hybrida: a 67 bp promoter region directs flower-specific expression, Plant Mol. Biol. 15, 95-109.

Twell, et al (1989) Isolation and expression of an anther-specific gene from tomato, Mol. Gen Genet. 217:240-245.

Potrykus, I (1991) Gene Transfer to Plants: Assessment of Published Approaches and Results, Annu. Rev. Plant. Physiol., Plant. Mol. Biol. 42:205-225.

Shimamoto, et al (1989) Fertile transgenic rice plants regenerated from transformed protoplast, Nature 338:274-276.

Klee, et al (1987) Agrobacterium-mediated Plant Transformation and its Further Applications to Plant Biology, Annu. Rev. Plant Physiol. 38:467-486.

Zhang, et al (1988) Transgenic rice plants produced by electroporation-mediated plasmid uptake into protoplasts, Plant Cell Rep. 7:379-384.

Fromm, et al (1986) Stable transformation of maize after gene transfer by electroporation, Nature, 319:791-793.

Sanford, John C (1990) Biolistic plant transformation, Physiologia Plant. 79:206-209.

Neuhaus, et al (1987) Transgenic rapeseed plants obtained by the microinjection of DNA into microspore-derived embryoids, Theor. Appl. Genet. 75:30-36.

Neuhaus and Spangenberg (1990) Plant transformation by microinjection techniques, Physiol. Plant. 79:213-217.

Ohta, Yasuo (1986) High-efficiency genetic transformation of maize by a mixture of pollen and exogenous DNA, Proc. Natl. Acad. Sci. USA 83:715-719.

Dawson, et al (1989) A Tobacco Mosaic Virus-Hybrid Expresses and Loses an Added Gene, Virology, 172:285-292.

Takamatsu, et al (1987) Expression of bacterial chloramphenicol acetyltransferase gene in tobacco plants mediated by TMV-RNA, EMBO J. 6:307-311.

Takamatsu, et al (1990) Production of enkephalin in tobacco protoplasts using tobacco mosaic virus RNA vector, FEBS Letters 269:73-76.

Poehlman, John Milton (1959) Breeding Field Crops, Henry Holt and Company, New York.

Bradford, M. (1976) A Rapid and Sensitive Method for the Quantitation of Microgram Quantities of Protein Utilizing the Principle of Protein-Dye Binding, Anal. Biochem. 72:248-254.

Coughlan, et al (1988) Further Enzymatic Characteristics of a Thylakoid Protein Kinase, J. Biol. Chem. 263:16631-16636.

Freer, Shelby N. (1993) Kinetic Characterization of a B-Glucosidase from a Yeast Candida wickerhamii, J. Biol. Chem. 268:9337-9342.

Sambrook, et al (1989) Molecular Cloning: a laboratory manual (abstract).

Li, et al (2008) A Distinct Endosomal Ca21/Mn21 Pump Affects Root Growth through the Secretory Process1[C][W][OA], Plant Physiol. 147:1675-1689.

Bardor, et al (2003) Immunoreactivity in mammals of two typical plant glyco-epitopes, core a(1,3)-fucose and core xylose, Cclycobiology, 13:427-434.

Svab, et al (1993) High-frequency plastid transformation in tobacco by selection for a chimeric aadA gene, Proc Natl Acad Sci, 90(3):913-917.

Wei, et al (2004) Manipulating volatile emission in tobacco leaves by expressing Aspergillus niger β-glucosidase in different subcellular compartments, Plant Biotechnol. 2:341-350.

(56) References Cited

OTHER PUBLICATIONS

Wilson Iain BH (2002) Glycosylation of proteins in plants and invertebrates, Curr. Opin. Struct. Biol. 12:569-577.
Scofield, et al (1987) Nucleotide Sequence of a Member of the Napin Storage Protein Family from *Brassica napus*, The Journal of Biological Chemistry, vol. 262, No. 25, pp. 12002-12008.
Brandizzi, et al (2002) The Destination for Single-Pass Membrane Proteins Is Influenced Markedly by the Length of the Hydrophobic Domain, The Plant Cell, vol. 14, No. 5 1077-1092.
Sardana, et al (1996) Construction and rapid testing of synthetic and modified toxin gene sequences CryIA (b & c) by expression in maize endosperm culture, Plant Cell Reports 15:677-681.
Wildt, et al (2005), The Humanization of N-Glycosylation Pathways in Yeast, Nature Review, Microbiology, vol. 3, No. 2, 119-128.
Hamilton, et al (2007), Glycosylation engineering in yeast: the advent of fully humanized yeast, Current Opinions in Biotechnology, vol. 18, No. 5: 387-392.
Hussack, et al (2010), Purification of Plant-Derived Antibodies Through Direct Immobilization of Affinity Ligands on Cellulose, J. Agric. Food Chem., vol. 58: 3451-3459.
Oh, Doo-Byoung et al., "Glycoengineering of the methylotrophic yeast *Hansenula polymorpha* for the production of glycoproteins with trimannosyl cor N-glycan by blocking core oligosaccharide assembly", Biotechnology Journal, 3:659-668 (2008).
Gor0batiuk, et al., (2012) Bioaffinity sorbent based on immobilized protein A *Staphylococcus aureus*: development and application, Biopolimery I Kletka, vol. 28, No. 2, pp. 141-148.
De Marchis, et al., (2011) Human [alpha]-mannosidase produced in transgenic tobacco plants is processed in human [alpha]-mannosidosis cell lines, Plant Biotechnology Journal, vol. 9, No. 9, pp. 1061-1073.
Gomord, et al (2010) Plant-specific glycosylation patterns in the context of therapeutic protein production, Plant Biotechnology Journal, vol. 8, No. 5, pp. 564-587.
Balen, et al (2007) N-glycosylation of recombinant therapeutic glycoproteins in plant systems, Food Technology and Biotechnology, vol. 45, No. 1, pp. 1-10.
Meuris, et al (2014) GlycoDelete engineering of mammalian cells simplifies N-glycosylation of recombinant proteins, Nature Biotechnology, vol. 32, No. 5, pp. 485-489.
Piron, et al (2015) Using GlycoDelete to produce proteins lacking plant-specific N-glycan modification in seeds, Nature Biotechnology, vol. 33, No. 11, pp. 1135-1137.
Kornfeld, et al (1985) Assembly of Asparagine-linked oligosaccharides, Ann. Rev. Biochem. 54:631-664.
Yamane-Ohnuki et al. (2009) Production of therapeutic antibodies with controlled focusylation, MABs, May-Jun. 1(3), pp. 230-236.
Strasser, et al, (2008) Generation of glyco-engineered Nicotiana benthamiana for the production of monoclonal antibodies with a homogeneous human-like N-glycan structure, Plant Biotechnology Journal, 6, pp. 392-402.
Matsuo, et al, (2014) Deletion of plant-specific sugar residues in plant N-glycans by repression of GDP-D-mannose 4,6-dehydratase and B-1,2-xylosyltransferase genes, Journal of Bioscience and Bioengineering, 118, 4, pp. 448-454.
Matsuo, et al (2011), Deletion of fucose residues in plant N-glycans by repression of the GDP-mannose 4, 6-dehydratase gene using virus-induced gene silencing and RNA interference, Plant Biotechnology Journal, 9: 264-281.
Becker, et al (1992), New plant binary vectors with selectable markers located proximal to the left T-DNA border, Plant Mol. Biol 20:49.
Close, P.S. (1993) Cloning and molecular characterization of two nuclear genes for *Zea mays* mitochondrial ehaperonin 60, Master's Thesis, Iowa State University.
Knox, et al (1987) Structure and Organization of Two Divergent Alpha-Amylase Genes from Barley, Plant Mol. Biol. 9:3-17.
Lerner, et al (1987) Cloning and characterization of Root-Specific Barley Lectin, Plant Physiol. 91:124-129.

Fontes, et al (1991) Characterization of an Immunoglobulin Binding Protein Homolog in the Maize floury-2 Endosperm Mutant, Plant Cell 3:483-496.
Matsuoka, et al (1991) Propeptide of a precursor to a plant vacuolar protein required for vacuolar targeting, Proc. Natl. Acad. Sc. 88:834-838.
Gould, et al (1989) A Conserved Tripeptide Sorts Proteins to Peroxisomes, J. Cell. Biol. 108:1657-1664.
Creissen, et al (1991) Molecular characterization of glutathione reductase cDNAs from pea (*Pisum Sativum* L.), Plant J. 2:129-131.
Kalderon, et at (1984) A short amino acid sequence able to specify nuclear location, Cell 39:499-509.
Stiefel, et al (1990) Expression of a maize cell wall hydroxyproline-rich glycoprotein gene in early leaf and root vascular differentiation, Plant Cell 2:785-793.
Kogan, et al (2001) Self-Assembly of the Amphipathic Helix (VHLPPP): A Mechanism for Zein Protein Body Formation, J. Mol. Biol. 312:907-913.
Torrent, et al (2009), Eukaryotic protein production in designed storage organelles, BMC Biology 7, 5.
Mainieri, et al (2004) Zeolin. A new Rcombinant Storage Protein Constructed Using Maize γ-Zein and Bean Phaseolin, Plant Physiol. 136:3447-3456.
Rogers, J.C. (1985) Two barley alpha-amylase gene families are regulated differently in aleurone cells, J Biol. Chem. V. 260, No. 6, pp. 3731-3738.
Holwerda, et al (1992) Proaleurain Vacuolar Targeting is Mediated by Short Contiguous Peptide Interactions, The Plant Cell, 4:307-318.
Nakamura, et al (1993) Protein Targeting to the Vacuole in Plant Cells, Plant Physiol., 101: 1-5.
Saalbach, et al (1991) Different Legumin Protein Domains Act as Vacuolar Targeting Signals, The Plant Cell, 3:695-708.
Shinshi, et al (1990) Structure of a Tobacco endochitinase gene: evidence that different chitinase genes can arise by transportation of sequences encoding a cysteine-rich domain, Plant Molec. Biol. 14:357-368.
Wei, et al (2004) Fluorescent Screening of Transgenic Arabidopsis Seeds without Germination, Plant Biotechnol. J. 135(2): 709-714.
McElroy, et al (1990) Isolation of an Efficient Actin Promoter for Use in Rice Transformation, The Plant Cell, 2:163-171.
Odell, et al. (1985) Identification of DNA sequences required for activity of the cauliflower mosaic virus 35S promoter, Nature, 313:81-812.
Nilsson, et al (1997) The Agrobactirium rhizogenes rolB and rolC promoters are expressed in pericycle cells competent to serve as root initials in transgenic hyprid aspen, Physiol. Plant 100:456-462.
De Pater, et al (1992) The promoter of the rice gene GOS2 is active in various different monocot tissues and binds rice nuclear factor ASF-1, Plant J. Nov; 2(6):837-844.
Christensen, et al (1992) Maize polybiquitin genes: structure, thermal pertubation of expression and transcript splicing and promoter activity following transfer to protoplasts by electroporation, Plant Mol. Biol. 18:675-678.
Buchholz, et al (1994) Cyclophilins are encoded by a small gene family in rice, Plant Mol. Biol. 25(5):837-843.
Lepetit, et al (1992) A plant histone gene promoter can direct both replication-dependent, and independent gene expression in transgenic plants, Gen. Genet. 231:276-285.
An, et al (1996) Strong, constitutive expression of the Arabidopsis ACT2/ACT8 actin subclass in vegetative tissues, Plant J. 10(1):107-121.
Simon, et al (1985) Nucleotide sequence of a cDNA clone of *Brassica napus* 12S storage protein shows homology with legumin from Pisum sativum, Plant Mol. Biol. 5. 191.
Baszczynski, et al (1990) Isolation and nueleotide sequence of a genolnie clone encoding a new *Brassica napus* napin gene, Plant Mol. Biol. 14:633.
Altenbach et al (1992) Accumulation of a Brazil nut albumin in seeds of transgenic canola, Plant Mol. Biol. 18:235-245.
Ellis, et al (1988) Tissue-specific expression of a pea legumin gene in seeds of Nicotiana, Plant Mol. Biol. 18:203-214.

(56) References Cited

OTHER PUBLICATIONS

Takaiwa, et al (1987) A rice glutelin gene family—A major type of glutelin mRNAs can be divided into two classes, Mol. Gen. Genet. 208: 15-22.
Takaiwa, et al (1987) Nucleotide sequence of a rice glutelin gene, FEES Letts. 221: 43-47.
Matzke, et al (1990) Deletion analysis of a zein gene promoter in transgenic tobacco plants, Plant Mol. Biol, 143:323-332.
Stalberg, et al (1996) Disruption of an overlapping E-box/ABRE motif abolished high transcription of the napA storage-protein promoter in transgenic *Brassica napus* seeds, Planta 199, pp. 515-519.
Colot, et al (1989) Molecular characterization of an active wheat LMW glutenin gene and its relation to other wheat and barley prolamin genes, Mol. Gen. Genet. 216:81-90.
Cho, et al (1999) Inheritance of tissue-specific expression of barley hordein promoter-uidA fusions in transgenic barley plants, 98:1253-62.
Muller, et al (1993) The nitrogen response of a barley C-hordein promoter is controlled by positive and negative regulation of the GCN4 and endosperm box. Plant J. 4:343-55.
Sorensen, et al (1996) Hordein promoter methylation and transcriptional activity in wild-type and mutant barley endosperm, 250:750-760.
Pogorelko et al (2011) Post-synthetic modification of plant cell walls by expression of microbial hydrolases in the apoplast, Plant Mol. Biol.; 77:433-445.
Summers et al (2016) The structure of glycoside hydrolase 29 family member from a rumen bacterium reveals unique, dual carbohydrate-binding domains, Acta Crystal log rafic Section F Struct Biology Comm, 72 (Pt.10):750-761.

\* cited by examiner

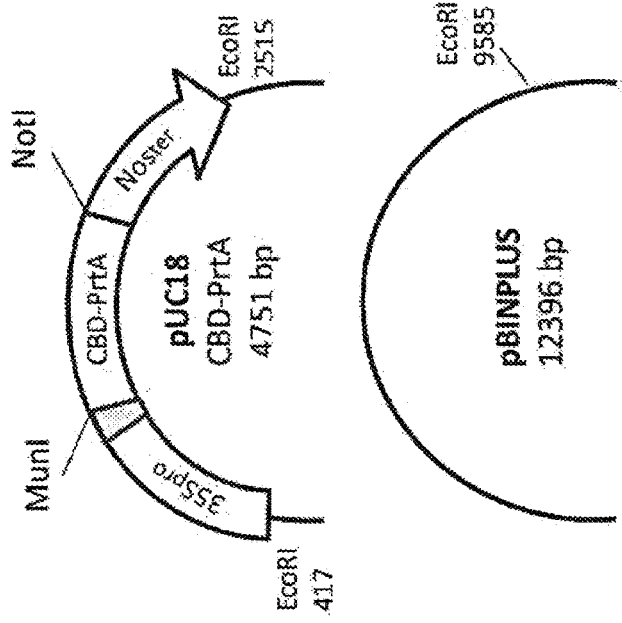
FIG. 5A
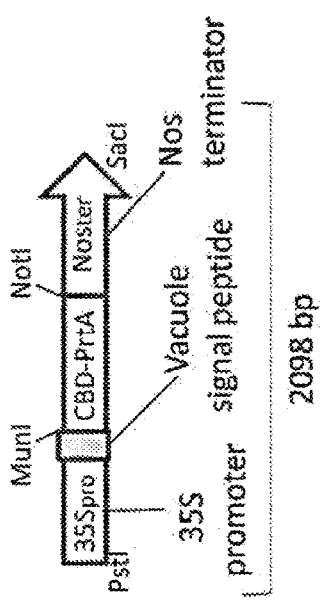
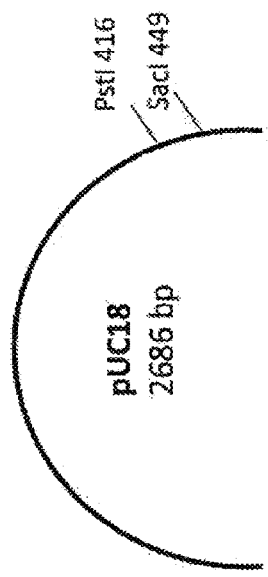
FIG. 5B
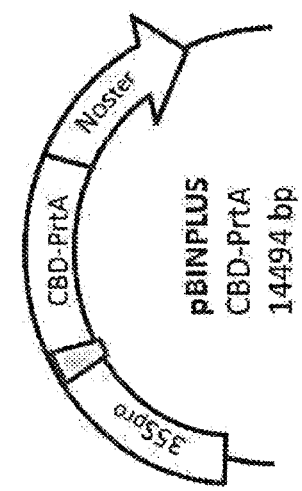
FIG. 5C

FIG. 12A
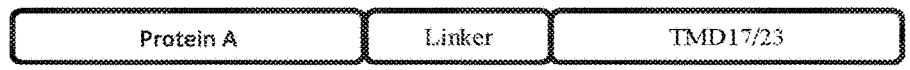
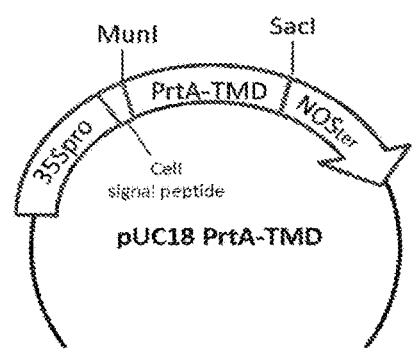
FIG. 12B
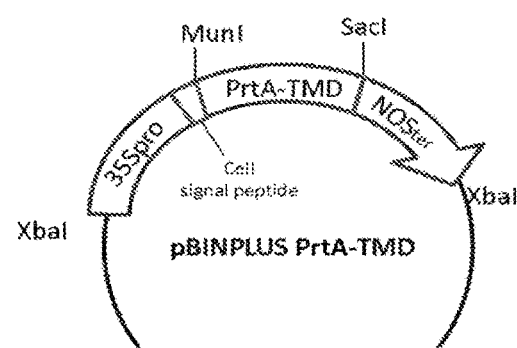
FIG. 12C

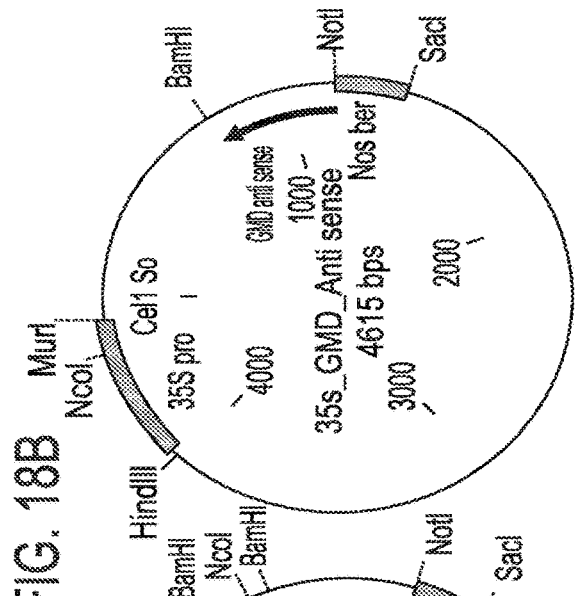
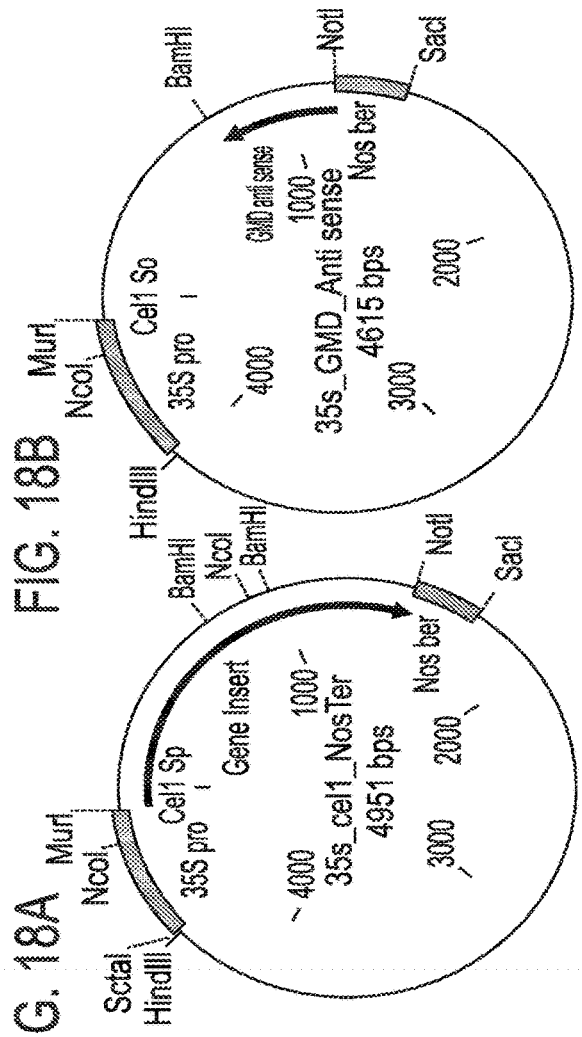
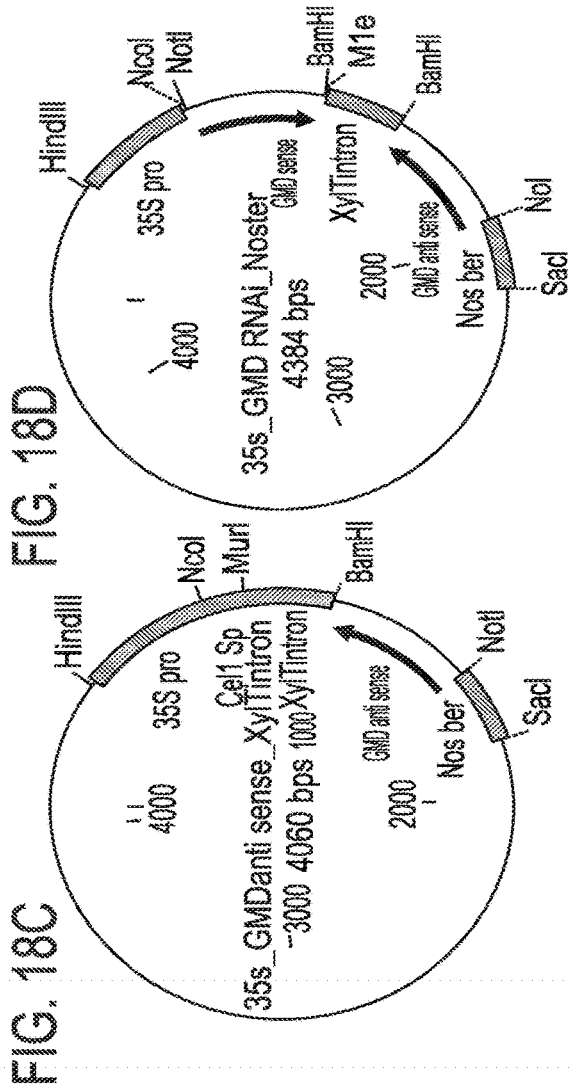

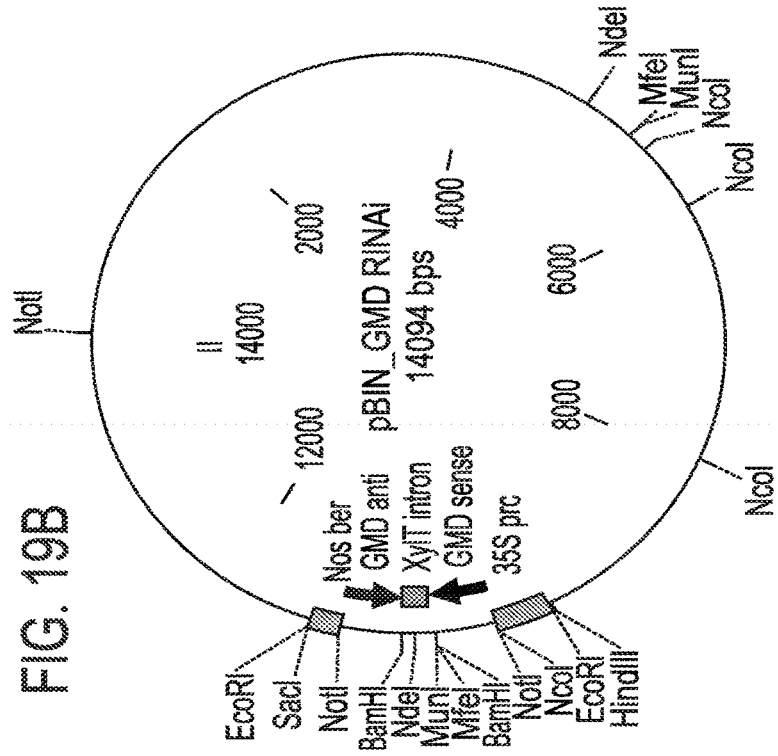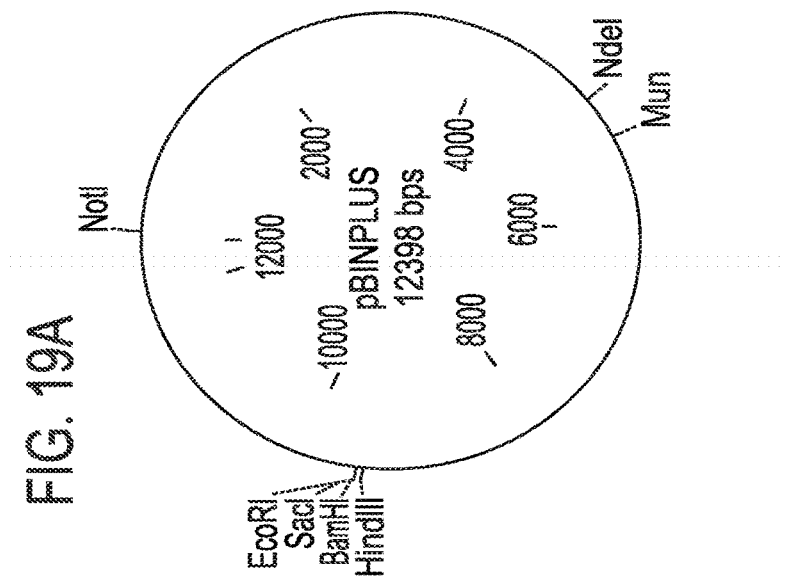

SEQUENCE LISTING

<160> NUMBER OF SEQ ID NOS: 45

<210> SEQ ID NO 1
<211> LENGTH: 1356
<212> TYPE: DNA
<213> ORGANISM: Artificial sequence
<220> FEATURE:
<223> OTHER INFORMATION: Humira heavy chain nucleotide sequence

<400> SEQUENCE: 1

```
gaggttcagt tggtggagtc aggtggaggt cttgttcagc caggtagatc cttgaggttg      60
agttgtgcag catcaggttt tactttgat gattatgcta tgcattgggt gagacaagca     120
ccaggaaagg gtcttgagtg ggtttcagct atcacttgga atagtggaca cattgattat    180
gcagattctg ttgaaggaag gtttactatt tcaagggata acgctaagaa cagtctctat    240
cttcagatga actctcttag ggctgaggat actgctgttt actactgtgc taaagtttca    300
tatcttagta cagcatcttc actcgattac tggggacagg gtactcttgt gacagttagt    360
tccgcttcca ctaagggacc ttctgttttc ccattggcac cttcttcaaa atcaactagt    420
ggaggtacag ctgcacttgg ttgcttggtt aaagattatt tccagaacc tgtgacagtt    480 tcctggaact ctggtgctct tacttctggt gtgcatacat cccagcagt tttgcaaagt    540 tccggattat attcactctc ttcagttgtg actgtgccta gttcctcttt gggtactcag    600
acatatattt gtaacgttaa ccataagcca agtaacacaa aagtggataa gaaagttgag    660
cctaagtctt gcgataaaac tcacacatgt ccaccttgcc cagctcctga acttttggga    720
ggtccatcag ttttttcttt cccacctaag cctaaagata ctctcatgat ctcaagaact    780
ccagaggtga catgtgttgt ggttgatgtt agtcatgaag atcctgaggt gaagtttaat    840
tggtatgttg atggagtgga agttcacaac gctaagacaa aaccaagaga gagcaatat    900 aattccactt acagggtggt ttctgtgctt acagttttgc accaggattg gctcaatggt    960
aaagagtaca gtgtaaagt ttctaacaag gctcttccag cacctattga aaagactatc   1020
tcaaaggcta aggtcaacc aagagagcct caggtttata cacttccacc ttctagggat   1080
gaattgacta gaaccaagt gtcattaaca tgcctcgtta aaggatttta cccaagtgat   1140
atagcagttg aatgggagtc caacggtcag cctgaaaata actataagac tacaccacct   1200
gttcttgatt cagatggatc tttctttctt tactctaagt tgactgttga taagtcaagg   1260
tggcaacagg gtaatgtgtt ctcctgctct gttatgcacg aggctctcca caatcactac   1320
actcaaaaat cccttcatt atctccaggt aaataa                              1356
```

<210> SEQ ID NO 2
<211> LENGTH: 451
<212> TYPE: PRT
<213> ORGANISM: Artificial sequence
<220> FEATURE:
<223> OTHER INFORMATION: Humira heavy chain protein sequence

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Val Ser Tyr Leu Ser Thr Ala Ser Ser Leu Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val

```
                    405                 410                 415
Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro Gly Lys
        450

<210> SEQ ID NO 3
<211> LENGTH: 645
<212> TYPE: DNA
<213> ORGANISM: Artificial sequence
<220> FEATURE:
<223> OTHER INFORMATION: Humira light chain nucleotide sequence

<400> SEQUENCE: 3
gatattcaaa tgacacagag tccatcctcc ttgagtgctt cagtgggaga tagagttact      60
attacttgca gggcttctca gggtattaga aattatcttg cttggtacca acagaagcct     120
ggtaaagcac ctaaactttt gatctatgct gcatcaactt tgcaaagtgg agttccatcc     180
aggttttctg gatcaggtag tggaacagat ttcactctca aatctcttc actccaacca     240 gaagatgttg ctacttatta ctgtcagaga tataacaggg ccttacac ttttggtcaa      300 ggaacaaaag tggaaattaa gaaacagtt gctgcaccat ctgtgtttat attcccacct     360
tcagatgagc agcttaaatc aggtactgct agtgttgtgt gcttactcaa taacttctat     420
cctagggaag ctaaagttca gtggaaggtg gataatgcat acaatccgg aaactctcag     480 gaatcagtta ctgagcagga tagtaaagat tccacatact ctcttagttc cactcttaca     540
ttgtctaagg ctgattatga aagcataaa gtgtacgcat gtgaggtgac acatcaggga     600
ttatcaagtc cagtgacaaa gagtttcaat agaggagaat gctga                    645

<210> SEQ ID NO 4
<211> LENGTH: 214
<212> TYPE: PRT
<213> ORGANISM: Artificial sequence
<220> FEATURE:
<223> OTHER INFORMATION: Humira light chain protein sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 5
<211> LENGTH: 1362
<212> TYPE: DNA
<213> ORGANISM: Artificial sequence
<220> FEATURE:
<223> OTHER INFORMATION: Avastin heavy chain nucleotide sequence

<400> SEQUENCE: 5

```
gaagttcagt tagtggaaag tggtggagga ttagttcagc caggtggtag tttgaggtta      60
agttgtgcag catcaggtta tacatttact aattatggta tgaattgggt gagacaagct     120
ccaggaaagg gtttggaatg ggttggatgg ataaatactt atacaggaga gcctacttat     180
gctgctgatt ttaagagaag gtttacattc tcacttgata cttcaaaaag tacagcttat     240
cttcagatga actctttgag ggctgaagat actgctgttt actactgtgc aaagtaccca     300
cattactacg gttcttcaca ctggtacttt gatgtttggg gacagggtac tcttgtgaca     360
gttagttccg cttccacaaa gggaccttct gttttcccac ttgcaccttc ttcaaaatcc     420
acttctggag gtacagctgc attaggttgc ctcgttaagg attattttcc agagcctgtg     480
actgtttcct ggaactctgg tgctcttact tcaggtgtgc atacattccc agcagttttg     540
caaagttccg gactttattc tttgtcttca gttgtgactg tgcctagttc ctctcttggt     600
actcagacat acatctgtaa tgttaaccat aagccatcta acacaaaagt ggataagaaa     660
gttgaaccta gtcatgcga taaaactcac acatgtccac cttgcccagc tcctgagctt     720
ttgggaggtc catcagtttt tctttttccca cctaagccta agatacact catgattagt     780 agaactccag aagtgacatg tgttgtggtt gatgtttctc atgaagatcc tgaggtgaag     840
tttaattggt atgttgatgg agtggaggtt cacaacgcta agactaaacc aagagaagag     900
caatataatt caacttacag ggtggttagt gtgttaacag ttctccacca ggattggctc     960
aatggtaaag aatacaagtg taaagtttca aacaaggctt gccagcacc tattgaaaag    1020 actatctcta aggctaaagg tcaaccaaga gagcctcagg tttatacact tccaccttcc    1080
agggaagaga tgactaagaa tcaagtgagt cttacatgct tggttaaagg attttaccca    1140
tcagatattg cagttgaatg ggagagtaac ggtcagcctg aaataacta taagactaca    1200 ccacctgtgt tggattcaga tggatctttc tttctttact ccaagctcac tgttgataaa    1260
tctaggtggc aacagggtaa tgtgttctca tgcagtgtta tgcacgaggc actccataat    1320
cactacactc agaaatctct ctctctctcc ccaggtaaat aa                        1362
```

<210> SEQ ID NO 6
<211> LENGTH: 453
<212> TYPE: PRT
<213> ORGANISM: Artificial sequence
<220> FEATURE:
<223> OTHER INFORMATION: Avastin heavy chain protein sequence

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
        100                 105                 110

Trp Gly Gln Gly Thr Leu Val Thr Val Ser Ser Ala Ser Thr Lys Gly
    115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Glu Glu Met Thr Lys Asn Gln
    355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

```
                    405                 410                 415
Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 7
<211> LENGTH: 645
<212> TYPE: DNA
<213> ORGANISM: Artificial sequence
<220> FEATURE:
<223> OTHER INFORMATION: Avastin light chain nucleotide sequence

<400> SEQUENCE: 7
gatattcaga tgacacagtc ccctagttcc ctcagtgctt ccgttggaga tagagttact      60
attacttgtt ccgcttccca ggatatttca aattatctta attggtacca acagaagcct    120
ggtaaagctc ctaaggttct catctatttc acttcttcac tccattccgg agtgccatct    180
agattttctg gatccggttc tggaactgat tcactctta caataagttc cttgcaacca     240
gaagattttg caacatatta ctgtcaacag tactctactg ttccttggac attcggtcag    300
ggaactaaag tggaaattaa gagaacagtt gctgcaccat ccgtgtttat attcccacct    360
agtgatgagc aacttaaatc aggtacagct agtgttgtgt gccttttgaa taacttctat    420
cctagggaag ctaaagttca gtggaaggtg ataatgcac ttcaatcagg aaacagtcag     480
gaatccgtta ctgagcagga ttctaaggat tcaacataca gtttgtcttc aactttaaca    540
ctctcaaagg ctgattatga aagcacaaa gtttacgcat gtgaggttac acatcagggt     600
ttatcatcac cagttactaa gtccttcaac aggggagagt gctag                    645

<210> SEQ ID NO 8
<211> LENGTH: 214
<212> TYPE: PRT
<213> ORGANISM: Artificial sequence
<220> FEATURE:
<223> OTHER INFORMATION: Avastin light chain protein sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 1335
<212> TYPE: DNA
<213> ORGANISM: Artificial sequence
<220> FEATURE:
<223> OTHER INFORMATION: CBD-PrtA nucleotide sequence

<400> SEQUENCE: 9

| | | |
|---|---|---|
| aatcttaagg tggaatttta caactccaac ccatctgata ctacaaattc cataaaccct | 60 |
| caattcaagg ttactaatac aggatcttca gctatcgatc tttcaaaact cactcttaga | 120 |
| tactactaca cagtggatgg tcaaaaggat cagacttttt ggtgtgatca tgctgcaatt | 180 |
| ataggatcaa atggtagtta caacggaata acttcaaacg ttaagggtac attcgtgaaa | 240 |
| atgagttcct ctactaataa cgctgataca tatctcgaaa tttcttttac tggaggtaca | 300 |
| cttgagccag gtgctcatgt tcaaatacag gaaggttcg caaaaaatga ttggtcaaac | 360 |
| tacactcaat ccaacgatta ctcttttaag tcagctagtc aattcgttga atgggatcag | 420 |
| gtgacagcat atttgaatgg tgttttagtg tggggtaaag agcctggagg ttcagttgtg | 480 |
| ccaagtactc aacctgttac tacaccacct gctactacaa agccacctgc aactacaatc | 540 |
| ccacctacta tggaacaaag aataacattg aaggaggctt gggatcaaag gaatggtttt | 600 |
| attcagtctt taaggatga tccatcccaa tctgctaatg tgctcggtga agcacaaaaa | 660 |
| cttaacgata gtcaggctcc taaagctgat gcacaacaaa ataactttaa taaggatcaa | 720 |
| cagtctgctt tctacgaaat cctcaatatg ccaaatctta acgaggcaca agaaatggt | 780 |
| tttattcagt cattgaagga tgatccttca caagtacaa acgttttggg tgaagctaag | 840 |
| aaattaaacg agagtcaggc tccaaaggca gataataact tcaataagga acaacagaac | 900 |
| gcattctacg agatcttgaa catgccaaat cttaacgaag agcagcgtaa tggttttatt | 960 |
| cagtcattga agatgatcc ttcccaatct gctaatcttt tgtccgaagc aaagaaactt | 1020 |
| aacgagtctc aggctcctaa ggcagataat aagttaaca aagaacaaca gaatgctttc | 1080 |
| tacgagcatc tccctaatct taacgaagaa caaaggaacg gtttcattca gtctttgaaa | 1140 |
| gatgatccat ctcaaagtgc aaatcttctc gctgaggcaa agaaacttaa cgatgctcag | 1200 |
| gcaccaaagg ctgacaataa gtttaacaaa gagcagcaaa acgcattcta cgagatattg | 1260 |
| cacttaccta acctcactga gagcagagg aatggtttta tccagagtct caaagatgat | 1320 |
| ccaggtaata gttaa | 1335 |

<210> SEQ ID NO 10
<211> LENGTH: 494
<212> TYPE: PRT
<213> ORGANISM: Artificial sequence
<220> FEATURE:
<223> OTHER INFORMATION: CBD-PrtA protein sequence

<400> SEQUENCE: 10

```
Met Met Ala His Ala Arg Val Leu Leu Ala Leu Ala Val Leu Ala
1               5                   10                  15

Thr Ala Ala Val Ala Val Ala Ser Ser Ser Ser Phe Ala Asp Ser Asn
                20                  25                  30

Pro Ile Arg Pro Val Thr Asp Arg Ala Ala Ser Thr Leu Ala Gln Leu
            35                  40                  45

Gln Leu Asn Leu Lys Val Glu Phe Tyr Asn Ser Asn Pro Ser Asp Thr
    50                  55                  60

Thr Asn Ser Ile Asn Pro Gln Phe Lys Val Thr Asn Thr Gly Ser Ser
65                  70                  75                  80

Ala Ile Asp Leu Ser Lys Leu Thr Leu Arg Tyr Tyr Tyr Thr Val Asp
                85                  90                  95

Gly Gln Lys Asp Gln Thr Phe Trp Cys Asp His Ala Ala Ile Ile Gly
            100                 105                 110

Ser Asn Gly Ser Tyr Asn Gly Ile Thr Ser Asn Val Lys Gly Thr Phe
    115                 120                 125

Val Lys Met Ser Ser Ser Thr Asn Asn Ala Asp Thr Tyr Leu Glu Ile
130                 135                 140

Ser Phe Thr Gly Gly Thr Leu Glu Pro Gly Ala His Val Gln Ile Gln
145                 150                 155                 160

Gly Arg Phe Ala Lys Asn Asp Trp Ser Asn Tyr Thr Gln Ser Asn Asp
            165                 170                 175

Tyr Ser Phe Lys Ser Ala Ser Gln Phe Val Glu Trp Asp Gln Val Thr
    180                 185                 190

Ala Tyr Leu Asn Gly Val Leu Val Trp Gly Lys Glu Pro Gly Gly Ser
    195                 200                 205

Val Val Pro Ser Thr Gln Pro Val Thr Thr Pro Ala Thr Thr Lys
210                 215                 220

Pro Pro Ala Thr Thr Ile Pro Pro Thr Met Glu Gln Arg Ile Thr Leu
225                 230                 235                 240

Lys Glu Ala Trp Asp Gln Arg Asn Gly Phe Ile Gln Ser Leu Lys Asp
            245                 250                 255

Asp Pro Ser Gln Ser Ala Asn Val Leu Gly Glu Ala Gln Lys Leu Asn
    260                 265                 270

Asp Ser Gln Ala Pro Lys Ala Asp Ala Gln Asn Asn Phe Asn Lys
    275                 280                 285

Asp Gln Gln Ser Ala Phe Tyr Glu Ile Leu Asn Met Pro Asn Leu Asn
290                 295                 300

Glu Ala Gln Arg Asn Gly Phe Ile Gln Ser Leu Lys Asp Asp Pro Ser
305                 310                 315                 320

Gln Ser Thr Asn Val Leu Gly Glu Ala Lys Lys Leu Asn Glu Ser Gln
            325                 330                 335

Ala Pro Lys Ala Asp Asn Asn Phe Asn Lys Glu Gln Gln Asn Ala Phe
    340                 345                 350

Tyr Glu Ile Leu Asn Met Pro Asn Leu Asn Glu Glu Gln Arg Asn Gly
    355                 360                 365

Phe Ile Gln Ser Leu Lys Asp Asp Pro Ser Gln Ser Ala Asn Leu Leu
    370                 375                 380

Ser Glu Ala Lys Lys Leu Asn Glu Ser Gln Ala Pro Lys Ala Asp Asn
385                 390                 395                 400

Lys Phe Asn Lys Glu Gln Gln Asn Ala Phe Tyr Glu His Leu Pro Asn
```

|     | 405 |     |     |     | 410 |     |     |     | 415 |     |     |
| --- | --- | --- | --- | --- | --- | --- | --- | --- | --- | --- | --- |

Leu Asn Glu Glu Gln Arg Asn Gly Phe Ile Gln Ser Leu Lys Asp Asp
    420       425       430

Pro Ser Gln Ser Ala Asn Leu Leu Ala Glu Ala Lys Lys Leu Asn Asp
   435       440       445

Ala Gln Ala Pro Lys Ala Asp Asn Lys Phe Asn Lys Glu Gln Gln Asn
450       455       460

Ala Phe Tyr Glu Ile Leu His Leu Pro Asn Leu Thr Glu Glu Gln Arg
465      470       475       480

Asn Gly Phe Ile Gln Ser Leu Lys Asp Asp Pro Gly Asn Ser
      485       490

<210> SEQ ID NO 11
<211> LENGTH: 2337
<212> TYPE: DNA
<213> ORGANISM: Aspergillus niger

<400> SEQUENCE: 11

```
caagcaaaca catcctacgt tgattacaac atcgaggcaa accctgatct ttatccactc      60
tgcattgaga ctattccact ttcctttcct gattgtcaaa atggtccatt gagatcacat     120
cttatttgtg atgaaacagc tactccttat gatagggctg caagtctcat atcccttttt     180
acattggatg agttaatcgc taacacagga aacactggtc ttggagtgtc tagacttggt     240
ttgccagctt accaagtttg gtcagaagca ctccacggac ttgatagggc taattttttct    300 gattcaggtg cttataactg gcaacttctt tcccacagc ctattttgac tacagctgca     360
ctcaacagaa cacttatcca tcaaatcgct tctattatat caactcaggg aagagctttt     420
aataacgcag gaagatacgg attggatgtg tatgctccta atattaacac attcagacac     480
ccagtttggg gtaggggaca agaaactcct ggagaggatg tgtcacttgc tgctgtttat     540
gcttacgaat atatcacagg tattcaggga ccagatcctg agtctaatct taagctcgct     600
gcaactgcta agcattacgc aggatacgat atagaaaatt ggcataacca cagtagattg     660
ggtaatgata tgaacataac acaacaggat cttccgagt attacactcc tcaattccac      720
gttgctgcaa gggatgctaa ggtgcagagt gttatgtgtg cttacaatgc agtgaacgga     780
gttccagctt gcgcagattc ttatttttctt caaacacttt tgagagatac ttttggtttc     840
gtggatcatg gatacgtttc ttcagattgt gatgctgcat acaatatcta taccctcac      900 ggttatgcta gttcccaagc tgctgctgct gctgaagcta tccttgcagg aactgatatt     960
gattgcggta ctacatatca gtggcatctc aatgagtcta ttgcagctgg agatctttca    1020
agagatgata ttgagcaagg tgtgataagg ttgtacacta cattagttca ggcaggttac    1080
ttcgattcaa acactacaaa ggctaataac ccatacaggg atttgagttg gtccgatgtt    1140
ctcgaaacag atgcttggaa catctcttat caagcagcta ctcagggaat agtgttactc    1200
aagaactcaa ataacgttct tcctttgact gagaaagcat atccacctag taatactaca    1260
gttgctttga ttggtccatg ggctaacgca actacacaac ttttgggtaa ttattacgga    1320
aacgctcctt acatgatctc tccaagagca gcttttgaag aggcaggata taaggttaat    1380
ttcgctgaag gtacaggaat atcttcaaca tctacttcag gttttgcagc tgcacttagt    1440
gctgcacagt ccgctgatgt tattatatat gcaggaggta tagataacac tctcgaagct    1500
gaggcacttg atagggagtc tatcgcatgg cctggaaacc aattagatct cattcagaaa    1560
cttgcttctg ctgctggaaa gaagccattg attgtgttac aaatgggagg tggacaggtt    1620
```

```
gatagttcct ctttgaagaa taacacaaac gttagtgctt tactctgggg tggatatcct    1680
ggacaatccg gtggatttgc acttagagat atcatcactg gaaagaaaaa tccagctggt    1740
aggcttgtta ctacacagta ccctgcttct tatgctgaag agttcccagc tactgatatg    1800
aatcttagac ctgaaggaga taacccagga caaacataca agtggtatac tggtgaagca    1860
gtttacgagt ttggtcatgg attgttttat actacattcg ctgaatcaag ttccaatact    1920
acaactaagg aggtgaaact caacatacaa gatatcctta gtcagacaca cgaagatttg    1980
gcatccataa ctcaactccc agttcttaac ttcacagcta acatcaggaa cactggaaaa    2040
cttgagtctg attacacagc tatggtgttc gcaaacactt cagatgctgg tccagcacct    2100
tatccaaaga atggttggt tggttgggat agattaggag aggttaaagt gggtgaaaca    2160
agagagctta gggttcctgt ggaagttgga tcttttgcaa gggtgaatga ggatggagat    2220
tgggttgtgt ttccaggtac tttcgaactt gctttgaact agagagaaa agttagggtg    2280 aaggttgtgc ttgaaggtga agaggaagtg gtgttgaaat ggcctggaaa agagtga      2337
```

<210> SEQ ID NO 12
<211> LENGTH: 778
<212> TYPE: PRT
<213> ORGANISM: Aspergillus niger

<400> SEQUENCE: 12

```
Gln Ala Asn Thr Ser Tyr Val Asp Tyr Asn Ile Glu Ala Asn Pro Asp
1               5                   10                  15

Leu Tyr Pro Leu Cys Ile Glu Thr Ile Pro Leu Ser Phe Pro Asp Cys
            20                  25                  30

Gln Asn Gly Pro Leu Arg Ser His Leu Ile Cys Asp Glu Thr Ala Thr
        35                  40                  45

Pro Tyr Asp Arg Ala Ala Ser Leu Ile Ser Leu Phe Thr Leu Asp Glu
    50                  55                  60

Leu Ile Ala Asn Thr Gly Asn Thr Gly Leu Gly Val Ser Arg Leu Gly
65                  70                  75                  80

Leu Pro Ala Tyr Gln Val Trp Ser Glu Ala Leu His Gly Leu Asp Arg
                85                  90                  95

Ala Asn Phe Ser Asp Ser Gly Ala Tyr Asn Trp Ala Thr Ser Phe Pro
            100                 105                 110

Gln Pro Ile Leu Thr Thr Ala Ala Leu Asn Arg Thr Leu Ile His Gln
        115                 120                 125

Ile Ala Ser Ile Ile Ser Thr Gln Gly Arg Ala Phe Asn Asn Ala Gly
    130                 135                 140

Arg Tyr Gly Leu Asp Val Tyr Ala Pro Asn Ile Asn Thr Phe Arg His
145                 150                 155                 160

Pro Val Trp Gly Arg Gly Gln Glu Thr Pro Gly Glu Asp Val Ser Leu
                165                 170                 175

Ala Ala Val Tyr Ala Tyr Glu Tyr Ile Thr Gly Ile Gln Gly Pro Asp
            180                 185                 190

Pro Glu Ser Asn Leu Lys Leu Ala Ala Thr Ala Lys His Tyr Ala Gly
        195                 200                 205

Tyr Asp Ile Glu Asn Trp His Asn His Ser Arg Leu Gly Asn Asp Met
    210                 215                 220

Asn Ile Thr Gln Gln Asp Leu Ser Glu Tyr Tyr Thr Pro Gln Phe His
225                 230                 235                 240

Val Ala Ala Arg Asp Ala Lys Val Gln Ser Val Met Cys Ala Tyr Asn
                245                 250                 255
```

```
Ala Val Asn Gly Val Pro Ala Cys Ala Asp Ser Tyr Phe Leu Gln Thr
            260                 265                 270

Leu Leu Arg Asp Thr Phe Gly Phe Val Asp His Gly Tyr Val Ser Ser
            275                 280                 285

Asp Cys Asp Ala Ala Tyr Asn Ile Tyr Asn Pro His Gly Tyr Ala Ser
290                 295                 300

Ser Gln Ala Ala Ala Ala Glu Ala Ile Leu Ala Gly Thr Asp Ile
305                 310                 315                 320

Asp Cys Gly Thr Thr Tyr Gln Trp His Leu Asn Glu Ser Ile Ala Ala
            325                 330                 335

Gly Asp Leu Ser Arg Asp Ile Glu Gln Gly Val Ile Arg Leu Tyr
            340                 345                 350

Thr Thr Leu Val Gln Ala Gly Tyr Phe Asp Ser Asn Thr Thr Lys Ala
            355                 360                 365

Asn Asn Pro Tyr Arg Asp Leu Ser Trp Ser Asp Val Leu Glu Thr Asp
            370                 375                 380

Ala Trp Asn Ile Ser Tyr Gln Ala Ala Thr Gln Gly Ile Val Leu Leu
385                 390                 395                 400

Lys Asn Ser Asn Asn Val Leu Pro Leu Thr Glu Lys Ala Tyr Pro Pro
            405                 410                 415

Ser Asn Thr Thr Val Ala Leu Ile Gly Pro Trp Ala Asn Ala Thr Thr
            420                 425                 430

Gln Leu Leu Gly Asn Tyr Tyr Gly Asn Ala Pro Tyr Met Ile Ser Pro
            435                 440                 445

Arg Ala Ala Phe Glu Glu Ala Gly Tyr Lys Val Asn Phe Ala Glu Gly
            450                 455                 460

Thr Gly Ile Ser Ser Thr Ser Thr Ser Gly Phe Ala Ala Ala Leu Ser
465                 470                 475                 480

Ala Ala Gln Ser Ala Asp Val Ile Ile Tyr Ala Gly Gly Ile Asp Asn
                485                 490                 495

Thr Leu Glu Ala Glu Ala Leu Asp Arg Glu Ser Ile Ala Trp Pro Gly
            500                 505                 510

Asn Gln Leu Asp Leu Ile Gln Lys Leu Ala Ser Ala Ala Gly Lys Lys
            515                 520                 525

Pro Leu Ile Val Leu Gln Met Gly Gly Gly Gln Val Asp Ser Ser Ser
530                 535                 540

Leu Lys Asn Asn Thr Asn Val Ser Ala Leu Leu Trp Gly Gly Tyr Pro
545                 550                 555                 560

Gly Gln Ser Gly Gly Phe Ala Leu Arg Asp Ile Ile Thr Gly Lys Lys
            565                 570                 575

Asn Pro Ala Gly Arg Leu Val Thr Thr Gln Tyr Pro Ala Ser Tyr Ala
            580                 585                 590

Glu Glu Phe Pro Ala Thr Asp Met Asn Leu Arg Pro Glu Gly Asp Asn
            595                 600                 605

Pro Gly Gln Thr Tyr Lys Trp Tyr Thr Gly Glu Ala Val Tyr Glu Phe
            610                 615                 620

Gly His Gly Leu Phe Tyr Thr Thr Phe Ala Glu Ser Ser Ser Asn Thr
625                 630                 635                 640

Thr Thr Lys Glu Val Lys Leu Asn Ile Gln Asp Ile Leu Ser Gln Thr
            645                 650                 655

His Glu Asp Leu Ala Ser Ile Thr Gln Leu Pro Val Leu Asn Phe Thr
            660                 665                 670
```

```
        Ala Asn Ile Arg Asn Thr Gly Lys Leu Glu Ser Asp Tyr Thr Ala Met
                    675                 680                 685

Val Phe Ala Asn Thr Ser Asp Ala Gly Pro Ala Pro Tyr Pro Lys Lys
            690                 695                 700

Trp Leu Val Gly Trp Asp Arg Leu Gly Glu Val Lys Val Gly Glu Thr
        705                 710                 715                 720

Arg Glu Leu Arg Val Pro Val Glu Val Gly Ser Phe Ala Arg Val Asn
                        725                 730                 735

Glu Asp Gly Asp Trp Val Val Phe Pro Gly Thr Phe Glu Leu Ala Leu
                    740                 745                 750

Asn Leu Glu Arg Lys Val Arg Val Lys Val Val Leu Glu Gly Glu Glu
                755                 760                 765

Glu Val Val Leu Lys Trp Pro Gly Lys Glu
            770                 775
```

<210> SEQ ID NO 13
<211> LENGTH: 1557
<212> TYPE: DNA
<213> ORGANISM: Streptomyces sp.

<400> SEQUENCE: 13

```
ggtacacctt gtgctgctcc tgtgaaacct gcatcccaaa tggctgttga atcttgcgat        60
agtcctgaga gaatcataga aaaagctgct aatattgtgc caacttctgg acaacttgct       120
tggcaacaga gagaggttac tgcttttact catttcggta tgaatacttt tacaggaagg       180
gaatggggaa gtggtacaga agatgagaaa cttttcgctc caaagtccat agatgttgat       240
cagtggatga gagcttataa ggctgctgga gcagagcagg ttatgctcac tgctaagcat       300
cacgatggtt ttgtgcttta tcctagtaga tacacagatc actccgttga actttctcca       360
ggatcacctg atgttgtggg tgcttatgtt aaggctgcaa ggaaagcagg attgaaagtg       420
ggtctctacc tttctccttc agatggagct gaattaccac atgcatggca cgctcaatgg       480
gttgaatcta tcagaaagaa acaggctgag ggaaaaccat tgtcattacc tgaacaaatg       540
gcattggagg atgagagtag agcaccagct ggagaaggaa ggtttggaaa tggttcagct       600
gtgactgaga ggacaattcc aactcttgtt cctggagatg tagagctgc tgctgttaag       660 aggcataaac ttcctacttt tacagttatg gctgatgatt atgatgcata ctacctcaac       720
caactttacg agatattcac tcagtacgga ccaatcgaag aactttggct tgatggtgct       780
aatccttgga gtggatccgg tattactcaa aaatacaacg tgaagcagtg gtttgatatg       840
gttaaggctc ttagtcctaa tacagttgtg ttccaaggac cacagggtgt gagatggtt        900 ggaaacgaag gaggtacagc tagggaaact gagtggtcag ttacacctca tgcaactgat       960
ccatggacag gattgggttc tttaccaaat gattcaactg atgctgatat cggtagtaga      1020
gcaaggattt tggatcctac tacaaagtat cttcaatggt acccagcaga agctgatgtt      1080
tccattagac ctggatggtt ttatcaccca gagcaacagc ctaaaactgc tccacagctc      1140
atgaaccttt acgaaaagtc tgttggtagg aatgcagctc ttttgttaaa cgtgccacct      1200
ggaagagatg gtaggatagc agatgctgat gttgcatctc ttacagcttt cggaaaagca      1260
gtgagatcta cttatggaac tgatgttaga aggactcaag ctccaggtcc ttacacattt      1320
gatagagttg cagtgaggga ggatatcaga catggacaaa gggtggaaaa gttcgcagtt      1380
gaggctagaa ttgatggttc atggcagagg atagctgaag gaactactat tggaaacaga      1440
aggatattga gtttagcatc ccctgttact gcaacagctg ttagagtgaa ggttcttgaa      1500
```
tcaagggcaa ctccacattt gggtgctact acactccatt tgtcatctac aggataa    1557

<210> SEQ ID NO 14
<211> LENGTH: 518
<212> TYPE: PRT
<213> ORGANISM: Streptomyces sp.

<400> SEQUENCE: 14

Gly Thr Pro Cys Ala Ala Pro Val Lys Pro Ala Ser Gln Met Ala Val
1               5                   10                  15

Glu Ser Cys Asp Ser Pro Glu Arg Ile Ile Glu Lys Ala Ala Asn Ile
            20                  25                  30

Val Pro Thr Ser Gly Gln Leu Ala Trp Gln Gln Arg Glu Val Thr Ala
        35                  40                  45

Phe Thr His Phe Gly Met Asn Thr Phe Thr Gly Arg Glu Trp Gly Ser
    50                  55                  60

Gly Thr Glu Asp Glu Lys Leu Phe Ala Pro Lys Ser Ile Asp Val Asp
65                  70                  75                  80

Gln Trp Met Arg Ala Tyr Lys Ala Ala Gly Ala Glu Gln Val Met Leu
                85                  90                  95

Thr Ala Lys His His Asp Gly Phe Val Leu Tyr Pro Ser Arg Tyr Thr
            100                 105                 110

Asp His Ser Val Glu Leu Ser Pro Gly Ser Pro Asp Val Val Gly Ala
        115                 120                 125

Tyr Val Lys Ala Ala Arg Lys Ala Gly Leu Lys Val Gly Leu Tyr Leu
    130                 135                 140

Ser Pro Ser Asp Gly Ala Glu Leu Pro His Ala Trp His Ala Gln Trp
145                 150                 155                 160

Val Glu Ser Ile Arg Lys Lys Gln Ala Glu Gly Lys Pro Leu Ser Leu
                165                 170                 175

Pro Glu Gln Met Ala Leu Glu Asp Gly Asp Arg Ala Pro Ala Gly Glu
            180                 185                 190

Gly Arg Phe Gly Asn Gly Ser Ala Val Thr Glu Arg Thr Ile Pro Thr
        195                 200                 205

Leu Val Pro Gly Asp Asp Arg Ala Ala Ala Val Lys Arg His Lys Leu
    210                 215                 220

Pro Thr Phe Thr Val Met Ala Asp Asp Tyr Asp Ala Tyr Tyr Leu Asn
225                 230                 235                 240

Gln Leu Tyr Glu Ile Phe Thr Gln Tyr Gly Pro Ile Glu Glu Leu Trp
                245                 250                 255

Leu Asp Gly Ala Asn Pro Trp Ser Gly Ser Gly Ile Thr Gln Lys Tyr
            260                 265                 270

Asn Val Lys Gln Trp Phe Asp Met Val Lys Ala Leu Ser Pro Asn Thr
        275                 280                 285

Val Val Phe Gln Gly Pro Gln Gly Val Arg Trp Val Gly Asn Glu Gly
    290                 295                 300

Gly Thr Ala Arg Glu Thr Glu Trp Ser Val Thr Pro His Ala Thr Asp
305                 310                 315                 320

Pro Trp Thr Gly Leu Gly Ser Leu Pro Asn Asp Ser Thr Asp Ala Asp
                325                 330                 335

Ile Gly Ser Arg Ala Arg Ile Leu Asp Pro Thr Thr Lys Tyr Leu Gln
            340                 345                 350

Trp Tyr Pro Ala Glu Ala Asp Val Ser Ile Arg Pro Gly Trp Phe Tyr
        355                 360                 365

```
His Pro Glu Gln Gln Pro Lys Thr Ala Pro Gln Leu Met Asn Leu Tyr
    370                 375                 380

Glu Lys Ser Val Gly Arg Asn Ala Ala Leu Leu Leu Asn Val Pro Pro
385                 390                 395                 400

Gly Arg Asp Gly Arg Ile Ala Asp Ala Asp Val Ala Ser Leu Thr Ala
                405                 410                 415

Phe Gly Lys Ala Val Arg Ser Thr Tyr Gly Thr Asp Val Arg Arg Thr
            420                 425                 430

Gln Ala Pro Gly Pro Tyr Thr Phe Asp Arg Val Ala Val Arg Glu Asp
                435                 440                 445

Ile Arg His Gly Gln Arg Val Glu Lys Phe Ala Val Glu Ala Arg Ile
    450                 455                 460

Asp Gly Ser Trp Gln Arg Ile Ala Glu Gly Thr Thr Ile Gly Asn Arg
465                 470                 475                 480

Arg Ile Leu Ser Leu Ala Ser Pro Val Thr Ala Thr Ala Val Arg Val
                485                 490                 495

Lys Val Leu Glu Ser Arg Ala Thr Pro His Leu Gly Ala Thr Thr Leu
                500                 505                 510

His Leu Ser Ser Thr Gly
        515
```

<210> SEQ ID NO 15
<211> LENGTH: 1365
<212> TYPE: DNA
<213> ORGANISM: Artificial sequence
<220> FEATURE:
<223> OTHER INFORMATION: nucleotide sequence encoding Humira heavy chain

<400> SEQUENCE: 15

```
gcgcagcttg aagtgcaatt ggttgaatca ggaggaggac tcgtgcaacc gggaaggagt      60
ttacgattat cttgtgctgc ctctggattc acctttgacg actatgcaat gcattgggtc     120
cgtcaagcac aggaaaaagg tttagagtgg gtttcagcaa tcacttggaa ctccggacat     180
attgactatg ccgatagtgt tgagggtcga ttcacaatct cacgagataa cgcgaagaat     240
agtctatacc tacagatgaa tagcctaaga gctgaggata ctgccgttta ttactgtgca     300
aaggtttcct atctttctac tgcatctagt cttgattact ggggacaagg aacacttgtc     360
acagttcct ctgctagcac aaaaggacct agcgttttcc ctctggcacc atcaagtaag     420
agcaccagtg gcgggacagc agcactgggt tgtcttgtga agactatttt cccagaaccc     480
gttaccgtta gttggaactc aggcgcactt acttcgggag ttcatacttt tcctgctgtc     540
ttacaatctt ccggtctcta ttcactaagc tcagttgtca ctgtaccttc ctcaagcctt     600
gggacacaaa cctacatttg taacgtcaat cataaaccga gcaatacgaa ggtagataag     660
aaagtcgagc aaagagttg tgataaaaca cacacttgcc caccttgccc agctcctgaa     720
ctcttaggtg gaccaagcgt tttcctcttt cctccaaagc cgaaagatac acttatgata     780
tcacgcacac ccgaagttac ttgtgtggtt gtagacgttt ctcatgaaga tcccgaagtg     840
aagtttaatt ggtacgtcga tggtgttgaa gttcacaatg ctaagactaa gccaagagaa     900
gagcaataca actcaaccta tagagttgtt tccgtcttaa ccgtactgca tcaagattgg     960
ttgaacggca aggagtataa atgcaaggtt agcaataaag cactacctgc accgattgag    1020
aagacaatta gcaaagcaaa aggacaacca agggaaccac aagtctatac acttccacct    1080
tcaagggat agctgactaa gaatcaagta tccttgacct gtttagtcaa ggggttttac    1140
ccttctgaca ttgccgtaga atgggaatct aatgggcagc ctgagaataa ctataagaca    1200
```

```
actccacccg tactcgattc tgacggctct tttttcctat actccaagct aaccgtggat    1260
aaatcacgtt ggcaacaagg aaacgttttc tcttgttctg tgatgcacga ggctttgcat    1320
aatcactaca cacaaaagag cttaagtctt agccctggga aatag                    1365

<210> SEQ ID NO 16
<211> LENGTH: 645
<212> TYPE: DNA
<213> ORGANISM: Artificial sequence
<220> FEATURE:
<223> OTHER INFORMATION: nucleotide sequence encoding Humira light chain

<400> SEQUENCE: 16
gacatacaaa tgactcaatc tccaagttca ctatctgctt cagtcggcga tagggtcact     60
ataacttgta gagcctctca gggcataaga aactatttgg catggtacca acagaaacct    120
ggaaaagctc ctaagctgct aatatatgct gcttctacac ttcagagtgg agtaccttca    180
agattcagtg gatctggttc tgggactgat ttcactttga ctatctcatc cctccaacca    240
gaagacgttg ctacatacta ttgccagcgc tataataggg ctccttatac ctttggacaa    300
ggcacaaaag tcgagattaa agaactgttg ctgcaccat cagtgtttat tttccctcca    360
agtgacgaac agcttaaatc tggaactgca agcgttgtat gccttctcaa caatttctac    420
cctagagaag cgaaagtcca atggaaagta gataacgcac ttcagtctgg gaactcacaa    480
gagagtgtca ctgaacaaga ttcgaaagac tctacctatt cactctcatc gactcttact    540
ctgtcaaaag ctgattacga gaagcacaaa gtgtatgctt gcgaagttac acaccaagga    600
cttagctcac cagtaaccaa gagcttcaat aggggagaat gctga                    645

<210> SEQ ID NO 17
<211> LENGTH: 141
<212> TYPE: DNA
<213> ORGANISM: Artificial sequence
<220> FEATURE:
<223> OTHER INFORMATION: nucleotide sequence encoding Vacuolar SP signal
      peptide

<400> SEQUENCE: 17
atggctcacg ctagagtttt attactcgct ctcgcagttc tcgctacagc agcagtggct     60
gtggcttcaa gttcttcatt cgctgattca aatccaatta gacctgttac tgatagggct    120
gcaagtacat tggctcaact t                                              141

<210> SEQ ID NO 18
<211> LENGTH: 132
<212> TYPE: DNA
<213> ORGANISM: Artificial sequence
<220> FEATURE:
<223> OTHER INFORMATION: nucleotide sequence encoding Vacuolar SP1
      signal peptide

<400> SEQUENCE: 18
atggcccatg cacgagtctt gcttctcgct ttagctgtgc tagcaactgc agccgttgct     60
gtggcctcct cttcttcatt tgcggattca aatccaattc gtcccgtcac tgatagagct    120
gcttctacac ta                                                        132

<210> SEQ ID NO 19
<211> LENGTH: 141
<212> TYPE: DNA
<213> ORGANISM: Artificial sequence
<220> FEATURE:
```

<223> OTHER INFORMATION: nucleotide sequence encoding Vacuolar SP2
      signal peptide

<400> SEQUENCE: 19
atggcacacg ctcgagttct gttactagct ctagcagtgc tagctactgc tgccgttgca    60
gtcgcctcct cttcttcctt tgctgattca aatccaatcc gtcccgtcac agatagagct   120
gcctcaacac tagctcagct t                                             141

<210> SEQ ID NO 20
<211> LENGTH: 47
<212> TYPE: PRT
<213> ORGANISM: Artificial sequence
<220> FEATURE:
<223> OTHER INFORMATION: Vacuolar SP signal peptide sequence

<400> SEQUENCE: 20

Met Ala His Ala Arg Val Leu Leu Leu Ala Leu Ala Val Leu Ala Thr
1               5                   10                  15

Ala Ala Val Ala Val Ala Ser Ser Ser Ser Phe Ala Asp Ser Asn Pro
            20                  25                  30

Ile Arg Pro Val Thr Asp Arg Ala Ala Ser Thr Leu Ala Gln Leu
        35                  40                  45

<210> SEQ ID NO 21
<211> LENGTH: 75
<212> TYPE: DNA
<213> ORGANISM: Artificial Sequence
<220> FEATURE:
<223> OTHER INFORMATION: nucleotide sequence encoding short cel-1 signal
      peptide

<400> SEQUENCE: 21
atggccgcaa gaaagtccct catattccct gtgatactcc tcgcagtttt gttgtttagt    60
ccaccaatct actcc                                                     75

<210> SEQ ID NO 22
<211> LENGTH: 25
<212> TYPE: PRT
<213> ORGANISM: Arabidopsis thaliana

<400> SEQUENCE: 22

Met Ala Ala Arg Lys Ser Leu Ile Phe Pro Val Ile Leu Leu Ala Val
1               5                   10                  15

Leu Leu Phe Ser Pro Pro Ile Tyr Ser
            20                  25

<210> SEQ ID NO 23
<211> LENGTH: 117
<212> TYPE: DNA
<213> ORGANISM: Artificial sequence
<220> FEATURE:
<223> OTHER INFORMATION: nucleotide sequence encoding cel-1 signal
      peptide

<400> SEQUENCE: 23
atggctagga agtctttgat tttcccagtg attcttcttg ctgtgcttct tttctctcca    60
cctatttact ctgctggaca cgattatagg gatgctctta ggaagtcatc tatggct     117

<210> SEQ ID NO 24
<211> LENGTH: 39
<212> TYPE: PRT
<213> ORGANISM: Arabidopsis thaliana -continued

<400> SEQUENCE: 24

Met Ala Arg Lys Ser Leu Ile Phe Pro Val Ile Leu Leu Ala Val Leu
1 5 10 15

Leu Phe Ser Pro Pro Ile Tyr Ser Ala Gly His Asp Tyr Arg Asp Ala
20 25 30

Leu Arg Lys Ser Ser Met Ala
35

<210> SEQ ID NO 25
<211> LENGTH: 4231
<212> TYPE: DNA
<213> ORGANISM: Artificial sequence
<220> FEATURE:
<223> OTHER INFORMATION: nucleotide sequence encoding both Vacuolar SP and both Humira chains optimized for tobacco by Leto

<400> SEQUENCE: 25
ccatggccca tgcacgagtc ttgcttctcg ctttagctgt gctagcaact gcagccgttg 60
ctgtggcctc ctcttcttca tttgcggatt caaatccaat tcgtcccgtc actgatagag 120
ctgcttctac actagcgcag cttgaagtgc aattggttga atcaggagga ggactcgtgc 180
aaccgggaag gagtttacga ttatcttgtg ctgcctctgg attcaccttt gacgactatg 240
caatgcattg ggtccgtcaa gcaccaggaa aaggtttaga gtgggtttca gcaatcactt 300
ggaactccgg acatattgac tatgccgata gtgttgaggg tcgattcaca atctcacgag 360
ataacgcgaa gaatagtcta tacctacaga tgaatagcct aagagctgag gatactgccg 420
tttattactg tgcaaaggtt tcctatcttt ctactgcatc tagtcttgat tactggggac 480
aaggaacact tgtcacagtt tcctctgcta gcacaaaagg acctagcgtt ttccctctgg 540
caccatcaag taagagcacc agtggcggga cagcagcact gggttgtctt gtgaaagact 600
atttcccaga acccgttacc gttagttgga actcaggcgc acttacttcg ggagttcata 660
cttttcctgc tgtcttacaa tcttccggtc tctattcact aagctcagtt gtcactgtac 720
cttcctcaag ccttgggaca caaacctaca tttgtaacgt caatcataaa ccgagcaata 780
cgaaggtaga taagaaagtc gagccaaaga gttgtgataa aacacacact tgcccacctt 840
gcccagctcc tgaactctta ggtggaccaa gcgttttcct ctttcctcca aagccgaaag 900
atacacttat gatatcacgc acacccgaag ttacttgtgt ggttgtagac gtttctcatg 960
aagatcccga agtgaagttt aattggtacg tcgatggtgt tgaagttcac aatgctaaga 1020
ctaagccaag agaagagcaa tacaactcaa cctatagagt tgtttccgtc ttaaccgtac 1080
tgcatcaaga ttggttgaac ggcaaggagt ataaatgcaa ggttagcaat aaagcactac 1140
ctgcaccgat tgagaagaca attagcaaag caaaaggaca accaagggaa ccacaagtct 1200
atacacttcc accttcaagg gatgagctga ctaagaatca agtatccttg acctgtttag 1260
tcaaggggtt ttacccttct gacattgccg tagaatggga atctaatggg cagcctgaga 1320
ataactataa gacaactcca cccgtactcg attctgacgg ctcttttttc ctatactcca 1380
agctaaccgt ggataaatca cgttggcaac aaggaaacgt tttctcttgt tctgtgatgc 1440
acgaggcttt gcataatcac tacacacaaa agagcttaag tcttagccct gggaaataga 1500
taagttttac tatttaccaa gacttttgaa tattaacctt cttgtaacga gtcggttaaa 1560
tttgattgtt tagggttttg tattattttt ttttggtctt ttaattcatc actttaattc 1620
cctaattgtc tgttcatttc gttgtttgtt tccggatcga taatgaaatg taagagatat 1680

```
catatataaa taataaattg tcgtttcata tttgcaatct ttttttacaa acctttaatt    1740
aattgtatgt atgacatttt cttcttgtta tattagggg aaataatgtt aaataaaagt     1800
acaaaataaa ctacagtaca tcgtactgaa taaattacct agccaaaaag tacacctttc    1860
catatacttc ctcatgaag gcattttcaa cattttcaaa taaggaatgc tacaaccgca     1920
taataacatc cacaaatttt tttataaaat aacatgtcag acagtgattg aaagatttta    1980
ttatagtttc gttatcttct tttctcatta agcgaatcac tacctaacac gtcattttgt    2040
gaaatatttt ttgaatgttt ttatatagtt gtagcattcc tcttttcaaa ttagggtttg    2100
tttgagatag catttcagcc ggttcataca acttaaaagc atactctaat gctggaaaaa    2160
agactaaaaa atcttgtaag ttagcgcaga atattgaccc aaattatata cacacatgac    2220
cccatataga gactaattac acttttaacc actaataatt attactgtat tataacatct    2280
actaattaaa cttgtgagtt tttgctagaa ttattatcat atatactaaa aggcaggaac    2340
gcaaacattg ccccggtact gtagcaacta cggtagacgc attaattgtc tatagtggac    2400
gcattaatta accaaaaccg cctctttccc cttcttcttg acgcgttaga caaacacccc    2460
ttgttataca aagaatttcg ctttacaaaa tcaaattcga gaaaataata tatgcactaa    2520
ataagatcat tcggatccaa tctaaccaat tacgatacg tttgggtaca cttgattttt     2580
gtttcagtag ttacatatat cttgttttat atgctatctt taaggatctt cactcaaaga    2640
ctatttgttg atgttcttga tggggctcgg aagatttgat atgatacact ctaatcttta    2700
ggagatacca gccaggatta tattcagtaa gacaatcaaa ttttacgtgt tcaaactcgt    2760
tatcttttca tttaatggat gagccagaat ctctatagaa tgattgcaat cgagaatatg    2820
ttcggccgat atccctttgt tggcttcaat attctacata tcacacaaga atcgaccgta    2880
ttgtaccctc tttccataaa ggaacacaca gtatgcagat gcttttttcc cacatgcagt    2940
aacataggta ttcaaaaatg gctaaagaa gttggataac aaattgacaa ctatttccat     3000
ttctgttata taaatttcac aacacacaaa agcccgtaat caagagtctg cccatgtacg    3060
aaataacttc tattatttgg tattgggcct aagcccagct cagagtacgt ggggtacca     3120 catataggaa ggtaacaaaa tactgcaaga tagcccccata acgtaccagc ctctccttac    3180
cacgaagaga taagatataa gacccacccct gccacgtgtc acatcgtcat ggtggttaat    3240
gataagggat tacatccttc tatgtttgtg gacatgatgc atgtaatgtc atgagccaca    3300
tgatccaatg gccacaggaa cgtaagaatg tagatagatt tgattttgtc cgttagatag    3360
caaacaacat tataaaaggt gtgtatcaat acgaactaat tcactcattg gattcataga    3420
agtccattcc tcctaagtat ctaaacaatg gcacactgtt actagctcta gcagtgctag    3480
ctactgctgc cgttgcagtc gcctcctctt cttcctttgc tgattcaaat ccaatccgtc    3540
ccgtcacaga tagagctgcc tcaacactag ctcagcttga catacaaatg actcaatctc    3600
caagttcact atctgcttca gtcggcgata gggtcactat aacttgtaga gcctctcagg    3660
gcataagaaa ctatttggca tggtaccaac agaaacctgg aaaagctcct aagctgctaa    3720
tatatgctgc ttctacactt cagagtggag taccttcaag attcagtgga tctggttctg    3780
ggactgattt cactttgact atctcatccc tccaaccaga agacgttgct acatactatt    3840
gccagcgcta taataggct ccttatacct ttggacaagg cacaaaagtc gagattaaga     3900
gaactgttgc tgcaccatca gtgtttattt tccctccaag tgacgaacag cttaaatctg    3960
gaactgcaag cgttgtatgc cttctcaaca atttctaccc tagagaagcg aaagtccaat    4020
ggaaagtaga taacgcactt cagtctggga actcacaaga gagtgtcact gaacaagatt    4080
```

| | | | | |
|---|---|---|---|---|
| cgaaagactc | tacctattca | ctctcatcga | ctcttactct | gtcaaaagct gattacgaga | 4140 |
| agcacaaagt | gtatgcttgc | gaagttacac | accaaggact | tagctcacca gtaaccaaga | 4200 |
| gcttcaatag | gggagaatgc | tgagcggccg | c | | 4231 |

<210> SEQ ID NO 26
<211> LENGTH: 1016
<212> TYPE: DNA
<213> ORGANISM: Artificial sequence
<220> FEATURE:
<223> OTHER INFORMATION: nucleotide sequence encoding Rubisco promoter

<400> SEQUENCE: 26

| | | | | |
|---|---|---|---|---|
| aattcgatat | caagcttaga | caaacacccc | ttgttataca | aagaatttcg ctttacaaaa | 60 |
| tcaaattcga | gaaataata | tatgcactaa | ataagatcat | tcggatccaa tctaaccaat | 120 |
| tacgatacgc | tttgggtaca | cttgattttt | gtttcagtag | ttacatatat cttgttttat | 180 |
| atgctatctt | taaggatctt | cactcaaaga | ctatttgttg | atgttcttga tggggctcgg | 240 |
| aagatttgat | atgatacact | ctaatcttta | ggagatacca | gccaggatta tattcagtaa | 300 |
| gacaatcaaa | ttttacgtgt | tcaaactcgt | tatcttttca | tttaatggat gagccagaat | 360 |
| ctctatagaa | tgattgcaat | cgagaatatg | ttcggccgat | atcccttgt tggcttcaat | 420 |
| attctacata | tcacacaaga | atcgaccgta | ttgtaccctc | tttccataaa ggaacacaca | 480 |
| gtatgcagat | gcttttttcc | cacatgcagt | aacataggta | ttcaaaaatg ctaaaagaa | 540 |
| gttggataac | aaattgacaa | ctatttccat | ttctgttata | taaatttcac aacacacaaa | 600 |
| agcccgtaat | caagagtctg | cccatgtacg | aaataacttc | tattatttgg tattgggcct | 660 |
| aagcccagct | cagagtacgt | gggggtacca | catataggaa | ggtaacaaaa tactgcaaga | 720 |
| tagccccata | acgtaccagc | ctctccttac | cacgaagaga | taagatataa gacccaccct | 780 |
| gccacgtgtc | acatcgtcat | ggtggttaat | gataagggat | tacatccttc tatgtttgtg | 840 |
| gacatgatgc | atgtaatgtc | atgagccaca | tgatccaatg | gccacaggaa cgtaagaatg | 900 |
| tagatagatt | tgattttgtc | cgttagatag | caaacaacat | tataaaaggt gtgtatcaat | 960 |
| acgaactaat | tcactcattg | gattcataga | agtccattcc | tcctaagtat ctaaac | 1016 |

<210> SEQ ID NO 27
<211> LENGTH: 960
<212> TYPE: DNA
<213> ORGANISM: Artificial sequence
<220> FEATURE:
<223> OTHER INFORMATION: nucleotide sequence encoding Rubisco terminator

<400> SEQUENCE: 27

| | | | | |
|---|---|---|---|---|
| ggccgcataa | gttttactat | ttaccaagac | ttttgaatat | taaccttctt gtaacgagtc | 60 |
| ggttaaattt | gattgtttag | ggttttgtat | tattttttt | tggtcttta attcatcact | 120 |
| ttaattccct | aattgtctgt | tcatttcgtt | gtttgtttcc | ggatcgataa tgaaatgtaa | 180 |
| gagatatcat | atataaataa | taaattgtcg | tttcatattt | gcaatctttt tttacaaacc | 240 |
| tttaattaat | tgtatgtatg | acattttctt | cttgttatat | tagggggaaa taatgttaaa | 300 |
| taaaagtaca | aaataaacta | cagtacatcg | tactgaataa | attacctagc caaaaagtac | 360 |
| acctttccat | atacttccta | catgaaggca | ttttcaacat | tttcaaataa ggaatgctac | 420 |
| aaccgcataa | taacatccac | aaattttttt | ataaaataac | atgtcagaca gtgattgaaa | 480 |
| gattttatta | tagtttcgtt | atcttctttt | ctcattaagc | gaatcactac ctaacacgtc | 540 |

| | |
|---|---|
| attttgtgaa atattttttg aatgttttta tatagttgta gcattcctct tttcaaatta | 600 |
| gggtttgttt gagatagcat ttcagccggt tcatacaact taaaagcata ctctaatgct | 660 |
| ggaaaaaaga ctaaaaaatc ttgtaagtta gcgcagaata ttgacccaaa ttatatacac | 720 |
| acatgaccccc atatagagac taattacact tttaaccact aataattatt actgtattat | 780 |
| aacatctact aattaaactt gtgagttttt gctagaatta ttatcatata tactaaaagg | 840 |
| caggaacgca aacattgccc cggtactgta gcaactacgg tagacgcatt aattgtctat | 900 |
| agtggacgca ttaattaacc aaaaccgcct ctttccccctt cttcttgaag cttgagctcg | 960 |

<210> SEQ ID NO 28
<211> LENGTH: 232
<212> TYPE: DNA
<213> ORGANISM: Artificial sequence
<220> FEATURE:
<223> OTHER INFORMATION: nucleotide sequence encoding NOS terminator

<400> SEQUENCE: 28

| | |
|---|---|
| ggccgctgat cgttcaaaca tttggcaata aagtttctta agattgaatc ctgttgccgg | 60 |
| tcttgcgatg attatcatat aatttctgtt gaattacgtt aagcatgtaa taattaaaca | 120 |
| tgtaatgcat gacgttattt atgagatggg gtttttatga ttaagagtcc ccgcaattat | 180 |
| acattttaat acgcgataga aaacaaaat atagcgccca aactagagct cg | 232 |

<210> SEQ ID NO 29
<211> LENGTH: 555
<212> TYPE: DNA
<213> ORGANISM: Artificial sequence
<220> FEATURE:
<223> OTHER INFORMATION: nucleotide sequence encoding Gene fusion of CBD coding domain

<400> SEQUENCE: 29

| | |
|---|---|
| caattgaatc ttaaggtgga atttttacaac tccaacccat ctgatactac aaattccata | 60 |
| aaccctcaat tcaaggttac taatacagga tcttcagcta tcgatctttc aaaactcact | 120 |
| cttagatact actacacagt ggatggtcaa aaggatcaga ctttttggtg tgatcatgct | 180 |
| gcaattatag gatcaaatgg tagttacaac ggaataactt caaacgttaa gggtacattc | 240 |
| gtgaaaatga gttcctctac taataacgct gatacatatc tcgaaattc ttttactgga | 300 |
| ggtacacttg agccaggtgc tcatgttcaa atacagggaa ggttcgcaaa aaatgattgg | 360 |
| tcaaactaca ctcaatccaa cgattactct tttaagtcag ctagtcaatt cgttgaatgg | 420 |
| gatcaggtga cagcatattt gaatggtgtt ttagtgtggg gtaaagagcc tggaggttca | 480 |
| gttgtgccaa gtactcaacc tgttactaca ccacctgcta ctacaaagcc acctgcaact | 540 |
| acaatcccac ctact | 555 |

<210> SEQ ID NO 30
<211> LENGTH: 783
<212> TYPE: DNA
<213> ORGANISM: Artificial sequence
<220> FEATURE:
<223> OTHER INFORMATION: nucleotide sequence encoding Protein A

<400> SEQUENCE: 30

| | |
|---|---|
| atggaacaaa gaataacatt gaaggaggct tgggatcaaa ggaatggttt tattcagtct | 60 |
| ttaaaggatg atccatccca atctgctaat gtgctcggtg aagcacaaaa acttaacgat | 120 |
| agtcaggctc ctaaagctga tgcacaacaa aataacttta taaggatca acagtctgct | 180 |

```
ttctacgaaa tcctcaatat gccaaatctt aacgaggcac aaagaaatgg tttttattcag      240 tcattgaagg atgatccttc acaaagtaca acgttttgg gtgaagctaa gaaattaaac        300
gagagtcagg ctccaaaggc agataataac ttcaataagg aacaacagaa cgcattctac      360
gagatcttga acatgccaaa tcttaacgaa gagcagcgta atggttttat tcagtcattg      420
aaagatgatc cttcccaatc tgctaatctt ttgtccgaag caagaaaact taacgagtct      480
caggctccta aggcagataa taagtttaac aaagaacaac agaatgcttt ctacgagcat      540
ctccctaatc ttaacgaaga acaaaggaac ggtttcattc agtctttgaa agatgatcca      600
tctcaaagtg caaatcttct cgctgaggca aagaaactta acgatgctca ggcaccaaag      660
gctgacaata agtttaacaa agagcagcaa aacgcattct acgagatatt gcacttacct      720
aacctcactg aagagcagag gaatggtttt atccagagtc tcaaagatga tccaggtaat      780
agt                                                                     783
```

<210> SEQ ID NO 31
<211> LENGTH: 263
<212> TYPE: PRT
<213> ORGANISM: Artificial sequence
<220> FEATURE:
<223> OTHER INFORMATION: Protein A   AA sequence

<400> SEQUENCE: 31

```
Met Glu Gln Arg Ile Thr Leu Lys Glu Ala Trp Asp Gln Arg Asn Gly
 1               5                  10                  15

Phe Ile Gln Ser Leu Lys Asp Asp Pro Ser Gln Ser Ala Asn Val Leu
            20                  25                  30

Gly Glu Ala Gln Lys Leu Asn Asp Ser Gln Ala Pro Lys Ala Asp Ala
        35                  40                  45

Gln Gln Asn Asn Phe Asn Lys Asp Gln Gln Ser Ala Phe Tyr Glu Ile
    50                  55                  60

Leu Asn Met Pro Asn Leu Asn Glu Ala Gln Arg Asn Gly Phe Ile Gln
65                  70                  75                  80

Ser Leu Lys Asp Asp Pro Ser Gln Ser Thr Asn Val Leu Gly Glu Ala
                85                  90                  95

Lys Lys Leu Asn Glu Ser Gln Ala Pro Lys Ala Asp Asn Asn Phe Asn
            100                 105                 110

Lys Glu Gln Gln Asn Ala Phe Tyr Glu Ile Leu Asn Met Pro Asn Leu
        115                 120                 125

Asn Glu Glu Gln Arg Asn Gly Phe Ile Gln Ser Leu Lys Asp Asp Pro
    130                 135                 140

Ser Gln Ser Ala Asn Leu Leu Ser Glu Ala Lys Lys Leu Asn Glu Ser
145                 150                 155                 160

Gln Ala Pro Lys Ala Asp Asn Lys Phe Asn Lys Glu Gln Gln Asn Ala
                165                 170                 175

Phe Tyr Glu Ile Leu His Leu Pro Asn Leu Asn Glu Glu Gln Arg Asn
            180                 185                 190

Gly Phe Ile Gln Ser Leu Lys Asp Asp Pro Ser Gln Ser Ala Asn Leu
        195                 200                 205

Leu Ala Glu Ala Lys Lys Leu Asn Asp Ala Gln Ala Pro Lys Ala Asp
    210                 215                 220

Asn Lys Phe Asn Lys Glu Gln Gln Asn Ala Phe Tyr Glu Ile Leu His
225                 230                 235                 240

Leu Pro Asn Leu Thr Glu Glu Gln Arg Asn Gly Phe Ile Gln Ser Leu
                245                 250                 255
```

-continued

```
Lys Asp Asp Pro Gly Asn Ser
            260

<210> SEQ ID NO 32
<211> LENGTH: 15
<212> TYPE: PRT
<213> ORGANISM: Artificial Sequence
<220> FEATURE:
<223> OTHER INFORMATION: peptide linker sequence

<400> SEQUENCE: 32

Gly Gly Gly Gly Ala Gly Gly Gly Ala Gly Gly Gly Gly Ser
1               5                   10                  15

<210> SEQ ID NO 33
<211> LENGTH: 31
<212> TYPE: PRT
<213> ORGANISM: Artificial sequence
<220> FEATURE:
<223> OTHER INFORMATION: amino acid sequence of TMD23  ( 23 AA
      transmembrane domain of the human lysosomal protein LAMP1)

<400> SEQUENCE: 33

Ser Thr Ala Leu Ile Pro Ile Ala Val Gly Gly Ala Leu Ala Gly Leu
1               5                   10                  15

Val Leu Ile Val Leu Ile Ala Tyr Leu Val Gly Arg Lys Arg Ser
            20                  25                  30

<210> SEQ ID NO 34
<211> LENGTH: 25
<212> TYPE: PRT
<213> ORGANISM: Artificial sequence
<220> FEATURE:
<223> OTHER INFORMATION: amino acid sequence of TMD17  ( 17 AA
      transmembrane domain of the human lysosomal protein LAMP1)

<400> SEQUENCE: 34

Ser Thr Ala Leu Ile Pro Ile Ala Val Gly Gly Ala Leu Ala Gly Leu
1               5                   10                  15

Ala Tyr Leu Val Gly Arg Lys Arg Ser
            20                  25

<210> SEQ ID NO 35
<211> LENGTH: 924
<212> TYPE: DNA
<213> ORGANISM: Artificial sequence
<220> FEATURE:
<223> OTHER INFORMATION: nucleotide sequence encoding  PrtA-TMD17
      optimized to nicotiana tobacum

<400> SEQUENCE: 35
caattgatgg agcaaagaat tacacttaag gaagcatggg atcaaaggaa tggttttata      60
caaagcttaa aggatgatcc tagtcagagc gcgaatgtgc ttggagaagc tcagaaattg     120
aatgattccc aagcaccaaa agccgatgct cagcaaaaca atttcaataa ggatcaacag     180
tccgcattct acgaaattct gaatatgccc aatctcaacg aggctcaaag aacgggttt      240 atccagtctt tgaaagatga cccgtcacaa tctacaaatg ttttaggcga agcaaagaag     300
ctaaatgagt cacaagcccc aaaagcagat aacaacttta caaggagca gcagaacgct     360 ttttacgaga ttctcaatat gcctaatctt aatgaggagc aacgaaacgg ttttatccaa     420
tcccttaaag acgaccctag tcaatcggcc aatttgctta gcgaagctaa aaagcttaac     480
gagtctcaag cacctaaagc ggataacaaa ttcaacaagg aacagcagaa tgcatttttat    540
```

```
gaaatcctgc atctacctaa tctcaatgaa gaacagcgga atgggttcat tcaatcttta    600
aaggacgacc catcacaatc agcaaacttg ctggctgaag ctaagaaact taatgacgca    660
caagctccca aggccgataa caagtttaac aaagaacagc aaaacgcatt ctatgaaatt    720
cttcacttgc caaatttgac tgaggaacag cgcaatggtt tcatacagtc actcaaagat    780
gatccaggaa atagtggtgg tggaggagct gggggtggcg gggctggcgg aggaggttct    840
agtaccgcct tgataccaat tgctgtcgga ggtgctctag ctggattagc ctatcttgtt    900
ggccgtaaaa gatcttaaga gctc                                           924
```

<210> SEQ ID NO 36
<211> LENGTH: 942
<212> TYPE: DNA
<213> ORGANISM: Artificial sequence
<220> FEATURE:
<223> OTHER INFORMATION: nucleotide sequence encoding PrtA-TMD23 optimized to nicotiana tobacum

<400> SEQUENCE: 36

```
caattgatgg agcaaagaat tacacttaag gaagcatggg atcaaaggaa tggttttata    60
caaagcttaa aggatgatcc tagtcagagc gcgaatgtgc ttggagaagc tcagaaattg    120
aatgattccc aagcaccaaa agccgatgct cagcaaaaca atttc

```
ggtactttag gcccacagaa gtggataatc taaagggaga ctcgagcaag gcgaggaatg    360
tttttggttg gaagcccaga gtggggttcg agcaattagt gaagatgagg atgttgagtt    420
agctaaaagg gggatcc                                                   437
```

<210> SEQ ID NO 38
<211> LENGTH: 461
<212> TYPE: DNA
<213> ORGANISM: Artificial Sequence
<220> FEATURE:
<223> OTHER INFORMATION: GMD RNAi oligonucleotide sequence which was
      cloned into pUC18 plasmid

<400> SEQUENCE: 38

```
atcgatccat gggcggccgc aatcatgaat cccctaggcg gggcgagaac ttcgtgaccc     60
ggaagatcac tcgggctgtg gtcggatca aaatcgggct acaaagcaag ctgttcctgg    120
gtaatttgca ggcatccagg gactgggtt ttgccgggga ttacgtggaa gcaatgtgga    180
tgatgctgca gcaagagaag ccggatgact atgtggtggc aacggaggag tcacacacgg    240
tggaggagtt cttggaggtg gcgttcggat acgtaggatt gaattggaag gatcatgtgg    300
tgattgataa gaggtacttt aggcccacag aagtggataa tctaaaggga gactcgagca    360
aggcgaggaa tgttttgggt tggaagccca gagtggggtt cgagcaatta gtgaagatga    420
ggatgttgag ttagctaaaa gggggatccc aattgaatgc t                       461
```

<210> SEQ ID NO 39
<211> LENGTH: 266
<212> TYPE: DNA
<213> ORGANISM: Arabidopsis thaliana
<220> FEATURE:
<221> NAME/KEY: misc_feature
<223> OTHER INFORMATION: XylT intron for GMD RNAi

<400> SEQUENCE: 39

```
tagttaggat ccgaggtttg tgcattttac tcattgatct ggtggatttg aagattgtgt     60
tttggtgaaa agattgcata attggagact tttcattcaa catatgcagc aatgaatcac    120
tgattttgag ctttacattg ttcatattaa ttaggttgtg gttgtgtgag attcttggaa    180
gactatgtag ttatgtgtgg tggttatatc ttgttggttt gatgtttggt ttgcttttg     240 tttggctgca gtggcaattg taacta                                        266
```

<210> SEQ ID NO 40
<211> LENGTH: 642
<212> TYPE: DNA
<213> ORGANISM: Artificial Sequence
<220> FEATURE:
<223> OTHER INFORMATION: nucleic acid sequence encoding XylT Exon3

<400> SEQUENCE: 40

```
ctggcaggac catggatgct aagaacttta gtggcccagt tgtttccgt catgccgccc      60 tctcgccttt gggatatgaa actgccctgt taagggact gtcagaaact atagattgta    120
atggagcttc tgcccatgat tgtggcaaa atcctgatga taagaaaact gcacggttgt    180
ccgagtttgg ggagatgatt agggcagcct ttagatttcc tgtggataga cagaacatcc    240
caaggacagt cacaggccct aatgtcctct tgttagacg tgaggattat ttagctcacc    300
cacgtcatgg tggaaaggta cagtctaggc ttagcaatga agagcaagta tttgattcca    360
taaagagctg ggccttgaac cactcggagt gcaaattaaa tgtaattaac ggattgtttg    420
cccacatgtc catgaaagag caagttcgag caatccaaga tgcttctgtc atagttggtg    480
```

```
ctcatggagc aggtctaact cacatagttt ctgcagcacc aaaagctgta atactagaaa    540
ttataagcag cgaatatagg cgcccccatt ttgctctgat tgcacaatgg aaaggattgg    600
agtaccatcc catatatttg gagggcggc cgcaagtgcg gc                        642
```

```
<210> SEQ ID NO 41
<211> LENGTH: 4
<212> TYPE: PRT
<213> ORGANISM: Artificial sequence
<220> FEATURE:
<223> OTHER INFORMATION: Endoplasmic reticulum targeting sequence

<400> SEQUENCE: 41

Lys Asp Glu Leu
1

<210> SEQ ID NO 42
<211> LENGTH: 6
<212> TYPE: PRT
<213> ORGANISM: Artificial sequence
<220> FEATURE:
<223> OTHER INFORMATION: Endoplasmic reticulum retention motif

<400> SEQUENCE: 42

Ser Glu Lys Asp Glu Leu
1               5

<210> SEQ ID NO 43
<211> LENGTH: 4
<212> TYPE: PRT
<213> ORGANISM: Artificial sequence
<220> FEATURE:
<223> OTHER INFORMATION: Endoplasmic reticulum retention motif

<400> SEQUENCE: 43

His Asp Glu Leu
1

<210> SEQ ID NO 44
<211> LENGTH: 6
<212> TYPE: PRT
<213> ORGANISM: Artificial sequence
<220> FEATURE:
<223> OTHER INFORMATION: N-terminal proline-rich repetitive domain

<400> SEQUENCE: 44

Val His Leu Pro Pro Pro
1               5

<210> SEQ ID NO 45
<211> LENGTH: 6
<212> TYPE: PRT
<213> ORGANISM: Artificial sequence
<220> FEATURE:
<223> OTHER INFORMATION: Assembly and recovery tag for recombinant
      proteins

<400> SEQUENCE: 45

Pro Pro Pro Val His Leu
1               5
```

COMPOSITIONS AND METHODS FOR PRODUCING POLYPEPTIDES WITH A MODIFIED GLYCOSYLATION PATTERN IN PLANT CELLS

CROSS-REFERENCE TO RELATED APPLICATION

The present application is a continuation of U.S. patent application Ser. No. 15/600,193, filed May 19, 2017 (published as 20170283822), which claims priority from and is a continuation of International Application No. PCT/IL2015/051112, filed Nov. 19, 2015, which claims the benefit of U.S. Provisional Application No. 62/082,204, filed Nov. 20, 2014, the contents of each of which are incorporated herein by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 68,335 byte ASCII (text) file named "Seq_List" created on Dec. 5, 2017.

FIELD AND BACKGROUND OF THE INVENTION

The present invention, in some embodiments thereof, relates to compositions and methods for producing polypeptides with a modified glycosylation pattern in plant cells.

Plants have great potential as hosts for the production of mammalian therapeutic proteins including enzymes, growth factors, structural protein such as collagen, chimeric proteins such as Enbrel and multimeric proteins such as antibodies.

The benefits of using plants for the production of recombinant pharmaceuticals include large scale production, reduced costs for production, maintenance and delivery as well as eliminating the risk of the resultant product containing possibly harmful contaminants such as viruses or prions that are pathogenic to humans and other mammals. Plants, like other heterologous expression systems including mammalian cells, bacteria, yeast, and insects, exhibit differences in glycosylation.

In plants, as in other eukaryotes, most of the soluble and membrane bound proteins that are synthesized on polyribosomes associated with the endoplasmic reticulum (ER) are glycoproteins, including those proteins which will later be exported to the Golgi apparatus, lysosomes, plasma membrane or extracellular matrix. The glycans attached to glycoproteins contain a variety of sugar residues linked in linear or branched structures that can assume many different conformations. These glycans can play a fundamental role in promoting correct protein folding and assembly and, as a consequence, enhance protein stability. They may also contain targeting information, or may be directly involved in protein recognition. The three main posttranslational modifications of proteins that involve carbohydrates are N- and O-linked glycosylation and the insertion of glycosyl phosphatidyl inositol anchors.

The N-linked glycosylation mechanisms in mammalian and plant systems have been conserved during evolution. However, differences are observed in the final steps of oligosaccharide trimming and glycan modification in the Golgi apparatus. In contrast to bacteria, having no N-linked glycans, and yeast, having polymannose glycans, plants produce glycoprotein multimers with complex N-linked glycans having a core substituted by two N-acetylglucosamine (GlcNAc) residues. These glycoprotein multimers are also observed in mammals. See, for example, Kornfeld and Kornfeld, Ann. Rev. Biochem. 54:631 (1985). Plant and animal glycopolypeptide multimers contain different terminal carbohydrates that are directly linked to the outer branches of the oligosaccharides present. Animal glycopolypeptide multimers, including mammalian glycopolypeptide multimers, have sialic acid present as a terminal carbohydrate residue, while plant glycopolypeptide multimers do not. The terminal core is substituted by β 1,2-linked xylose (Xyl) and a 1,3-linked core fucose (Fuc) instead of a 1,6-linked core fucose as occur in mammals. Furthermore, plant glycoproteins lack the characteristic galactose (Gal)- and sialic acid-containing complex N-glycans (N-acetyl-neuraminic-α-2-6/3Gal β 1-4) found in mammals.

Plant-derived recombinant proteins hold a risk of severe immunogenicity due to the presence of the foreign sugar residues, i.e., α-1,3 fucose and β-1,2 xylose residues. In order to reduce immunogenicity, a number of platform technologies have been developed, some are described in Naoko Yamane-Ohnuki and Mitsuo Satoh MAbs. 2009 May-June; 1(3): 230-236, Strasser et al., Plant Biotechnology Journal (2008) 6, pp. 392-402; Matsuo et al., Journal of Bioscience and Bioengineering (2014) 118, 4, pp. 448-454; Matsuo Plant Biotechnol. J., 9, 264-281 (2011), as well as in US 20030159178, US 20120079627, 20070089201 and WO 01/29242.

SUMMARY OF THE INVENTION

According to an aspect of some embodiments of the present invention there is provided a method of modifying a glycosylation pattern of a polypeptide-of-interest in a plant or plant cell, the method comprising expressing in a plant or plant cell transformed to express at least one glycosidase in a subcellular compartment, a nucleic acid sequence encoding the polypeptide-of-interest, such that the at least one glycosidase and the polypeptide-of-interest are co-localized to the subcellular compartment of the plant or plant cell, thereby modifying the glycosylation pattern of the polypeptide-of-interest in the plant or plant cell.

According to an aspect of some embodiments of the present invention there is provided a method of producing a polypeptide-of-interest, the method comprising:
(a) expressing in a plant or plant cell transformed to express at least one glycosidase in a subcellular compartment, a nucleic acid sequence encoding the polypeptide-of-interest, such that the at least one glycosidase and the polypeptide-of-interest are co-localized to the subcellular compartment of the plant or plant cell; and subsequently
(b) isolating the polypeptide-of-interest.

According to some embodiments of the invention, the plant or plant cell transformed to express at least one glycosidase in the subcellular compartment further comprises reduced level or activity of at least one glycosyl transferase as compared to a plant or plant cell of the same species expressing wild-type levels or exhibiting wild-type activity of the at least one glycosyl transferase.

According to some embodiments of the invention, the glycosyl transferase comprises Beta-(1-2)-xylosyltransferase and/or Alpha-(1, 3)-fucosyltransferase.

According to some embodiments of the invention, the plant or plant cell transformed to express at least one glycosidase in the subcellular compartment further comprises a nucleic acid sequence encoding a fusion polypeptide comprising a cell wall binding peptide translationally fused to an affinity moiety for binding the polypeptide of interest.

According to an aspect of some embodiments of the present invention there is provided an isolated polypeptide comprising a cell wall binding peptide translationally fused to a heterologous affinity moiety.

According to some embodiments of the invention, the cell wall binding peptide is a cellulose binding domain (CBD).

According to some embodiments of the invention, the affinity moiety is for binding an antibody.

According to some embodiments of the invention, the affinity moiety is for binding an enzyme growth factor or structural protein.

According to some embodiments of the invention, the affinity moiety for binding the antibody comprises protein A/G/L.

According to some embodiments of the invention, the isolated polypeptide is as set forth in SEQ ID NO: 10.

According to an aspect of some embodiments of the present invention there is provided an isolated polynucleotide comprising a nucleic acid sequence encoding the polypeptide.

According to some embodiments of the invention, the isolated polynucleotide is as set forth in SEQ ID NO: 9.

According to an aspect of some embodiments of the present invention there is provided a nucleic acid construct comprising the isolated polynucleotide and a cis-acting regulatory element for directing expression of the polypeptide in a plant cell.

According to some embodiments of the invention, the nucleic acid construct comprises an additional nucleic acid sequence encoding at least one glycosidase.

According to an aspect of some embodiments of the present invention there is provided a transgenic plant or plant cell comprising the polynucleotide of nucleic acid construct described herein.

According to some embodiments of the invention, the transgenic plant or plant cell is transformed to express as least one glycosidase in a subcellular compartment.

According to some embodiments of the invention, the transgenic plant of plant cell comprises reduced level or activity of at least one glycosyl transferase as compared to a plant or plant cell of the same species expressing wild-type levels or exhibiting wild-type activity of the at least one glycosyl transferase.

According to some embodiments of the invention, the glycosyl transferase comprises Beta-(1-2)-xylosyltransferase and/or Alpha-(1, 3)-fucosyltransferase.

According to an aspect of some embodiments of the present invention there is provided a method of producing a transgenic plant or plant cell, the method comprising expressing in the plant or plant cell at least two glycosidases such that the at least two glycosidases are co-localized to a subcellular compartment of the plant or plant cell.

According to some embodiments of the invention, the expressing the at least two glycosidases comprises:
(a) expressing a first glycosidase of the at least two glycosidases in the subcellular compartment of a first plant;
(b) expressing a second glycosidase of the at least two glycosidases in the subcellular compartment of a second plant; and
(c) crossing the first plant and the second plant.

According to some embodiments of the invention, the expressing the at least two glycosidases comprises:
(i) introducing into the plant or plant cell a nucleic acid construct comprising a nucleic acid sequence encoding the at least two glycosidases, wherein each of the at least two glycosidases is translationally fused to a signal peptide for co-localization in the subcellular compartment of the plant or plant cell; or
(ii) introducing into the plant or plant cell a nucleic acid construct system comprising:
a first nucleic acid construct comprising a nucleic acid sequence encoding a first glycosidase;
a second nucleic acid construct comprising a nucleic acid sequence encoding a second glycosidase,
wherein each of the first glycosidase and the second glycosidase is translationally fused to a signal peptide for co-localization in the subcellular compartment of the plant or plant cell.

According to an aspect of some embodiments of the present invention there is provided a method of producing a transgenic plant or plant cell, the method comprising expressing in the plant or plant cell at least one glycosidase and an affinity moiety to a polypeptide-of-interest, wherein the affinity moiety is translationally fused to a cell wall binding peptide.

According to an aspect of some embodiments of the present invention there is provided a nucleic acid construct system comprising:
(i) a first nucleic acid construct comprising a nucleic acid sequence encoding at least one glycosidase;
(ii) a second nucleic acid construct comprising a nucleic acid sequence encoding an affinity moiety to a polypeptide-of-interest,
wherein the affinity moiety is translationally fused to a cell wall binding peptide.

According to some embodiments of the invention, the expressing the nucleic acid sequence encoding the polypeptide-of-interest comprises crossing:
(i) a first transgenic plant transformed to express the at least one glycosidase; and
(ii) a second transgenic plant transformed to express the polypeptide of interest.

According to some embodiments of the invention, the first plant is transformed to express an affinity moiety translationally fused to a cell wall binding peptide, wherein the affinity moiety is for binding the polypeptide of interest.

According to an aspect of some embodiments of the present invention there is provided a nucleic acid construct comprising a nucleic acid sequence encoding at least two glycosidases, wherein each of the at least two glycosidases is translationally fused to a signal peptide for co-localization in a subcellular compartment of a plant or plant cell.

According to an aspect of some embodiments of the present invention there is provided a nucleic acid construct system comprising:
(i) a first nucleic acid construct comprising a nucleic acid sequence encoding a first glycosidase of at least two glycosidases;
(ii) a second nucleic acid construct comprising a nucleic acid sequence encoding a second glycosidase of the at least two glycosidases,
wherein each of the first glycosidase and the second glycosidase is translationally fused to a signal peptide for co-localization in a subcellular compartment of a plant or plant cell.

According to some embodiments of the invention, the signal peptide is a vacuolar signal peptide or an apoplast signal peptide.

According to some embodiments of the invention, the signal peptide is a vacuolar signal peptide or an apoplast signal peptide fused at an N-terminus of the first glycosidase and the second glycosidase.

According to an aspect of some embodiments of the present invention there is provided a transgenic plant or plant cell transformed to express at least two glycosidases in a subcellular compartment in a co-localized manner.

According to an aspect of some embodiments of the present invention there is provided a nucleic acid construct comprising a nucleic acid sequence encoding a polypeptide of interest and at least one glycosidase, wherein each of the polypeptide of interest and the at least one glycosidase is translationally fused to a signal peptide for co-localization in a subcellular compartment of a plant or plant cell.

According to an aspect of some embodiments of the present invention there is provided a nucleic acid construct system comprising:
(i) a first nucleic acid construct comprising a nucleic acid sequence encoding a polypeptide of interest;
(ii) a second nucleic acid construct comprising a nucleic acid sequence encoding and at least one glycosidase,
wherein each of the at least one glycosidase is translationally fused to a signal peptide for co-localization in a subcellular compartment of a plant or plant cell.

According to an aspect of some embodiments of the present invention there is provided a nucleic acid construct comprising a nucleic acid sequence encoding a glycosidase translationally fused to a signal peptide for localization in a subcellular compartment of interest.

According to an aspect of some embodiments of the present invention there is provided an isolated polypeptide comprising an amino acid sequence of a protein A/G/L translationally fused to a heterologous transmembrane domain.

According to some embodiments of the invention, the translationally fused is via a linker.

According to an aspect of some embodiments of the present invention there is provided an isolated polynucleotide comprising a nucleic acid sequence encoding the polypeptide.

According to an aspect of some embodiments of the present invention there is provided a transgenic plant or plant cell comprising the nucleic acid construct as described herein.

According to an aspect of some embodiments of the present invention there is provided a method of modifying a glycosylation pattern of a polypeptide-of-interest in a plant or plant cell, the method comprising introducing into a plant or plant cell the nucleic acid construct or the nucleic acid construct system as described herein, thereby modifying the glycosylation pattern of the polypeptide-of-interest in the plant or plant cell.

According to an aspect of some embodiments of the present invention there is provided a method of producing a polypeptide-of-interest, the method comprising:
(a) introducing into a plant or plant cell the nucleic acid construct or the nucleic acid construct system as described herein; and subsequently
(b) isolating the polypeptide-of-interest.

According to an aspect of some embodiments of the present invention there is provided a transgenic plant or plant cell recombinantly expressing:
(i) a polypeptide of interest; and
(ii) at least one glycosidase
wherein each of the polypeptide of interest and the at least one glycosidase is translationally fused to a signal peptide for co-localization in a subcellular compartment of the plant or plant cell.

According to an aspect of some embodiments of the present invention there is provided a transgenic plant or plant cell comprising the nucleic acid construct or nucleic acid construct system as described herein.

According to some embodiments of the invention, the at least two glycosidases comprise a fucosidase and a xylosidase.

According to some embodiments of the invention, the at least one glycosidase is selected from the group consisting of a fucosidase and a xylosidase.

According to some embodiments of the invention, the subcellular compartment is selected from the group consisting of a vacuole, an apoplast, an endoplasmic reticulum and golgi.

According to some embodiments of the invention, the subcellular compartment is a vacuole.

According to some embodiments of the invention, the plant or plant cell is a tobacco plant or plant cell.

According to some embodiments of the invention, the plant cell is a root cell.

According to some embodiments of the invention, the signal peptide is selected from the group consisting of a vacuolar targeting signal, an endoplasmic targeting signal, an apoplast targeting signal, a mitochondria targeting signal and a plastid targeting signal.

According to some embodiments of the invention, the plant or plant cell transformed to express at least one glycosidase in the subcellular compartment, is further transformed to express an additional glycosidase in the subcellular compartment.

According to some embodiments of the invention, the signal peptide is translationally fused at a C-terminus of the polypeptide of interest or the glycosidase.

According to an aspect of some embodiments of the present invention there is provided an isolated polypeptide produced according to the method described herein.

According to an aspect of some embodiments of the present invention there is provided a nucleic acid construct comprising a nucleic acid sequence encoding a glycosidase translationally fused to a signal peptide for localization in a subcellular compartment of interest.

According to an aspect of some embodiments of the present invention there is provided a transgenic plant or plant cell comprising the nucleic acid construct as described herein.

According to some embodiments of the invention, the polypeptide-of interest is a human polypeptide.

According to some embodiments of the invention, the polypeptide-of interest is a pharmaceutical.

According to some embodiments of the invention, the polypeptide-of interest is selected from the group consisting of an antibody, a vaccine, an enzyme, a growth factor, a hormone and a structural protein.

According to some embodiments of the invention, the polypeptide-of interest is an antibody or an antibody fragment.

According to some embodiments of the invention, the antibody is bevacizumab or adalimumab.

According to an aspect of some embodiments of the present invention there is provided a seed of the transgenic plant described herein.

According to some embodiments of the invention, the seed is a hybrid seed.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A—The DNA fragments encoding the heavy and light chains of the mAbs (SEQ ID NOs: 1, 3, 5 and 7) and pUC18 plasmid bearing the Rubisco-vac expression cassette were restricted by MunI and NotI. FIG. 1B—Four different pUC18 plasmids were created: pUC18 Rb-Humira heavy chain, pUC18 Rb-Humira light chain, pUC18 Rb-Avastin heavy chain and pUC18 Rb-Avastin light chain.

FIG. 2A—Rubisco-vac cassette with the Humira light chain was cloned to pBINPLUS vector with HindIII restriction enzymes. FIG. 2B—Rubisco-vac cassette with the heavy chain of Humira was cloned to pBINPLUS Rb-Humira light chain vector with EcoRI and SacI enzymes. FIG. 2C—the final construct of pBINPLUS Humira.

FIG. 3A—Rubisco-vac cassette with the Avastin heavy chain was cloned to pBINPLUS vector with HindIII restriction enzymes. FIG. 3B—Rubisco-vac cassette with the light chain of Avastin was cloned to pBINPLUS Rb-Avasin heavy chain vector with EcoRI and SacI enzymes. FIG. 3C—the final construct of pBINPLUS Avastin.

FIGS. 5A-C are schematic illustrations showing cloning of CBD-PrtA (SEQ ID NO: 9) into pBINPLUS plasmid. FIG. 5A—DNA including 35S promoter, a coding region of vacuole signal, CBD and proteinA and Nos terminator was cloned to pUC18 plasmid. FIG. 5B—35S cassette with CBD-PrtA was cloned to pBINPLUS plasmid by EcoRI and pBINPLUS CBD-PrtA was created (FIG. 5C).

FIG. 6A—DNA encoding xylosidase (2344 bp, SEQ ID NO: 11) or fucosidase (1564 bp, SEQ ID NO: 13) was restricted by MunI and NotI and cloned into 35S cassette after CBD-PrtA was cut out by the same enzymes. FIG. 6B—Xylosidase or Fucosidase in 35S cassette was cloned in pBINPLUS vector using SdaI and SacI restriction enzymes. FIG. 6C—Two plasmids were constructed: pBINPLUS Xylosidase (15496 bp) and pBINPLUS Fucosidase (14716 bp).

FIG. 7A shows screening recombinant tobacco by Western blot with anti-CBD antibody. FIG. 7B—shows a Slot blot: the amount of commercial Humira is indicated was added to the pellet from 100 mg of WT and CBD-PrtA expressing tobacco tissue. After the pellet was incubated and washed for several times, the antibody was eluted by a mild acid and applied on the nitrocellulose membrane. The mAb was detected by anti-human IgG-AP.

FIG. 8 is a bar graph showing glycosidases activity measured in tobacco plants expressing the Fucosidase (left side) and Xylosidase (right side). The product of the enzymatic reaction (4-methylumbelliferone) was measured at pH 10. Released 4-methylumbelliferone is measured using an excitation wavelength of 355 nm with emission at 460 nm.

FIG. 9 is an image showing stable expression and purification of adalimumab expressed in the apoplast of tobacco plant.

FIG. 10 is a graph showing TNF-binding by adalimumab which was expressed in the apoplast of tobacco plant and purified therefrom, as tested by ELISA assay.

FIGS. 12A-D are schemes and purification results using a Transmembrane bound protein A expressed on the cell membrane of cells expressing the polypeptide of interest of some embodiments of the invention.

FIG. 13 shows xylose and fucose excision of plant derived Adalimumab. Abbreviation: 2 h, 3 h and 4 h—treatment length in hours (2, 3 and 4 hours respectively); N—not treated Adalimumab; C—commercial Humira. 3 different sets of antibodies: Anti-Xylose, Anti-Fucose and Anti-Human IgG were used for detection.

FIG. 14 shows a Western blot performed with anti-Human IgG showing bands at approximately 55 KDa corresponding to adalymumab Heavy chain and at approximately 25 KDa corresponding to adalymumab Light chain.

FIG. 15 shows the results of an ELISA assay for the in-vitro bioactivity of plant derived Adalimumab (PDA) performed on TNF-α pre-coated ELISA plates that were incubated with plant derived adalimumab from 3 (1-3) different transgenic tobacco plant lines. Binding of the mAb to the target was then detected by using anti-human IgG-HRP. PDA average concentration shown in ng (mAb)/mg (fresh leaves).

FIG. 16 shows a TNFa neutralization using PDA as compared to Commercial Humira (shown in circles, Test Reference) VS. Plant derived adalimumab (shown in squares, Test Item) bioactivity of neutralization of rhTNF-α was tested in L929 cell line.

FIG. 17A—anti protein A staining; FIG. 17B—anti human IgG staining of pellet; FIG. 17C—anti human IgG staining of soluble fraction. Com—commercial Humira control; PDA—plant derived adalimumab. Sample preparation was made in 2 different buffers: Binding buffer and Grinding buffer.

FIGS. 18A-D show the cloning of GMD RNAi into pUC18 plasmid. FIG. 18A—pUC18 plasmid containing 35S promotor, Cell signal peptide, gene insert that will be replaced by GMD RNAi encoding DNA and Nos terminator; FIG. 18B—Step 1: GMD anti-sense encoding DNA (423 bp) was inserted by restriction with NotI and BamHI; FIG. 18C—Step 2: β-Xylose Transferase (XylT) intron encoding DNA (242 bp) was inserted by restriction with BamHI and MfeI; FIG. 18D—Step 3: GMD sense encoding DNA (442 bp) was inserted by restriction with MfeI and NcoI.

FIGS. 19A-B show the cloning of the GMD RNAi. FIG. 19A. pBINPLUS vector; 35S GMD RNAi cassette (1747 bp) was cloned using HindII and SacI restriction enzymes to form FIG. 19B. pBIN 35S GMD RNAi plasmid (14094 bp).

FIG. 20A, pUC18 plasmid RUBISCO promotor, Cell signal peptide, Adalimumab Heavy Chain encoding DNA and RUBISCO terminator; FIG. 20B, Replacing Adalimumab Heavy Chain encoding DNA (1362 bp) with XylT (617 bp) by NcoI and NotI restriction enzymes; FIG. 20C, pBINPLUS plasmid; FIG. 20D, RUBISCO XylT cassette (2569 bp) was cloned in pBINPLUS vector using HindII restriction enzyme to form pBINPLUS RUBISCO XylT plasmid (14965 bp).

DESCRIPTION OF SPECIFIC EMBODIMENTS OF THE INVENTION

Figure 1B:
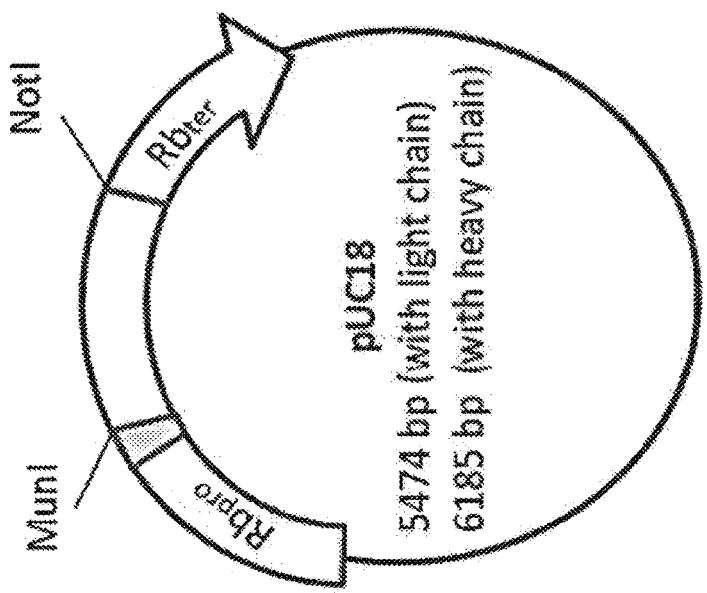
FIGS. 1A-B are schematic illustrations showing cloning of the light and heavy chains of Avastin and Humira in the Rubisco-vac cassette in pUC18 vector.

The present invention, in some embodiments thereof, relates to compositions and methods for producing polypeptides with a modified glycosylation pattern in plant cells.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Plants are attractive hosts for the production of recombinant pharmaceuticals by avoiding the risk of animal-derived viral infection and cost-effectiveness of biopharmaceutical production. Higher plants have similar N-glycosylation pathways compared to mammals, and mainly generate complex-type glycans. with an α-1,3 fucose residue attached to the innermost GlcNAc, a β-1,2 xylose residue attached to the junction mannose of the tri-mannosyl core, neither of which is found in humans. The immunogenicity of the non-human glycosylation, α-1,3 fucosylation and β-1,2 xylosylation, is of concern to regulatory authorities.

Hence, an industrially applicable protein production process that provides consistent yields of fully non-fucosylated and/or non-xylosylated protein therapeutics with fixed quality has become a key goal in the successful development of next-generation therapeutic agents.

The present inventors now offer a novel platform for protein production in plant cells in which the recombinant polypeptide of interest is expressed such that it co-localizes with at least one glycosidase to a subcellular compartment of the plant cell. The polypeptide thus produced carries no α-1,3 fucose or β-1,2 xylose on N-glycans. The process is simple and cost-effective since, it does not require post production processing by exposing the expressed polypeptide to in vitro enzymatic processing. A further advantage of this process is in its directed nature, that is, the plant's glycosylation machinery is unaffected and hence the plants vigor and viability are uncompromised.

As is illustrated hereinbelow and in the Examples section which follows, the present inventors have implemented this platform for the production of two FDA-approved monoclonal antibodies, Avastin® (bevacizumab) and Humira® (adalimumab). The present inventors have co-expressed these antibodies in the vacuole or apoplast of tobacco to-colocalize with recombinantly expressed xylosidase and fucosidase and showed elevated levels of glycosidase activity in these plants.

Specifically, quantification of apoplast targeted adalimumab, also referred to herein as a specific configuration plant-derived Adalimumab (PDA) as assayed by ELISA showed that 4.9 mg PDA/kg leaves was obtained. Both heavy and light chain antibody subunits were detected by Western Blotting (WB), and at the correct ratio. The plants were F1 generation of the transformed plant, and it is expected that the yields are substantially increased by homozygotization.

CBD-Protein A based purification of plant derived Adalimumab from a double transgenic plant expressing both proteins was proven to be feasible. Suitable reaction conditions were found in which both CBD binds cellulose and protein A binds the antibody Fc region. The antibody is therefore effectively maintained in cellulose containing the insoluble fraction immediately after the plant tissue grinding stage. Binding is strong enough to allow washing of the insoluble fraction bound protein without losses.

Expression of recombinant fucosidase and Xylosidase successfully removed the xylose and Fucose residues from the recombinant antibody e.g., Adalimumab. Increased reduction of Fuc and Xyl concentration was observed when both Xylosidase and fucosidase were applied together.

Overall, no significant difference was detected between the test (adalimumab) and reference (Humira) antibodies. The adalimumab activity assay showed that up to a concentration of 62.5 ng/ml, cells protected by Humira were slightly more viable than cells protected with PDA (not significant). When the concentration was further elevated to 125 and afterwards to 250 ng/ml the plant adalimumab appeared to give better results.

Thus according to as aspect of the invention there is provided a method of modifying a glycosylation pattern of a polypeptide-of-interest in a plant or plant cell, the method comprising expressing in a plant or plant cell transformed to express at least one glycosidase in a subcellular compartment, a nucleic acid sequence encoding the polypeptide-of-interest, such that said at least one glycosidase and the polypeptide-of-interest are co-localized to said subcellular compartment of the plant or plant cell, thereby modifying the glycosylation pattern of the polypeptide-of-interest in the plant or plant cell.

As used herein the term "modifying" refers to changing the native post-translational (in-vivo) glycosylation of a polypeptide as compared to same when expressed in a plant cell which comprises a wild-type glycosylation pathway.

According to a specific embodiment, modifying refers to a reduced or complete elimination of at least one glycoside species, e.g., β-1,2-linked xylose (Xyl) or α-1,3-linked core fucose (Fuc). Reduced glycoside species refers to at least 10%, 20%, 30%, 40%, 50%, 60%, 70%, 80%, 90% or even 100% (i.e., complete elimination) of the glycoside species from the polypeptide of interest following in vivo expression as described herein.

As used herein, the term "glycoside" refers to any compound containing a carbohydrate molecule (sugar), particularly any such natural product in plants, convertible by hydrolytic cleavage, into a sugar and a non-sugar component.

According to a specific embodiment, the glycoside comprises β-1,2-linked xylose (Xyl) or α-1,3-linked core fucose (Fuc).

Thus according to a specific embodiment, modifying the glycosylation pattern results in a polypeptide which lacks Fuc or Xyl, also termed as unfucosylated or unxylosylated polypeptide, respectively.

According to another specific embodiment, modifying the glycosylation pattern results in a polypeptide which lacks Fuc and Xyl, also termed as unfucosylated and unxylosylated polypeptide, respectively.

According to another embodiment, modifying may also comprise the post-translation processing of the polypeptide to include glycoside species which are absent from plant cells such as characteristic galactose (Gal)- and sialic acid-containing complex N-glycans (N-acetylneuraminic-α-2-6/3Gal β 1-4).

A "glycosylation pattern" refers to a single (e.g., Fuc) or a plurality of glycoside species (e.g., Fuc, Xyl and optionally sialic acid or galactose) and their relative abundance on the polypeptide or preparation thereof.

The term "plant" as used herein encompasses whole plants, ancestors and progeny of the plants and plant parts, including seeds, shoots, stems, roots (including tubers and root stocks), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees. Alternatively algae and other non-Viridiplantae can be used for the methods of some embodiments of the invention.

According to a specific embodiment the plant or plant cell is a tobacco plant or plant cell (e.g., *N. tabacum* and *N. benthemiana*).

According to a specific embodiment the plant cell is a root cell such as selected from the group consisting of *Agrobacterium rihzogenes* transformed root cell, celery cell, ginger cell, horseradish cell and carrot cell.

According to a specific embodiment the plant or plant cell is a duckweed plant or plant cell (e.g., *lemna*).

According to other specific embodiments, the plant or plant cell is of a, maize, alfalfa, *Arabidopsis*, tomato, collard, lettuce, tobacco, soybean, rice and potato.

As used herein the term "glycosidase" refers to an enzyme which cleaves 0, S or N-linked glycosyl compounds e.g., E.C. 3.2.1 e.g., mannosidase, fucosidase and xylosidase.

The enzyme may be naturally occurring (e.g., plant, bacterial or fungal) or synthetic.

As used herein the term "fucosidase" refers to EC 3.2.1.111 1,3-α-L-fucosidase.

According to a specific embodiment, the alpha-1,3/4-fucosidase [*Streptomyces* sp.] is Sequence ID: gb|AAD10477.1| (SEQ ID NOs: 13,14).

As used herein the term "xylosidase" refers to Beta (1-2) Xylosidase (®-D-xylanxylohydrolase, EC 3.2.1.37) cleaves xylose linked β (1-2). According to a specific embodiment, the enzyme is exo-1,4-beta-xylosidase xlnD [*Aspergillus niger* CBS 513.88] Sequence ID: ref|XP_001389416.1| (SEQ ID NO: 11,12).

According to a specific embodiment, the plant cell is transformed with the at least one glycosidase (e.g., at least two glycosidase i.e., non-identical, wherein each glycosidase is directed at a different glycosyl compound e.g., α-1,3 Fuc and β-1,2 Xyl).

Thus, according to an aspect of the invention, there is provided a method of producing a transgenic plant or plant cell, the method comprising expressing in the plant or plant cell at least one glycosidase in a subcellular compartment or at least two glycosidases, in the latter case the at least two glycosidases are co-localized to a subcellular compartment of the plant or plant cell.

As used herein the term "subcellular compartment of a plant cell" refers to any compartmentalized region of the cell in which the polypeptide of interest can accumulate, such as, as an end product. According to a specific embodiment, the subcellular compartment is of the endomembrane system. Examples of subcellular compartments include, but are not limited to, the vacuole, apoplast, endoplasmic reticulum (ER), golgi, protein bodies derived from the ER and the vacuole, as well as oil bodies. According to a specific embodiment, the proteins are accumulated in the subcellular organelle following (e.g., apoplast, oil bodies) or concomitantly (e.g., ER, golgi and vacuole) with post-translational processing (i.e., glycosylation).

Of note, the selection of the sub-cellular compartment will much depend on the type of polypeptide and activity of the end-product.

For example, human collagen production in plant cells requires hydroxylation on prolines by the human enzyme, to ensure activity of the end product. WO2006/035442 teaches co-expression of the collagen and prolyl-4-hydroxylase (P4H) in a subcellular compartment such as the vacuole or apoplast. In such a case, the glycosidase (e.g., fucosidase and/or xylosidase) is expressed in the vacuole or apoplast as well, to ensure co-localization with the expressed collagen.

In an alternative example, mannose-terminated glycans are thought to be the dominant complex glycans of vacuolar glycoproteins and are considered pertinent for the activity of lysosomal proteins facilitating improved uptake and lysosomal delivery of the proteins administered to the patients (see e.g., WO2004/096978). In such a case the glycosidase (e.g., fucosidase and/or xylosidase) is expressed in the vacuole as well, to ensure co-localization with the expressed polypeptide (e.g., high mannose protein, e.g., lysosomal protein).

According to a specific embodiment, accumulation of the glycosidase (and the polypeptide of interest, hereinafter "the proteins") in a subcellular compartment is achieved by the inclusion of a signal sequence for targeting the expressed protein to a subcellular compartment such as the vacuole, endoplasmic reticulum, golgi, mitochondria and apoplast.

A signal peptide, signal sequence, localization sequence or a sorting sequence (all interchangeably used) is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

According to a specific embodiment the signal sequence is heterologous to the protein.

As used herein "translational fusion" refers to an in-frame fusion of the nucleic acid sequence(s) encoding the targeting sequence and the nucleic acid sequence encoding the protein (i.e., glycosidase or the polypeptide-of-interest) such that a single polypeptide is expressed which comprises both the targeting sequence(s) as well as the protein. The in-frame fusion may be a direct fusion or via a linker (i.e., a nucleic acid sequence encoding an amino acid linker). The linker and/or the signal peptide may be cleavable.

According to a specific embodiment, the proteins (e.g., glycosidase(s) and polypeptide of interest) are expressed in an endomembrane system, which includes the endoplasmic reticulum (ER), the vacuole, and protein bodies derived from ER or vacuoles.

For expression in the endomembrane system the proteins comprise (by translational fusion) an N-terminal signal peptide which is critical for the entry of secreted proteins and all luminal proteins that are subsequently trafficked to the various endomembrane compartments. N-terminus signal peptides are typically interchangeable. The signal is not a defined sequence but rather a pattern or motif that typically comprises one or more positively charged amino acid residues at the N-terminus, followed by a stretch of 6-12 hydrophobic amino acids and a cleavage site. This signal peptide is typically 20-30 amino acids long. Signal peptide prediction tools and databases are publicly available www (dot)cbs(dot)dtu(dot)dk/services/SignalP/; links cited in www(dot) signalpeptide(dot)de/index.php?m=links) to identify putative signal peptides and the signal peptide cleavage site.

For expression of heterologous proteins, in this case e.g., the polypeptide-of-interest and the glycosidase, plant-specific signal peptides (SPs) are often used. Common plant signal sequences include the signal peptides from tobacco extensin, PR-S, and osmotin, the barley α-amylase SP and the potato patatin SP.

In many cases, the signal peptide from the heterologous protein (e.g., a human polypeptide-of-interest) efficiently targets its protein to the plant ER and is recognized by the plant signal peptidase to create the precise N-terminus of the matural product seen in its native organism, such as human IL-2, interferon-β, and β-casein; fungal phytase; and xylanase. However, it is possible to enhance expression at the subcellular localization of interest by the use of a plant signal peptide.

Accumulation in the ER

A specific protein motif is typically required to retain proteins within the ER. Exemplary sequences include the most widely used motif, KDEL (SEQ ID NO: 41), SEKDEL (SEQ ID NO: 42) or HDEL (SEQ ID NO: 43), all being ER retention motifs. Proteins having C-terminal KDEL or HDEL interact with the KDEL receptor, a transmembrane protein that functions in vesicular trafficking primarily between the ER and the Golgi.

Accumulation in ER-Derived Protein Bodies (PBs)

Proteins directed to the ER may either retain in the ER or bud-off into discrete organelles. Proteins stored in ER-derived PBs versus vacuole-derived PBs differ in their glycan composition (routing through the golgi facilitates processing of high-mannose N-glycans to complex glycans).

Exemplary signals for ER-derived PBs include, the proline-rich N-terminal domain of the γ-zein (maize storage protein), which includes a highly repetitive sequence (VHLPPP (SEQ ID NO: 44)) that forms an amphipathic polyproline helix and is critical for zein protein aggregation at the ER membrane (Kogan et al., 2001, J. Mol. Biol. 312:907-913). Mainieri et al. (2004) Plant Physiol. 136: 3447-3456, demonstrated that the fusion of 89 amino acid residues of γ-zein is sufficient to mediate the assembly of a target protein into PBs. A synthetic sequence consisting of (PPPVHL (SEQ ID NO: 45)) 8 has been developed as a targeting tag (termed Zera®) to facilitate assembly and recovery of recombinant proteins (Torrent et al., 2009 BMC Biology 7, 5).

Accumulation in the Vacuole or Vacuole-Derived Protein Bodies (PBs)

Vacuolar targeting of a protein encoded by a nuclear gene requires dual targeting signals. First, an ER signal sequence (as described above) is required for entry into the endomembrane system. A second signal is active after the protein has progressed through the ER and Golgi network where it is carried in vesicles to the vacuole. Receptors for these sequences allow binding and delivery to the organelle. Vacuolar targeting signals are less tightly defined compared to the N-terminal ER-signal peptides and have been identified at the C-terminus (C-terminal pro-peptide, CTPP; e.g., barley lectin, phaseolin, tobacco chitinase) and the N-terminal region of the "mature" protein (N-terminal pro-peptide, NTPP, located immediately upstream of the ER signal sequence; e.g., sporamin, aleurain) as well as internal domains that direct vacuolar targeting (e.g., phytohemagglutinin, legumin, ricin). The NTPP and CTPP are typically removed by proteases within the vacuole. In some cases (e.g., the A-B plant toxins such as ricin and abrin), the internal vacuolar targeting sequences are also removed within the vacuole as part of protein processing. All three types of vacuolar targeting signals (C, N, and internal) have been shown to be necessary and sufficient to sort model proteins from the default secretion route to the vacuole.

Accumulation in the Apoplast

Secretion is the default pathway of the plant endomembrane system and without addition of specific signals for sorting or retention, the proteins (e.g., at least one glycosidase and polypeptide-of-interest) are secreted to the extracellular space and typically accumulate within the apoplast—the region between the plasma membrane and the cell wall. Since the diffusion through the cell matrix is size delimiting, this strategy is used when the polypeptide of interest is large enough not to diffuse out of the cell wall. Alternatively or additionally the polypeptide-of-interest and optionally the glucosidase is immobilized to the apoplast, or to the cell wall by a heterologous polypeptide expressed in the plant cell comprising a cell wall binding peptide translationally fused to a heterologous affinity moiety.

Accumulation in the Cell Wall

In order to be accumulated in the cell wall each of the polypeptide of interest and the at least one glycosidases may be expressed in translational fusion with a cellulose binding domain pfam00942: CBM_3.

Accumulation in Oil Bodies

Oil bodies are organelles that encompass oils (e.g., triglycerides) in a single layer phospholipid membrane that contains the highly hydrophobic protein oleosin. Heterologous proteins have been expressed as oleosin fusions. Oleosins, low molecular mass (Mr 16-24 kDa) polypeptides, consist of a hydrophobic domain flanked by two hydrophilic domains. Oleosins are initially targeted to the ER membranes although both C- and N-termini remain in the cytosol and the proteins are subsequently transferred to the oil bodies. Thus, the fused polypeptide of interest and glycosidase essentially coats the oil bodies and is positioned on the cytosolic face. To allow post-translational modifications, the targeting the protein of interest and the glycosidase is effected through the endomembrane systems, e.g., with an ER retrieval domain as well, then retrieving the protein onto oil body surfaces through binding with an anti-oleosin single chain antibody (scFv). Thus, the product is trafficked and accumulated within the endomembrane system for post-translational processing, but associates with the oil bodies upon cell breakage, providing the advantages of oil-body-based flotation centrifugation, combining the benefits of both systems.

Specific embodiments of the sorting approaches which can be used in accordance with the present teachings are summarized in Table 1, below.

TABLE 1

| Target Organelle | Location in the protein (e.g., polypeptide of interest and/or glucosidase) | Nature of signal | Signal removed |
|---|---|---|---|
| Endomembrane system (lumen) | N-ter | 1-3 basic aa followed by 6-12 hydrophobic aa | Yes |
| ER retention | C-ter | KDEL (SEQ ID NO: 41); HDEL (SEQ ID NO: 42); SEKDEL (SEQ ID NO: 43) | No |
| Vacuole | N-ter | NPR-consrved domain | Yes |
|  | C-ter | No consensus identified | Yes |
|  | Internal | No consensus identified | Varies |

According to a specific embodiment, for cell wall expression, the barley alpha-amylase signal sequence is used (Rogers, J. C. 1985. Two barley alpha-amylase gene families are regulated differently in aleurone cells. J. Biol. Chem. 260: 3731-3738).

According to a specific embodiment, a signal peptide for apoplast secretion is the cel-1 signal peptide (SEQ ID NO: 21, 22).

Targeting the enzyme to the vacuole is another embodiment. Signal sequences to accomplish this are well known. For example, Raikhel U.S. Pat. No. 5,360,726 shows a vacuole signal sequence as does Warren et al. at U.S. Pat. No. 5,889,174. Vacuolar targeting signals may be present either at the amino-terminal portion, (Holwerda et al., The Plant Cell, 4:307-318 (1992), Nakamura et al., Plant Physiol., 101: 1-5 (1993)), carboxy-terminal portion, or in the internal sequence of the targeted protein. (Tague et al., The Plant Cell, 4:307-318 (1992), Saalbach et al. The Plant Cell, 3:695-708 (1991)). Additionally, amino-terminal sequences in conjunction with carboxy-terminal sequences are responsible for vacuolar targeting of gene products (Shinshi et al. Plant Molec. Biol. 14:357-368 (1990)).

According to a specific embodiment, a signal peptide for vacuolar accumulation is the SP (SEQ ID NO: 20) encoded by SP (SEQ ID NO: 17), SP1 (SEQ ID NO: 18) or SP2 (SEQ ID NO: 19), as described by Wei et al. (2004) Plant Biotechnol. J Fluorescent Screening of Transgenic *Arabidopsis* Seeds without Germination Plant Physiol. June 2004; 135 (2): 709-714. THE paper mentions Cell signal peptide.

In order to optimize product yield, multiple SPs are tested for initial assessment of production strategies. For pharmaceutical applications, precise cleavage of the signal peptide—whether from animal, fungal, or plant sources—is often required and generally confirmed by N-terminal sequencing of the final purified product.

As used herein the term "polypeptide of interest" refers to at least one (e.g., 2, 3, 4, more) recombinant polypeptide which modified glycosylation is of value. Such a polypeptide can be widely employed in research and industrial settings, for example, for production of therapeutics, vaccines, diagnostics, collectively termed as pharmaceuticals and many other applications of interest.

According to a specific embodiment, the polypeptide-of-interest is a multimeric protein e.g., collagen, or antibody (i.e., heavy chain and light chain).

According to a specific embodiment, the polypeptide of interest is a human polypeptide.

According to a specific embodiment, the polypeptide of interest is a naturally-occurring polypeptide.

According to a specific embodiment, the polypeptide of interest is a synthetic polypeptide.

According to a specific embodiment, the polypeptide of interest is a chimeric polypeptide.

The polypeptide of interest may be endogenous or exogenous to the plant cell. The polypeptides may be intracellular polypeptides (e.g., a cytosolic protein), transmembrane polypeptides, or secreted polypeptides.

Exemplary therapeutic proteins that can be produced by employing the subject compositions and methods include but are not limited to human hormones (e.g., insulin, growth hormone, insulin-like growth factor 1, follicle-stimulating hormone, and chorionic gonadotropin), hematopoietic proteins (e.g., erythropoietin, C-CSF, GM-CSF, and IL-11), thrombotic and hematostatic proteins (e.g., tissue plasminogen activator and activated protein C), immunological proteins (e.g., interleukin), antibodies and other enzymes (e.g., deoxyribonuclease I). Exemplary vaccines that can be produced by the subject compositions and methods include but are not limited to vaccines against various influenza viruses (e.g., types A, B and C and the various serotypes for each type such as H5N2, H1N1, H3N2 for type A influenza viruses), HIV, hepatitis viruses (e.g., hepatitis A, B, C or D), Lyme disease, and human papillomavirus (HPV). Examples of heterologously produced protein diagnostics include but are not limited to secretin, thyroid stimulating hormone (TSH), HIV antigens, and hepatitis C antigens.

According to other embodiments, examples of the polypeptide of interest include, but are not limited to cytokines, chemokines, lymphokines, ligands, receptors, hormones, enzymes, structural proteins, antibodies and antibody fragments, and growth factors. Non-limiting examples of receptors include TNF type I receptor, IL-1 receptor type II, IL-1 receptor antagonist, IL-4 receptor and any chemically or genetically modified soluble receptors. Examples of enzymes include acetycholinesterase, lactase, activated protein C, factor VII, collagenase (e.g., marketed by Advance Biofactures Corporation under the name Santyl); agalsidase-beta (e.g., marketed by Genzyme under the name Fabrazyme); dornase-alpha (e.g., marketed by Genentech under the name Pulmozyme); alteplase (e.g., marketed by Genentech under the name Activase); pegylated-asparaginase (e.g., marketed by Enzon under the name Oncaspar); asparaginase (e.g., marketed by Merck under the name Elspar); and imiglucerase (e.g., marketed by Genzyme under the name Ceredase). Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-beta), interferon gamma (IFNgamma), interferon gamma inducing factor I (IGIF), transforming growth factor beta (IGF-beta), RANTES (regulated upon activation, normal T-cell expressed and presumably secreted), macrophage inflammatory proteins (e.g., MIP-1-alpha and MIP-1-beta), Leishmnania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF alpha type II receptor, erythropoietin (EPO), insulin and soluble glycoproteins e.g., gp120 and gp160 glycoproteins. The gp120 glycoprotein is a human immunodeficiency virus (WIV) envelope protein, and the gp160 glycoprotein is a known precursor to the gp120 glycoprotein. Other examples include secretin, nesiritide (human B-type natriuretic peptide (hBNP)) and GYP-I.

Other products may include GPCRs, including, but not limited to Class A Rhodopsin like receptors such as Muscatinic (Muse.) acetylcholine Vertebrate type 1, Musc. acetylcholine Vertebrate type 2, Musc. acetylcholine Vertebrate type 3, Musc. acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykffin, C5a anaphylatoxin, Finet-leu-phe, APJ like, Interleukin-8 type A, Interleukin-8 type B, Interleukin-8 type others, C-C Chemokine type 1 through type 11 and other types, C-X-C Chemokine (types 2 through 6 and others), C-X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR10), Neuropeptide Y (type 1 through 7), Neuropeptide Y, Neuropeptide Y other, Neurotensin, Opioid (type D, K, M, X), Somatostatin (type 1 through 5), Tachykinin (Substance P(NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF, QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory 11 fam 1 through 13), Prostaglandin (prostaglandin E2 subtype EP 1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,11 GPR91, Purinoceptor P2RY5, 8,9,10 GPR35,92,174, Purinoceptor P2RY12-14 GPR87 (JDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas proto-oncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRCS, Orphan GPCR6, Bride of sevenless proteins (BOSS), Taste receptors (TiR), Class D Fungal pheromone, Fungal pheromone A-Factor like (STE2,STE3), Fungal pheromone B like (BAR,BBR,RCB,PRA), Class E cAMP receptors, Ocular albinism proteins, Frizzled/Smoothened family, frizzled Group A (Fz 1&2&4&5&7-9), frizzled Group B (Fz 3 & 6), fizzled Group C (other), Vomeronasal receptors, Nematode chemoreceptors, Insect odorant receptors, and Class Z Archaeal/bacterial/fungal opsins.

Bioactive peptides may also be produced. Examples include: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleulin, denileukin diftitox, interferon alfa-n3 (injection), interferon alfa-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphnmate, octocog alfa, Factor VIII, palifermin, Indikinase, tenecteplase, alteplase, pamiteplase, reteplase, nateplase, monteplase, follitropin alfa, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alfa, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-215, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune iseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, NA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S. pneumonia* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multiepitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In certain embodiments, the heterologously produced protein is an enzyme or biologically active fragments thereof. Suitable enzymes include but are not limited to: oxidoreductases, transferases, hydrolases, lyases, isomerases, and ligases. In certain embodiments, the heterologously produced protein is an enzyme of Enzyme Commission (EC) class 1, for example an enzyme from any of EC 1.1 through 1.21, or 1.97. The enzyme can also be an enzyme from EC class 2, 3, 4, 5, or 6. For example, the enzyme can be selected from any of EC 2.1 through 2.9, EC 3.1 to 3.13, EC 4.1 to 4.6, EC 4.99, EC 5.1 to 5.11, EC 5.99, or EC 6.1-6.6. According to a specific embodiment, the enzyme is a high mannose enzyme such as a lysosomal protein, e.g., glucocerebrosidase and alpha-galactosidase.

As used herein, the term "antibody" refers to a substantially intact antibody molecule. The term refers to a monospecific antibody as well as bi- and tri-specific antibodies.

As used herein, the phrase "antibody fragment" refers to a functional fragment of an antibody (such as Fab, F(ab')2, Fv or single domain molecules such as VH and VL) that is capable of binding to an epitope of an antigen.

Exemplary antibodies produced in the cells of the present invention include, but are not limited to, abciximab (ReoPro®), adalimumab (Humira®), alemtuzumab (Campath®), basiliximab (Simulect®), bevacizumab (Avastin®), cetuximab (Erbitux®), daclizumab (Zenapax®), dacetuzumab, eculizumab (Soliris®), efalizumab (Raptiva®), Edrecolomab (Panorex®), epratuzumab, ibritumomab (Zevalin®), tiuxetan, infliximab (Remicade®), muromonab-CD3 (OKT3), natalizumab (Tysabri®), omalizumab (Xolair®), palivizumab (Synagis®) panitumumab (Vectibix®), ranibizumab (Lucentis®), gemtuzumab ozogamicin (Mylotarg®), oregovomab (OvaRex®), rituximab (Rituxan®), tositumomab (Bexxar®), trastuzumab (Herceptin®), MetMAb, ocrelizumab, pertuzumab, Raptiva® (efalizumab), hu M195Mab, MDX-210, BEC2, anti-Abeta, anti-CD4, anti-IL-13, anti-oxLDL, trastuzumab-DM1, apomab, rhuMAb beta7, rhuMAb IFNalpha, GA101, anti-OX40L, ipilimumab, Valortim, ustekinumab, golimumab, ofatumumab, zalutumumab, tremelimumab, motavizumab, mitumomab, ecromeximab, ABX-EGF, MDX010, XTL 002, H11 SCFV, 4B5, XTL001, MDX-070, TNX-901, IDEC-114, and any antibody fragments specific for antigens including but not limited to complement C5, CBL, CD147, gp 120, VLA4, CD11a, CD18, VEGF, CD40L, anti-Id, ICAM1, CD2, EGFR, TGF-beta2, TNF-alpha, TNF receptor, E-selectin, FactII, Her2/neu, F gp, CD11/18, CD14, CD80, ICAM3, CD4, CD23, beta.2-integrin, alpha4beta7, CD52, CD22, OX40L, IL-5 receptor, GM-CSF receptor, GM-CSF, HLA-DR, oxLDL, CD64 (FcR), TCR alpha beta, CD3, Hep B, CD 125, DR5, EpCAM, gpIIbIIIa, IgE, beta 7 integrin, CD20, IL1beta, IL-2, IL-4, IL-5, IL-6, IL-8, IL-9, IL10, IL13, IL-12/IL-23, IL-1 5, IFN-alpha, IFN-beta, IFN-gamma, VEGFR-1, platelet-derived growth factor receptor .alpha. (PDGFRalpha), vascular adhesion protein 1 (VAP1), connective tissue growth factor (CTGF), Apo2/TRAIL, CD25, CD33, HLA, F gp, IgE, CTLA-4, IP-10, anti-*C. difficile* Toxin A and Toxin B, *B. anthracis* PA, respiratory syncytial virus (RSV), mannose receptor/hCG.beta, integrin receptors, PD1, PDL-1, CD 19, CD70, and VNR integrin.

Exemplary structural proteins that can be produced according to the present teachings include, but are not limited to collagen, procollagen, albumin, fibrinogen or derivatives of same.

For multimeric protein production is may be desired to express all subunits on a single nucleic acid construct to ensure stoichiometric production. However, expression from a plurality of nucleic acid constructs (construct system) in a single plant cell or a plurality of cells may also be achieved.

The proteins as described herein are encoded by isolated polynucleotide(s) for recombinant expression in plant cells. Each of the open reading frames encoding the proteins (e.g., polypeptide of interest and at least one glycosidase) is translationally fused to a signal peptide such as described above. Although both proteins are targeted to the same subcellular compartment, the signals need not be the same.

The phrase "an isolated polynucleotide" refers to a single or double stranded nucleic acid sequence which is isolated and provided in the form of an RNA sequence (i.e. comprising ribonucleotides), a complementary polynucleotide sequence (cDNA), a genomic polynucleotide sequence (i.e. comprising deoxyribonucleotides) and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Exemplary nucleic acid sequences encoding for the proteins of the invention include, but are not limited to SEQ ID NOs: 2, 4, 6, 8, 10, 12, 14, 20, 30.

For heterologous expression, nucleic acid sequences encoding each of the above-mentioned polypeptides (as well as other polypeptides, such as described further below), are ligated into a nucleic acid construct or construct systems.

As used herein, the qualifier "heterologous" when relating to the proteins of the invention, indicates that the proteins are encoded by a nucleic acid sequence(s) which are foreign to (non-naturally occurring within) the expressing cell.

According to an embodiment of the invention, there is provided a nucleic acid construct comprising a nucleic acid sequence encoding at least two glycosidases, wherein each of the at least two glycosidases is translationally fused to a signal peptide for co-localization in a subcellular compartment of a plant or plant cell.

According to an additional or alternative embodiment of the invention, there is provided a nucleic acid construct system comprising:
(i) a first nucleic acid construct comprising a nucleic acid sequence encoding a first glycosidase of at least two glycosidases;

(ii) a second nucleic acid construct comprising a nucleic acid sequence encoding a second glycosidase of the at least two glycosidases,
wherein each of the first glycosidase and the second glycosidase is translationally fused to a signal peptide for co-localization in a subcellular compartment of a plant or plant cell.

According to an additional or alternative embodiment of the invention, there is provided a nucleic acid construct comprising a nucleic acid sequence encoding a polypeptide of interest and at least one glycosidase, wherein each of the polypeptide of interest and the at least one glycosidase is translationally fused to a signal peptide for co-localization in a subcellular compartment of a plant or plant cell.

According to an additional or alternative embodiment of the invention, there is provided a nucleic acid construct system comprising:
(i) a first nucleic acid construct comprising a nucleic acid sequence encoding a polypeptide of interest (at least one subunit or more, e.g., 2, 3);
(ii) a second nucleic acid construct comprising a nucleic acid sequence encoding and at least one glycosidase,
wherein each of the at least one glycosidase is translationally fused to a signal peptide for co-localization in a subcellular compartment of a plant or plant cell.

According to an additional or alternative embodiment of the invention, there is provided a nucleic acid construct comprising a nucleic acid sequence encoding a glycosidase translationally fused to a signal peptide for localization in a subcellular compartment of interest.

According to a specific embodiment, each of the above mentioned nucleic acid constructs or nucleic acid construct systems, may comprise additional nucleic acid sequences or constructs such as those encoding additional glycosidases, or post-translational modification enzymes which include, but are not limited to, prolyl 4-hydroxylase or a subunit thereof, lysyl oxidase, lysyl hydroxylase, C-proteinase, N-proteinase, PACE, γ-glutamyl carboxylase, N-acetylglucosaminaltransferases, N-acetylgalactosaminyltransferases, N-acetylgalactosaminyltransferases, sialyl-transferases, fucosyltransferases, galactosyltransferases, mannosyltransferases, sulfotransferases, glycosidases, acetyltransferases, and mannosidases, as taught in WO/2001/029242.

Alternatively or additionally to improve the afucosylation and axylosylation, the plant or plant cell may comprise a reduced level or activity of at least one glycosyl transferase such as compared to a plant or plant cell of the same species expressing wild-type levels or exhibiting wild-type activity of said at least one glycosyl transferase.

According to a specific embodiment, the glycosyl transferase comprises Beta-(1-2)-xylosyltransferase and/or Alpha-(1, 3)-fucosyltransferase.

Methods of reducing expression or activity of glycosyl transferases are described in details in WO/2001/029242. Generally methods of suppressing gene expression in plants are well known in the art and include, but are not limited to, siRNA, dsRNA, antisense, hnRNA and chimeric nucleases such as comprising DNA-binding domain of a meganuclease DNA-binding domain, a leucine zipper DNA-binding domain, a transcription activator-like (TAL) DNA-binding domain, a recombinase, a CRISPR-Cas9 and a zinc finger protein DNA-binding domain.

According to a specific embodiment, the target for silencing is GDP-D-mannose 6,6-dehydrase gene(s).

According to a specific embodiment, the target for silencing is Xylose transferase (XylT).

Additional teachings for silencing of gene involved in protein fucosylation/xylosylation can be found in Matsuo et al. 2014 J. Bioscience and Bioengineering 9:264-281.

Alternatively or additionally, the plant is transformed with a polynucleotide, which confers a culturing or agricultural effective trait, e.g insect resistance, disease resistance, herbicide resistance, increased yield, increased tolerance to environmental stress, increased or decreased starch, oil or protein content, for example.

Alternatively or additionally, the plant is transformed with a polynucleotide which simplify the isolation of the polypeptide of interest. According to an embodiment, the plant thus expresses a nucleic acid sequence encoding a fusion polypeptide comprising a cell wall binding domain (e.g., CBD) translationally fused to a (e.g., heterologous, chimeric protein) affinity moiety for binding the polypeptide of interest.

Examples of cellulose binding domains which can be used in accordance with the present teachings are those provided in the Examples section as well as from the following protein sources (see also WO2009/069123):
β-glucanases (avicelases, CMCases, cellodextrinases)
exoglucanses or cellobiohydrolases
cellulose binding proteins
xylanases
mixed xylanases/glucanases
esterases
chitinases
β-1,3-glucanases
β-1,3-(β-1,4)-glucanases
(β-)mannanases
β-glucosidases/galactosidases
cellulose synthases Yet alternatively or additionally, the plant or plant cell may be transformed with a nucleic acid construct comprising a nucleic acid sequence encoding a polypeptide comprising an amino acid sequence having an affinity towards the polypeptide of interest (e.g., in the case of an antibody, protein A/G/L) translationally fused to a heterologous transmembrane domain. Thus following homogenization, the polypeptide of interest may bind the membrane-bound affinity moiety.

The fusion of the affinity moiety to the transmembrane domain may be direct or via a linker (e.g., SEQ ID NO: 31).

Thus, either during culturing (e.g., when the polypeptide of interest and the glycosidase are directed to the apoplast), or following culturing and lysis of the cells, the polypeptide of interest will bind the affinity moiety and will immobilize to the insoluble fraction.

The affinity moiety may be any amino acid sequence which has a specific affinity (and not to plant cell proteins) e.g., above $10^{-4}$ M or $10^{-6}$ M to the polypeptide of interest. According to an exemplary embodiment the affinity moiety is protein A, G or L. According to a specific embodiment, the affinity moiety is protein A.

These expression products may or may not co-localize with the polypeptide of interest.

Constructs useful in the methods according to some embodiments of the invention may be constructed using recombinant DNA technology well known to persons skilled in the art. The nucleic acid constructs, may be proprietary or commercially available, suitable for transforming into plants and suitable for expression of the proteins in the transformed cells. The genetic construct can be an expression vector wherein said nucleic acid sequence is operably linked to one or more regulatory sequences allowing expression in the plant cells.

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Examples of preferred promoters useful for the methods of some embodiments of the invention are presented in Table 2, 3, 4 and 5.

TABLE 2

Exemplary constitutive promoters for use in the performance of some embodiments of the invention

| Gene Source | Expression Pattern | Reference |
| --- | --- | --- |
| Actin | constitutive | McElroy et al., Plant Cell, 2: 163-171, 1990 |
| CAMV 35S | constitutive | Odell et al., Nature, 313: 810-812, 1985 |
| CaMV 19S | constitutive | Nilsson et al., Physiol. Plant 100: 456-462, 1997 |
| GOS2 | constitutive | de Pater et al., Plant J Nov; 2(6): 837-44, 1992 |
| ubiquitin | constitutive | Christensen et al., Plant Mol. Biol. 18: 675-689, 1992 |
| Rice cyclophilin | constitutive | Bucholz et al., Plant Mol Biol. 25(5): 837-43, 1994 |
| Maize H3 histone | constitutive | Lepetit et al., Mol. Gen. Genet. 231: 276-285, 1992 |
| Actin 2 | constitutive | An et al., Plant J. 10(1); 107-121, 1996 |

TABLE 3

Exemplary seed-preferred promoters for use in the performance of some embodiments of the invention

| Gene Source | Expression Pattern | Reference |
| --- | --- | --- |
| Seed specific genes | seed | Simon, et al., Plant Mol. Biol. 5. 191, 1985; Scofield, etal., J. Biol. Chem. 262: 12202, 1987.; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al. Plant Mol Biol, 143). 323-32 1990 |
| napA | seed | Stalberg, et al., Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184, 1997 |
| wheat a, b and g gliadins | endosperm | EMBO3: 1409-15, 1984 |
| Barley ltrl promoter barley B1, C, D hordein | endosperm endosperm | Theor Appl Gen 98: 1253-62, 1999; Plant J 4: 343-55, 1993; Mol Gen Genet 250: 750-60, 1996 |
| Barley DOF | endosperm | Mena et al., The Plant Journal, 116(1): 53-62, 1998 |

TABLE 3-continued

Exemplary seed-preferred promoters for use in the performance of some embodiments of the invention

| Gene Source | Expression Pattern | Reference |
|---|---|---|
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice-globulin Glb-1 | endosperm | Wu et al., Plant Cell Physiology 398) 885-889, 1998 |
| rice OSH1 | emryo | Sato et al., Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorgum gamma-kafirin | endosperm | PMB 32: 1029-35, 1996 |
| KNOX | emryo | Postma-Haarsma et al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, etal., Plant Mol. Biol. 19: 873-876, 1992 |

TABLE 4

Exemplary flower-specific promoters for use in the performance of the invention

| Gene Source | Expression Pattern | Reference |
|---|---|---|
| AtPRP4 | flowers | salus.medium.edu/mmg/tierney/html |
| chalene synthase (chsA) | flowers | Van der Meer, et al., Plant Mol. Biol. 15, 95-109, 1990. |
| LAT52 | anther | Twell et al. Mol. Gen Genet. 217: 240-245 (1989) |
| apetala-3 | flowers | |

TABLE 5

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |

TABLE 5-continued

Alternative rice promoters for use in the performance of the invention

| PRO # | gene | expression |
|---|---|---|
| PR00080 | Metallothioneine-like ML2 | transfer layer of embryo + calli |
| PR00081 | putative caffeoyl-CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 | strong root |
| PR00111 | uclacyanin 3-like protein | weak discrimination center/shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha- globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSHI | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2 short (barley) | |
| PRO0228 | BLZ-2 long (barley) | |

Nucleic acid sequences of the polypeptides (e.g., glycosidase and polypeptide of interest) of some embodiments of the invention may be optimized for plant expression.

Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681).

Thus, some embodiments of the invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Plant cells may be transformed stably or transiently with the nucleic acid constructs of some embodiments of the invention.

The plant cells may be transformed with the nucleic acid sequence (construct or construct system) encoding the at least one glycosidase (e.g., at least two glycosidases) followed by transformation with the nucleic acid construct encoding the polypeptide-of-interest. Alternatively, plant cells may be transformed with the nucleic acid sequence (construct or construct system) encoding the at least one glycosidase (e.g., at least two glycosidases) and the polypeptide-of-interest. Alternatively, plant cells may be transformed with the nucleic acid sequence (construct or construct system) encoding the at least one glycosidase (e.g., at least two glycosidases) following transformation with the nucleic acid construct encoding the polypeptide-of-interest.

In stable transformation, the nucleic acid molecule of some embodiments of the invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants, collectively termed herein as transforming, introducing, infecting (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA (i.e., heterologous) into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by some embodiments of the invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of some embodiments of the invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Thus, according to a specific embodiment, expressing the at least two glycosidases comprises introducing into the plant or plant cell a nucleic acid construct comprising a nucleic acid sequence encoding the at least two glycosidases, wherein each of the at least two glycosidases is translationally fused to a signal peptide for co-localization in the subcellular compartment of the plant or plant cell. The plant or plant cell may be further transformed with the polypeptide of interest. Alternatively or additionally, the plant cell is transformed with the polypeptide of interest and a glycosidase.

Thus, a single plant (whether transgenic or not) is transformed with nucleic acid construct or construct systems as described herein.

However, as the present teachings, relate to the expression of a plurality of transgenes, the transgenic plants or plant cells can be generated by crossing plants each expressing an individual transgene (or more) so as to obtain a hybrid product which comprises the plurality of transgenes.

Thus, according to a specific embodiment, expressing the transgenes (e.g., two glycosidases, glycosidase and polypeptide of interest or two glycosidases and polypeptide of interest) is effected by the art of crossing and selection.

Thus, expressing the at least two glycosidases comprises:
(a) expressing a first glycosidase of the at least two glycosidases in the subcellular compartment of a first plant;
(b) expressing a second glycosidase of the at least two glycosidases in the subcellular compartment of a second plant; and
(c) crossing the first plant and the second plant.

Alternatively, a first plant expressing at least one glycosidase (e.g., at least two glycosidases) in a subcellular compartment is crossed with a second plant expressing the polypeptide of interest.

Alternatively, a first plant expressing a polypeptide fusion comprising a cell wall binding peptide translationally fused to a heterologous affinity moiety and optionally at least one glycosidase (e.g., at least two glycosidases) in a subcellular compartment is crossed with a second plant expressing the polypeptide of interest.

Each of these plants may further comprise a nucleic acid sequence for downregulating an activity of fucosyl transferase or xylosyl transferase in the plant cell.

Crossing and breeding can be accomplished by any means known in the art for breeding plants such as, for example, cross pollination of the first and second plants that are described above and selection for plants from subsequent generations which express both the first and second enzymes. The plant breeding methods used herein are well known to one skilled in the art. For a discussion of plant breeding techniques, see Poehlman (1987) Breeding Field Crops. AVI Publication Co., Westport Conn. Many crop plants useful in this method are bred through techniques that take advantage of the plant's method of pollination.

According to a specific embodiment, following transformation the plant or plant cell is selected for the highest level of expression of the polypeptide of interest as well as the level/activity of the glycosidase(s), and it is thus useful to ascertain expression levels in transformed plant cells, transgenic plants and tissue specific expression.

One such method is to measure the expression of the polypeptide-of-interest as a percentage of total soluble protein. One standard assay is the Bradford assay which is well known to those skilled in the art (Bradford, M. 1976. Anal. Biochem. 72:248). The biochemical activity of the recombinant protein should also be measured and compared with a wildtype standard. The activity of polysaccharide degrading enzymes, i.e., glycsidases, can be determined by the methods well known in the art such as Fuc-Mu (4-Methylumbelliferyl α-L-fucopyranosidase) and Xyl-Mu (4-Methylumbelliferyl-b-D-xylopyranosidase), for testing fucosidase and xylosidase activity, respectively.

Other assays for glycosidase activity are known in the art and can be used to detect enzyme activity in extracts prepared from callus, leafs, fruits and seeds. See, Coughlan et al. ((1988) J. Biol. Chem. 263:16631-16636) and Freer ((1993) J. Biol. Chem. 268:9337-9342). In addition, western analysis and ELISAs can be used to assess protein integrity and expression levels.

Thus, the present teachings provide for transgenic plants or plant cells e.g., a transgenic plant or plant cell transformed to express at least two glycosidases in a subcellular compartment in a co-localized manner, or a transgenic plant or plant cell transformed to express at one glycosidase (e.g., at least two glycosidases) and a polypeptide of interest in a subcellular compartment in a co-localized manner.

Alternatively or additionally, there is provided a transgenic plant or plant cell comprising the nucleic acid construct or nucleic acid construct system as described herein.

As used herein a transgenic plant or plant cell refers to a plant or plant cell which comprises a heterologous nucleic acid sequence which translates to at least one of glycosidase and a polypeptide of interest.

One transformed the plant cells are cultured or the plants are grown under conditions which are suitable for transgene expression so as to produce the polypeptide of interest.

Thus, according to an aspect of the invention, there is provided a method of producing a polypeptide-of-interest, the method comprising:
(a) expressing in a plant or plant cell transformed to express at least one glycosidase in a subcellular compartment, a nucleic acid sequence encoding the polypeptide-of-interest, such that said at least one glycosidase and the polypeptide-of-interest are co-localized to said subcellular compartment of the plant or plant cell; and subsequently
(b) isolating the polypeptide-of-interest.

Alternatively or additionally, there is provided a method of producing a polypeptide-of-interest, the method comprising:
(a) introducing into a plant or plant cell the nucleic acid constructs as described herein; and subsequently
(b) isolating the polypeptide-of-interest.

Thus, plant cells can be cultured cells, cells in cultured tissue or cultured organs, or cells in a plant. In some embodiments, the plant cells are cultured cells, or cells in cultured tissue or cultured organs. In yet further embodiments, the plant cells are any type of plant that is used in gene transference. The plant cell can be grown as part of a whole plant, or, alternatively, in plant cell culture.

According to some aspects of the invention, the plant cells are grown in a plant cell suspension culture. As used herein, the term "suspension culture" refers to the growth of cells separate from the organism. Suspension culture can be facilitated via use of a liquid medium (a "suspension medium"). Suspension culture can refer to the growth of cells in a three dimensional culture in liquid nutrient media, for example, but not limited to, growth in suspension culture in a bioreactor. Methods and devices suitable for growing plant cells of the invention in plant cell suspension culture are described in detail in, for example, PCT WO2008/135991, U.S. Pat. No. 6,391,683, U.S. patent application Ser. No. 10/784,295; International Patent Publications PCT Nos. WO2004/091475, WO2005/080544 and WO 2006/040761, all of which are hereby incorporated by reference as if fully set forth herein. Also contemplated are hairy root cultures grown in suspension culture, in some embodiments, in bioreactors.

Thus, the invention encompasses plants or plant cultures expressing the nucleic acid sequences, so as to produce the recombinant polypeptide-of-interest. Once expressed within the plant cell or the entire plant, the level of the polypeptide-of-interest encoded by the nucleic acid sequence can be determined by methods well known in the art such as, described hereinabove or well known in the art.

The polypeptide of interest is then isolated from the plant or plant cell. The degree of isolation depends on the sub-cellular compartment as well as the intended use. Typically, a cell extract which comprises the polypeptide of interest is produced. The extract is usually subject to clarification to remove host cell contaminants and culture remnants.

Following clarification, the clarified extract can be further processed, used as is, or stored for future use. According to some embodiments of some aspects of the invention, following extraction and clarification of the extract, the polypeptide-of-interest can be further isolated, also termed as purified. Purification may be carried out by chromatography, for example, ion-exchange, size filtration, HPLC, or ultra-filtration, counter-current dialysis, affinity purification, immune-purification, and the like. Thus, in some embodiments, polypeptide-of-interest is a purified polypeptide, characterized by a purity of at least 85%, at least 87%, at least 90%, at least 91%, at least 91.5%, at least 92%, at least 92.5%, at least 93%, at least 93.1%, at least 93.2%, at least 93.3%, at least 93.4%, at least 93.5%, at least 93.6%, at least 93.7%, at least 93.8%, at least 93.9%, at least 94%, at least 94.5%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, in a range of at least 92.0-99.8%, or at least 95-99%, or at least 97-99%, or at least 98-99.5 or 100% purity. In some embodiments, purity of the polypeptide-of-interest is measured by HPLC.

Purity of the plant expressed polypeptide-of-interest can be expressed as a weight percent of the total, or as the weight percent of impurities. In various embodiments, the cumulative weight percentage of all proteins other than the polypeptide-of-interest in the composition used in the methods of the present invention is less than 10%, 5%, less than 1%, and in some embodiments, less than 0.5%, 0.4%, 0.3%, 0.2%, even in some embodiments less than 0.1%. In particular embodiments, the composition completely lacks host cell proteins other than the polypeptide-of-interest. Thus, as a weight percentage of protein, the compositions administered in the methods of the present invention typically comprise at least 90%, 91%, 92%, 93%, 94%, at least 95%, 96%, 97%, 98%, 99%, and in some embodiments, at least 99.5%, the polypeptide-of-interest or active portion thereof.

In some embodiments the plant-expressed polypeptide-of-interest composition comprises impurities derived from the plant host cell, such as, but not limited to nucleic acids and polynucleotides, amino acids, oligopeptides and polypeptides, glycans and other carbohydrates, lipids and the like. In some embodiments the host-cell derived impurities comprise biologically active molecules, such as enzymes. Host cell proteins can be monitored, for example, by HPLC, using host cell protein-specific antibodies raised against plant cell fractions from polypeptide-of-interest-null plant cells cultured under similar conditions, and other assays known in the art.

The polypeptide is characterized by reduced immunogenicity in human subjects as compared to the same protein produced in a plant system having a wild-type glycosylation system.

The polypeptide thus produced can be used per se or in a pharmaceutical composition where it is mixed with suitable carriers or excipients.

Alternatively, it can be packed in a kit or article of manufacture for research, cosmetic or clinical applications.

It is expected that during the life of a patent maturing from this application many relevant polypeptide-of-interest as well as glycosidases will be developed and the scope of these terms is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning of Avastin (Bevacizumab) and Humira (Adalimumab) to the Binary pBINPLUS Vector for Tobacco Transformation Mediated by *Agrobacterium*

Restriction enzymes were purchased from Thermo Scientific.

For expression in the vacuole, a Rubisco-vac cassette was used comprising the Rubisco promoter (SEQ ID NOs: 26), vacuolar signal peptide (SEQ ID NOs: 17 and 20) and Rubisco terminator (SEQ ID NOs: 27).

I. First, the Commercial Plasmid (pUC57 from Genscript) Bearing Synthetic Genes was Restricted by MunI and NotI Enzymes to Create Four DNA Inserts Coding for: Humira Heavy Chain (SEQ ID NOs: 1 and 2), Humira Light Chain (SEQ ID NOs: 3 and 4), Avastin Heavy Chain (SEQ ID NOs: 5 and 6) and Avastin Light Chain (SEQ ID NOs: 7 and 8).

Figure 1A:
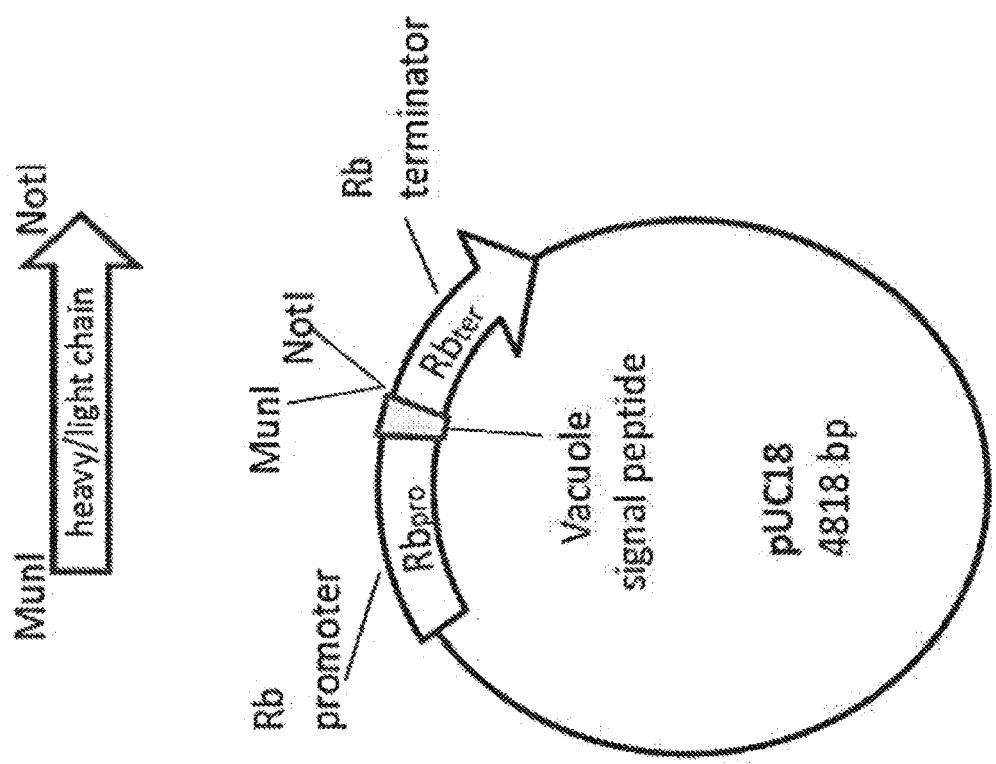

Then the inserts were ligated into the pUC18 plasmid containing Rubisco-vac cassette also restricted by MunI and NotI (FIGS. 1A-B) to create four different constructs: pUC18 Rb-Humira heavy chain, pUC18 Rb-Humira light chain, pUC18 Rb-Avastin heavy chain and pUC18 Rb-Avastin light chain, where vacuolar targeting signal is positioned N-terminally to the coding sequence (SEQ ID NO: 17).

Figure 2A:
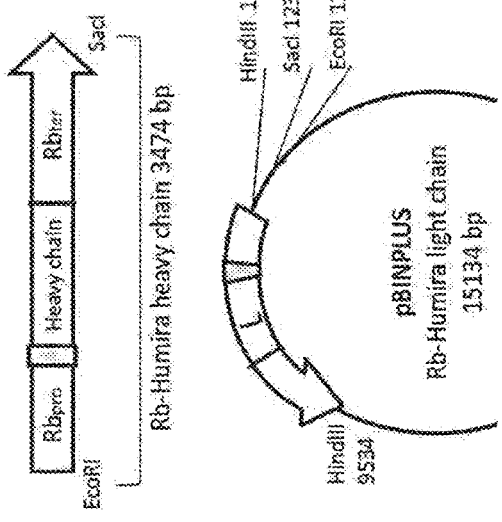
FIGS. 2A-C are schematic illustrations of the cloning of pBINPLUS-Humira coding the light chain and heavy chain on a single plasmid.
Figure 2B:
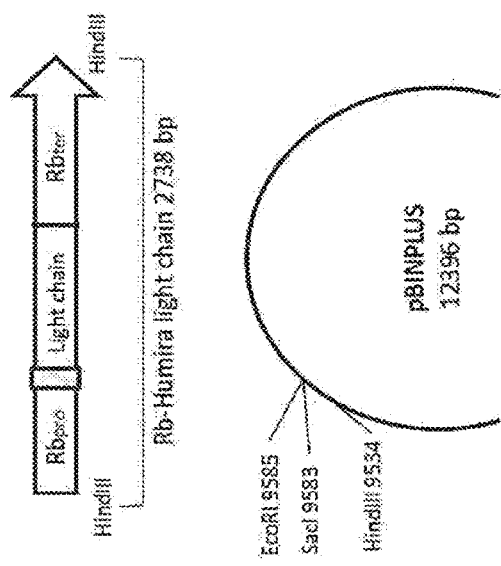

II. At the Next Step, the Binary Vectors pBINPLUS with Both, Heavy and Light Chains with Rubisco Promoter and Terminator, of Every mAb were Constructed: pBINPLUS-Humira (FIGS. 2A-C) and pBINPLUS-Avastin (FIGS. 3A-C).

To create pBINPLUS-Humira, a two steps ligation was applied. At the first step, the pUC18 Rb-Humira light chain was restricted by HindIII and cloned to the pBINPLUS vector restricted by HindIII creating a pBINPLUS Rb-Humira light chain plasmid. At the second step, the pUC18 Rb-Humira heavy chain was restricted by EcoRI and SacI restriction enzymes and cloned with the same enzymes to the pBINPLUS Rb-Humira light chain to create the pBINPLUS Humira with both chains (FIG. 2C).

Figures 3A, 3B, 3C:
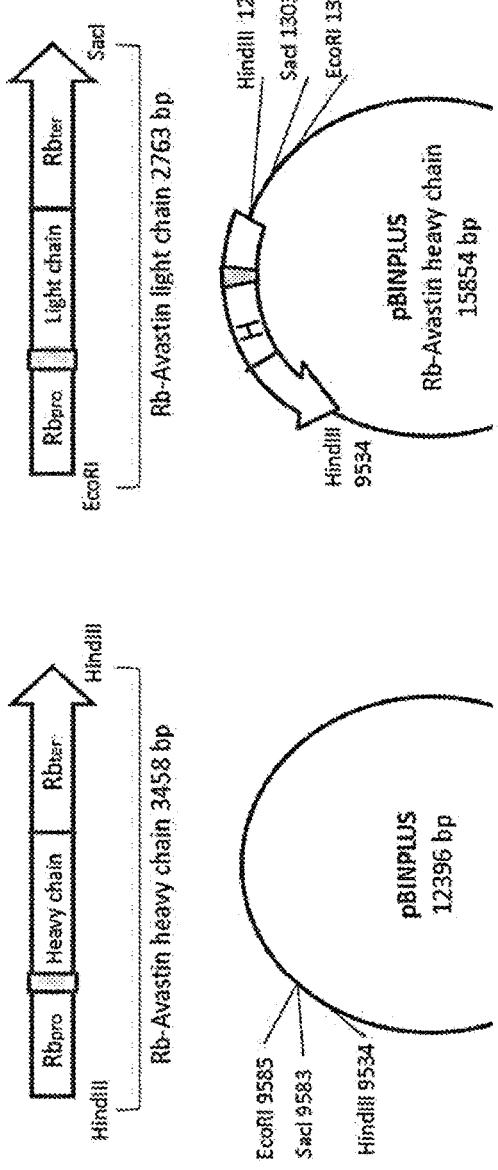
FIGS. 3A-C are schematic illustrations of the cloning of pBINPLUS-Avastin coding the light chain and heavy chain on a single plasmid.

The construction of pBINPLUS-Avastin was performed similarly to that of pBINPLUS-Humira (FIGS. 3A-C). First, Rb-Avastin heavy chain was cloned into pBINPLUS vector by HindIII creating pBINPLUS Rb-Avasin heavy chain (FIG. 3B). Then, Rb-Avastin light chain was cloned to pBINPLUS Rb-Avastin heavy chain by EcoRI and SacI restriction (FIG. 3C).

Figure 2C:
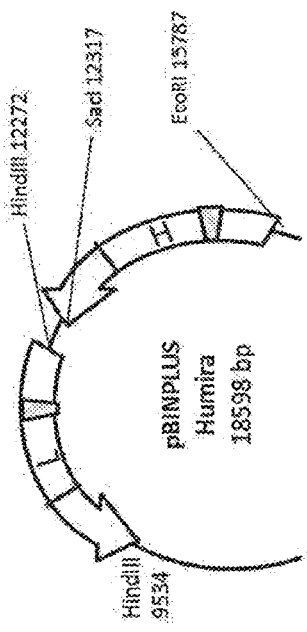

As shown in FIGS. 2C and 3C each of the coding sequences (heavy chain and light chain) is translationally fused at the N-terminus to the Rubisco-derived vacuolar signal peptide.

III. Rubisco-Vac Cassette with Humira (Codon Optimized by Entelechon)—Rubisco Promoter, Vacuolar Signal Peptide (SEQ ID NOs: 18, 19 and 20) and Rubisco Terminator.

Figure 4A:
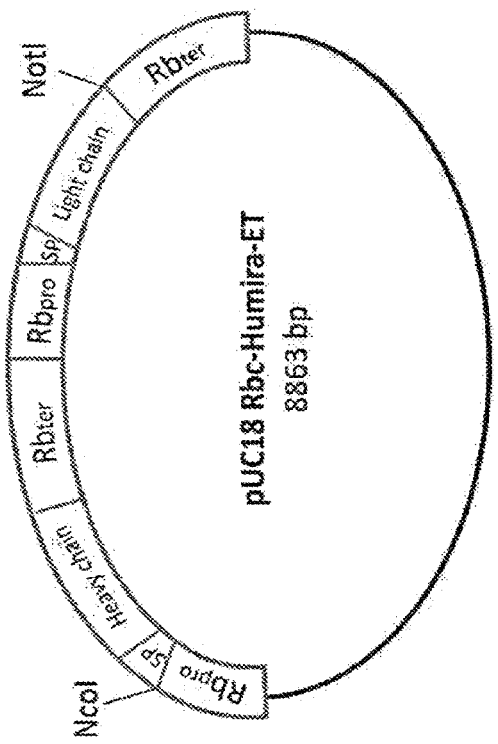
FIGS. 4A-B are schematic illustrations showing the construction of the Humira double cassette in pUC18. The synthetic DNA fragment (SEQ ID NO: 25) including Rubisco terminator, Vacuolar SP1 (SEQ ID NO: 18), Humira heavy chain (SEQ ID NO: 15), Rubisco promoter, Vacuolar SP2 (SEQ ID NO: 19), Humira light chain (SEQ ID NO: 16) was cloned into Rubisco cassette by NcoI, NotI in pUC18 creating double cassette with both mAb chains.
Figure 4B:
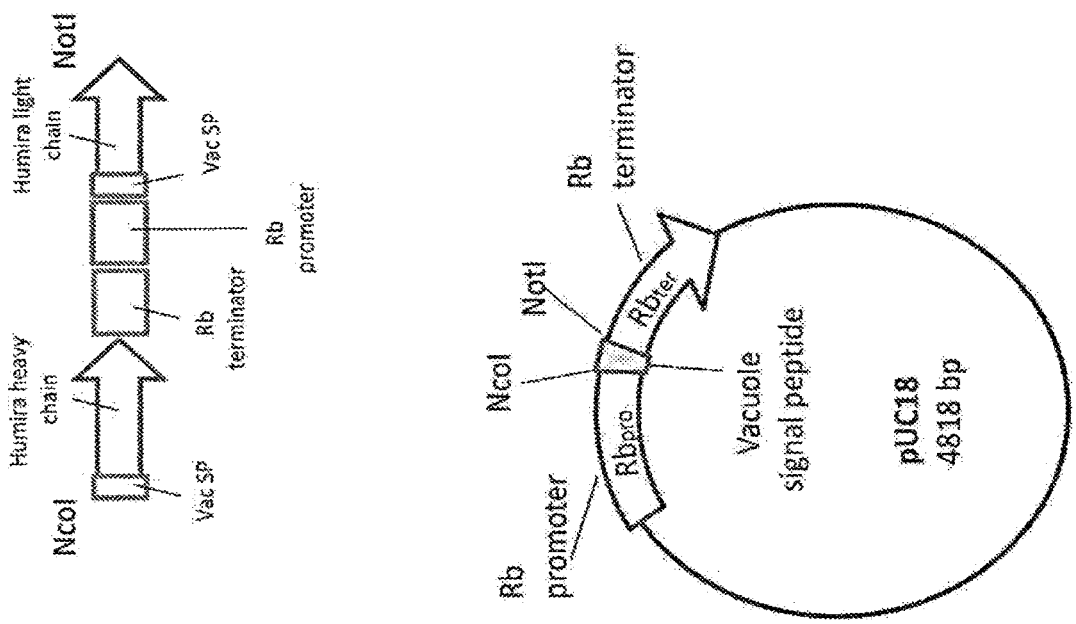

DNA sequence of Humira heavy and light chains was optimized by Leto optimization software (by Entelechon) and the genes (SEQ ID NOs: 15 and 16) were cloned into the Rubisco cassette with Leto optimized vacuolar signals (SEQ ID NOs: 18 and 19). Synthetic DNA fragment including Vacuolar SP1 (seq. 18, 20), Humira heavy chain (SEQ ID NOs 15, 2), Rubisco terminator, Rubisco promoter, Vacuolar signal SP2 (seq. 19, 20), Humira light chain (seq. 16, 2) was inserted into Rubisco expression cassette using NcoI and NotI enzymes thus creating an expression cassette in pUC18 with both Humira chains (SEQ ID NO: 25) (FIGS. 4A-B). The double cassette is cloned into pBINPLUS.

IV. 35S-Vac Cassette—CaMV 35S Promoter, Vacuolar Signal Peptide (SEQ ID NOs. 17 and 20) and NOS (Nopaline Synthase) Terminator (SEQ ID NO: 28).

The genes coding Humira heavy (SEQ ID NO: 1) and light chains (SEQ ID NO: 3) were cloned into 35S-vac cassette, where they were fused in frame to the vacuolar signal peptide regulated by 35S promoter. The expression cassettes were constructed in pUC18 and then transformed into binary plasmid pBINPLUS (SEQ ID NOs: 1 and 3). Constructs pUC18 35S-vac-Humira heavy chain, pUC18 35S-vac-Humira light chain, pBIN 35S-vac-Humira heavy chain, pBIN 35S-vac-Humira light chain were created.

V. For Apoplast Expression, the Rubisco-Cell Cassette was Used Including Rubisco Promoter, Short Cell Signal Peptide (SEQ ID NOs: 21 and 22) and Rubisco Terminator.

Figure 11B:
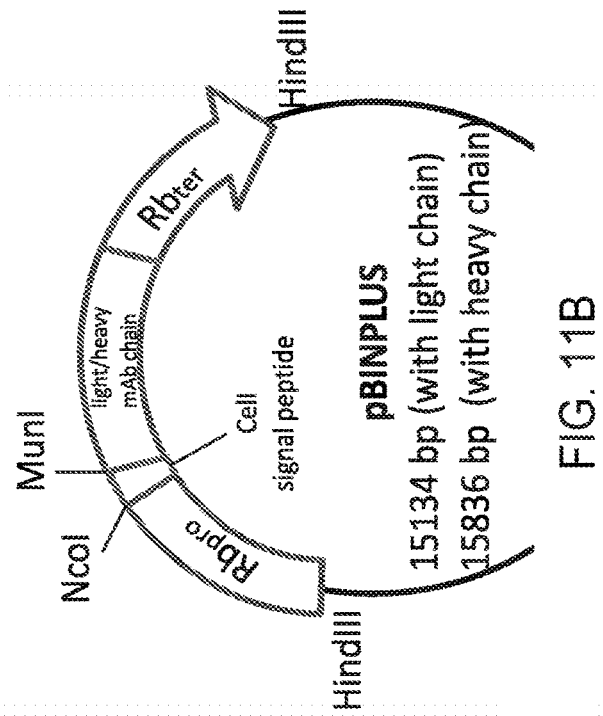
FIGS. 11A-B are schematic illustrations showing construction of the expression cassettes encoding light and heavy chains of the indicated antibodies with a Cell apoplast signal peptide. The mAb (Avastin/Humira) chains were inserted into the expressing cassette including Rubisco promoter, Cell signal peptide and Rubisco terminator. Resultant constructs are: pBINPLUS Rubisco Cell humira heavy chain, pBINPLUS Rubisco Cell humira light chain, pBINPLUS Rubisco Cell avastin heavy chain, pBINPLUS Rubisco Cell avastin light chain. The cassettes with the heavy and the light chain of the same mAb were co-transformed into tobacco plants to get the expression of the full mAb in the apoplast.
Figure 11A:
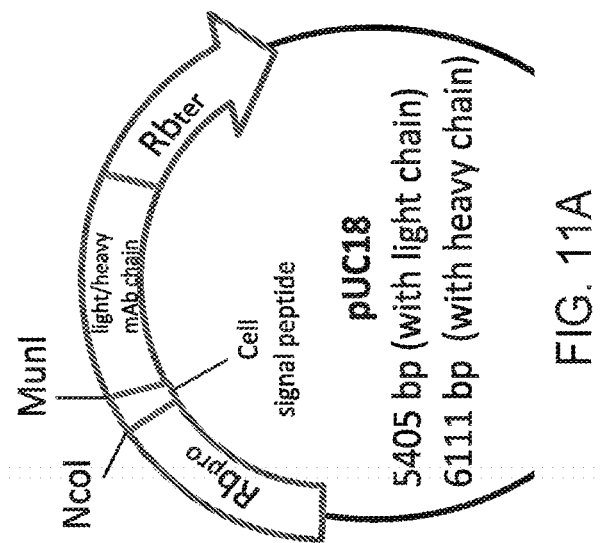

In the mAb containing Rubisco cassette the vacuolar signal peptide (FIGS. 11A-B) was replaced by Cell signal peptide by NcoI/MunI restriction and further ligation, in order to create constructs expressing mAbs chains in the apoplast. The expression cassettes were constructed in pUC18 and then transformed into binary plasmid pBIN-PLUS. Constructs pUC18 RBc-Cell-Humira heavy chain, pUC18 RBc-Cell-Humira light chain, pBIN RBc-Cell-Humira heavy chain, pBIN RBc-Cell-Humira light chain were created (SEQ ID NOs: 1 and 3).

VI. 35S-Cell Cassette—CaMV 35S Promoter, Cell Signal Peptide (SEQ ID NOs: 23 and 24) and NOS (Nopaline Synthase) Terminator (SEQ ID NO: 28).

The genes coding Humira heavy and light chains were cloned into 35S-Cell cassette, where they were fused in frame to the Cell signal peptide and downstream to 35S promoter. The expression cassettes were constructed in pUC18 and then transformed into the binary plasmid pBIN-PLUS. Constructs pUC18 35S-Cell-Humira heavy chain, pUC18 35S-Cell-Humira light chain, pBIN 35S-Cell-Humira heavy chain, pBIN 35S-Cell-Humira light chain were designed (SEQ ID NOs: 1 and 3).

Example 2

Cloning of CBD-PrtA, β-Xylosidase, α-Fucosidase to the Binary pBINPLUS Vector for Tobacco Transformation Mediated by *Agrobacterium*

I. For Vacuolar Expression: 35S-Vac Cassette—CaMV 35S Promoter, Vacuolar Signal Peptide (SEQ ID NOs: 17 and 20) and NOS (Nopaline Synthase) Terminator (SEQ ID NO: 28).

The pUC57 with the expression cassette of CBD-PrtA (SEQ ID NOs: 9 and 10).

Figure 6A:
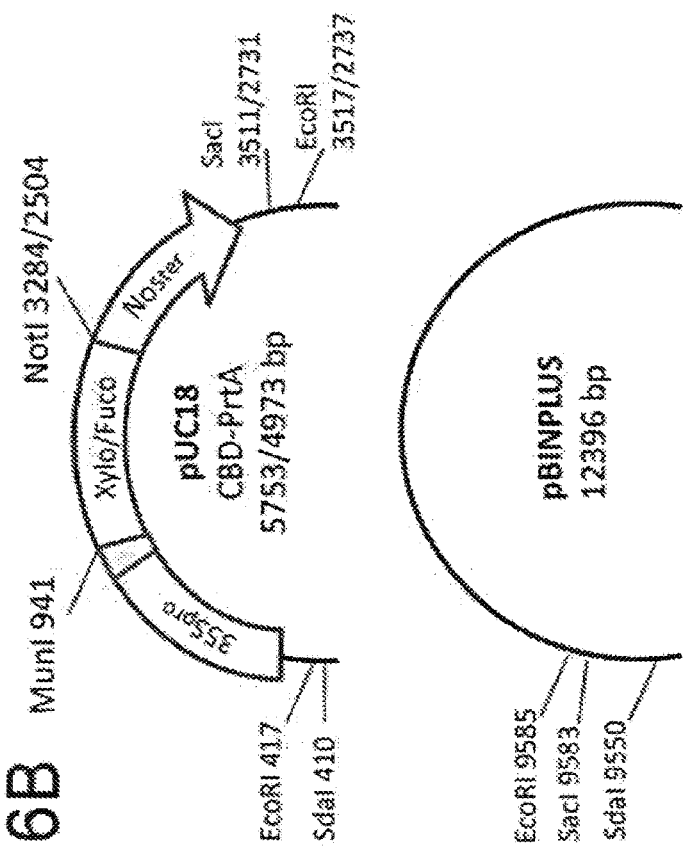
FIGS. 6A-C are schematic illustrations showing cloning of Xylosidase and Fucosidase into pBINPLUS plasmid.
Figure 6B:
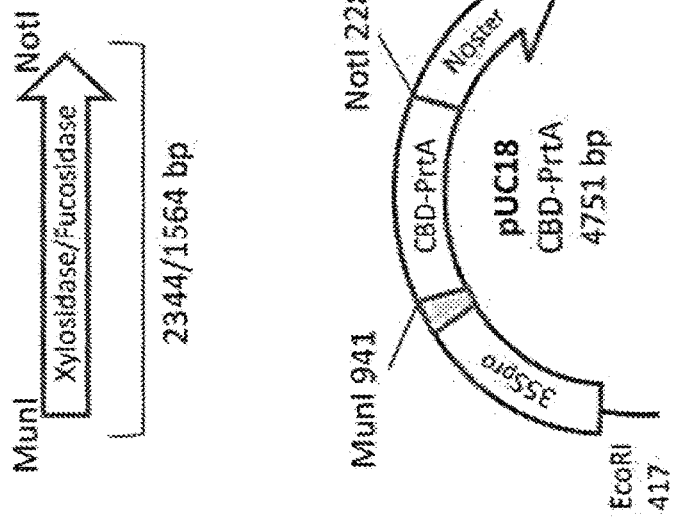
Figure 6C:
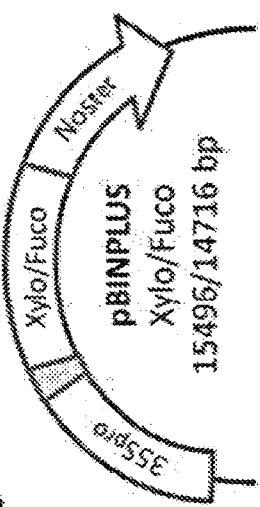

Gene fusion of CBD coding domain (SEQ ID NO: 29) and of Protein A (SEQ ID NO: 30) coding domain under the 35S promoter, vacuole signal peptide and Nos terminator was restricted by PstI, SacI and cloned to pUC18 plasmid (FIGS. 5A-B). The expression cassette in pUC18 was restricted by EcoRI and cloned into pBINPLUS (FIGS. 5B-C). The genes encoding xylosidase (XlnD from *A. niger* SEQ ID NOs: 11, 12) and fucosidase (α-1,3/4-fucosidase from *Streptomyces* sp. SEQ ID NOs: 13, 14) restricted by MunI and NotI were cloned into expression cassette instead of CBD-PrtA (FIGS. 6A-C). The constructs of pUC18 35S-Xylosidase and pUC18 35S-Fucosidase were made. The expression cassettes were cloned to pBINPLUS binary plasmid by SdaI and SacI restriction to create pBINPLUS 35S-Xylosidase and pBINPLUS 35S-Fucosidase plasmids (each being directed to the vacuole via a Vac SP).

II. For Apoplast Expression: 35S-Cell Cassette—CaMV 35S Promoter, Cell Signal Peptide (SEQ ID NOs: 23 and 24) and NOS (Nopaline Synthase) Terminator (SEQ ID NOs: 28).

Two constructs for apoplast expression of xylosidase and fucosidase were constructed. The vacuolar signal peptide was replaced by Cell signal peptide using NcoI, MunI restriction sites to construct pUC18 35S-Cell-Xylosidase, pUC18 35S-Cell-Fucosidase, pBINPLUS 35S-Cell-Xylosidase, pBINPLUS-35S-Cell-Fucosidase.

III. Transformation to *E. Coli*

Transformation was performed using Heat Shock. 50 μl of DH5a competent cells were used for transformations and 100 μl of competent cells for ligation. 50 ng of circular DNA was added into *E. coli* cells which then were thawed on ice for 20 minutes. Heat Shock was performed in 42° C. for 1 minute and back on ice for 5 minutes. 1 ml of LB was added and incubated for 1 hour at 37° C. Bacterial cells were cultured on LB plates (with appropriate antibiotic added e.g., Ampicillin or Kanamycin, dependent on the resistance gene on the construct) 100 μl for transformation and 1000 μl for ligation. Cells were incubated overnight.

IV. *Agrobacterium* Transformation

Electroporation was carried out in cuvettes with a 1 mm gap distance using competent *Agrobacterium tumefaciens* (strain LBA 4404). Electroporation conditions were set to 25 μF, 2.5 kV, 200 Ω. *Agrobacterium* cells were thaw on ice. 1 μl of miniprepped DNA was mixed briefly with 80 μl bacteria and transferred to a pre-chilled cuvette. Following electroporation, 1 ml of sterile LB medium was added and transferred to a test tube. Bacteria were incubated at 28° C. for 3 to 4 hours on a roller drum. Following this, bacteria were plated on selective LB Ampicillin or Kanamycin medium.

V. Transgenic Tobacco Plants Production

Tobacco plants were grown under sterile conditions to about 4-5 weeks. An *Agrobacterium* starter was prepared in 25 ml of LB medium with the addition of 50 mg/ml kanamycin. Cells were incubated for 48 h in a shaking incubator at 28° C. to a stationary stage. Starters were then centrifuge for 10 min at 5500 rpm at room temperature. Upper medium was removed, pellet was resuspended in sterile liquid MS medium (4.4 g/L Murashige & Skoog (MS) medium including vitamins from Duchefa (cat #M0222.0050), 30 g/L sucrose from J. T. Baker (cat #4072-05), pH=5.8) to final turbidity of O.D.600 0.5. About 10 ml of the MS containing bacteria were placed on a sterile petri dish. Green leaves of the tobacco plants were cut with sterile tweezers and scalpel and incubated for 5 min with *Agrobacterium* in the MS suspension. Leaves were then transferred to petri dishes that contained a solid MS (liquid medium with 0.7% plant agar from Duchefa (cat #P1001.1000)) medium that included 0.8 ml/L IAA and 2 ml/L kinetin). Plates were incubated at 28° C. in the dark for 48 hours. Following two days, the leaves were transferred to petri dishes containing a selective MS medium (0.8 ml/L IAA and 2 ml/L kinetin+400 mg/L carbenicillin and 100 mg/L kanamycin). Plates were placed at a light room for 3 weeks and media was changed every 10 days. During this period shoots were formed from the leaves. The shoots were transferred to petri dishes containing MS medium with 100 mg/L kanamycin and 400 mg/L carbenicillin at the same light condition. Shoots that produced roots were transferred to the soil, covered with nylon for two days. Plants were then transferred to pots with ground, for further analysis.

Example 3

CBD-PrtA Expression and Activity in Tobacco

CBD-PrtA expression in tobacco was assayed by Western blot with anti-CBD antibody.

SDS-PAGE Western Blot

SDS-PAGE analysis was performed using a "mini protein gel system" (Hercules, Calif., USA). Western Blot analysis was performed as described before (Ausubel et al 1987). Protein samples were loaded onto a 12.5% SDS PAGE system. After electrophoresis protein were transferred on to a nitrocellulose membrane (Amersham Biosciences, England) using the "mini trans blot cell"—(Hercules, Calif., USA) for 2 hours in a cooled buffer with 10% ethanol and steady current of 150V. After transfer, the membrane was blocked with 4% skim milk for 0.5 hour in R.T. The membranes were exposed to primary antibody overnight at RT and afterwards washed 3 times with TBST. Secondary antibody exposure (alkaline phosphatase (AP) conjugated) was performed for 2 hours followed by additional three washes. Finally, the membrane was washed and developed with 5-bromo-4-chloro-3-indolyl phosphate (BCIP) and nitro blue tetrazolium (NBT) substrates (Sigma). BCIP/NBT Substrate Solution was prepare by adding 33 ml of 50 mg/ml BCIP Stock Solution and 66 µl of 50 mg/ml NBT Stock Solution to 10 ml of Substrate Buffer (100 mM Tris, 100 mM sodium chloride, and 5 mM MgCl2, pH 9.5. Adjusted with HCl).

Figures 7A, 7B:
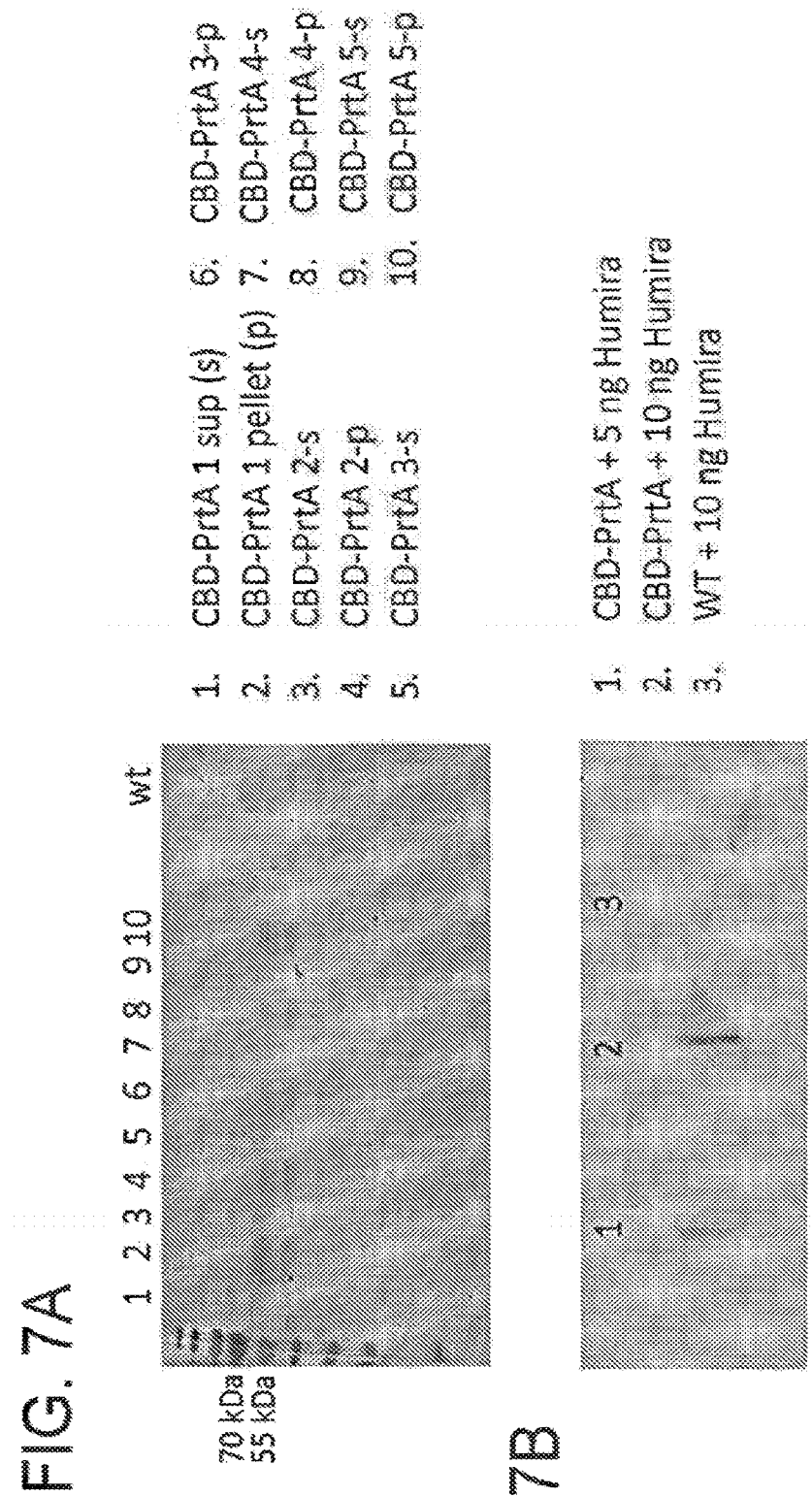
FIGS. 7A-B are Western blot images showing that CBD-PrtA (SEQ ID NO: 10) is expressed in the tobacco plants.

Specifically, for FIG. 7A—100 mg of the plant tissue was homogenized in SAB (weight/volume ratio 1:1), the pellet was separated from the soup by centrifugation and the 30 µl of the soup and the pellet were loaded to the SDS PAGE, then we proceeded to the Western blot analysis with anti-CBD antibody. For FIG. 7B—100 mg of the tobacco tissue of the plant expressing CBD-PrtA were homogenized in the 100 µl Buffer 1 (100 mM Tris-HCl pH 7.4, 250 mM NaCl, 10 mM EDTA, Complete protease inhibitor) with 5 ng, and 10 ng of adalimumab. The plant pellet was separated from the soup and washed. The pellet extract was applied on the nitrocellulose membrane and the mAb was detected by anti human IgG-HRP.

Thus as shown, the protein was detected at the pellet of the plant tissue and its size was approximately 55 kDa which corresponds to the size of CBD-PrtA fusion protein (FIG. 7A). FIG. 7B shows that CBD-PrtA expressed in tobacco and binds human IgG (FIG. 7B).

Example 4

Xylosidase and Fucosidase are Expressed and are Active in Tobacco Plants

I. Fucosidase and Xylosidase Activity Scanning

Fucosidase and Xylosidase activity were tested in black 96 well plate (Nunc). For each reaction, 0.5 mm$^2$ fresh tobacco leaf tissue was taken and immediately incubated in 200 µl of 50 mM sodium acetate buffer pH=5.0. 10 µl of 0.15 mM substrate were added and the samples were incubated for 1 hour in 65° C. 4-Methylumbelliferyl β-D-fucopyranoside (Mu-Fuc) (Sigma Aldrich M5510) and 4-Methylumbelliferyl-b-D-xylopyranoside (MU-Xyl) (Sigma Aldrich M 7008) were used as substrates for Fucosidase and xylosidase, respectively. The reaction was terminated by the addition of 21 µl NaOH (f c. 100 mM). Fluorescence was measured at excitation 360 nm, emulsion 460 nm.

II. Enzymatic Activity Quantification

Plant tissue from transgenic plant lines expressing Fucosidase and Xylosidase was extracted by grinding leaf in liquid nitrogen, with acetate buffer (50 mM Sodium Acetate, 15 mM Potassium Meta bi-sulfite, complete (Sigma Aldrich) protease inhibitor cocktail (1 tablet per 100 ml)). Extracts were incubated for 1 hour at RT, centrifuged at 11,300 g for 10 min at 4° C., soluble fraction was separated from pellet and filtered through 0.2 µm PVDF filter. The soluble fractions were diluted in 50 mM sodium acetate buffer pH=5.0 to concentrations ranging from 0-5.5 µl/well for Xylosidase and 0-70 µl/well for Fucosidase. The ability of the enzymes to hydrolyze 10 µl of Mu-Fuc for Fucosidase and 10 µl of MU-Xyl for Xylosidase was tested and activity calculated using a 4-Methylumbelliferone calibration curve. 4-Methylumbelliferone calibration curve was made from commercially available 4-Methylumbelliferone that was diluted to a final concentration range of 0.01-10 µg/ml. The trend line equation was obtained and fluorescence units (FU) per mass of 4-Methylumbelliferone were calculated.

Calculation of enzyme units per 1 g of plant tissue was calculated using the following equation:

$$\frac{\text{enzyme units}}{1\text{ g leaf tissue}} = \frac{\text{activity per 1 g per 1 min}(FU)}{4\text{-Methylumbelliferone 1 umol flourescene}(FU)}$$

Results

Figure 8:
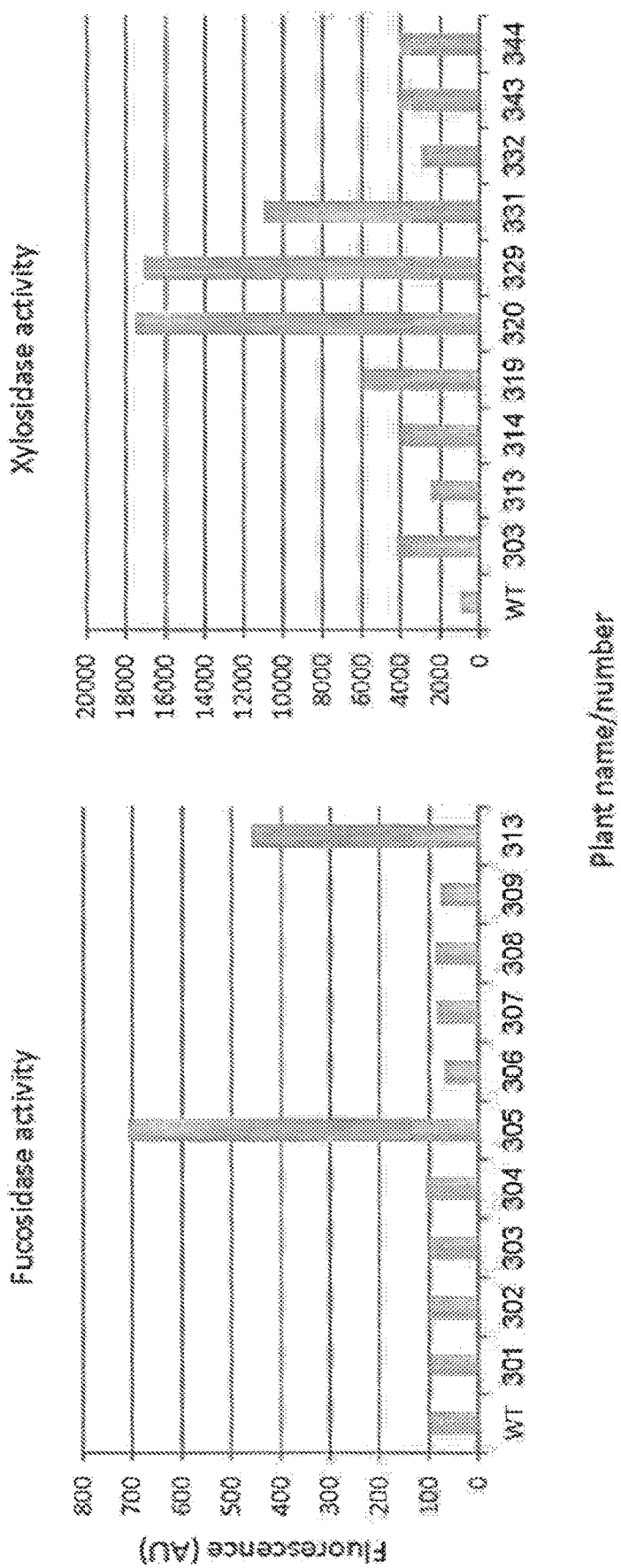

The activity of xylosidase and fucosidase was measured in recombinant tobacco plants. A number of tobacco plants with a substantial expression of recombinant xylosidase and fucosidase were detected (FIG. 8).

Figure 13:
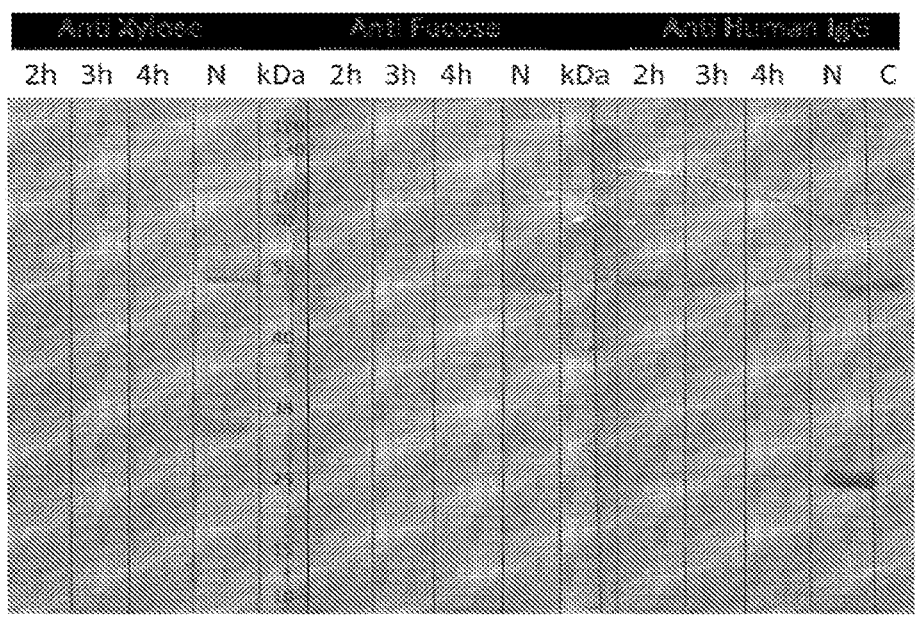

Conditions for Xylose and Fucose residues reduction were determined by treating 4.8 µg of plant-derived adalimumab (PDA) antibody with 1.5 ml of plant extracts expressing β-xylosidase and α-fucosidase. Reactions were carried out in 15 mM PBS buffer pH 7.5 for 2, 3 and 4 hours in RT. Different types of treatment were made: β-xylosidase and α-fucosidase alone (data not shown) and β-xylosidase and α-fucosidase combined together (FIG. 13). Each treatment was analyzed with three different sets of antibodies: Anti-Xylose, Anti-Fucose and Anti-Human IgG.

It was observed, that individual treatments with β-xylosidase or α-fucosidase was less efficient (not shown) than a combined treatment with both enzymes. In the combined treatment, best results were obtained after 2 hours (FIG. 13, 2 h) incubation. Almost all Xylose and Fucose residues were cleared, while the PDA degradation was the lowest (FIG. 13 with anti-human IgG). Positive control—not treated PDA (N) shows clear band with both Anti-Xylose and Anti-Fucose. Detection with Anti-Human IgG shows evidence for PDA existence in all treatment.

Example 5

Adalimumab is Expressed and is Active in Tobacco Plants

I. Adalimumab Activity Test

Adalimumab activity assay was performed by Harlan Biotech Ltd. Israel. Briefly, activity was tested by antibody neutralization of TNF-α mediated cytotoxicity in L929 fibroblast cell line. Two 96-well tissue culture plates were filled with 100 µl of L929 cells suspension at a density of $3.5 \times 10^5$ cells/ml and incubated overnight at 37° C., 5% $CO_2$ in a humidified incubator. Following 12 hr incubation, rhTNF-α and Actinomycin D were added to achieve a final concentration of 1 ng/ml rhTNF-α and 1 µg/ml Actinomycin D, followed by an additional incubation of 2 hours at 37° C., 5% CO2 in a humidified incubator. Then, the first plate (the experiment plate) was incubated with Plant Derived Adalimumab (PDA) at a concentration range of 0-2000 ng/ml, and a second plate (control plate) was incubated with commercial Humira at a final concentration range of 0-2000 ng/ml. An MTT solution was added to each well at a final concentration of 0.5 mg/ml. Labeling was carried out 4 hours 37° C. Following incubation, the MTT solution was removed and 100 µl of Iso-propanol added to each well for no less than 30 minutes. Absorbance signal was measured in a microplate spectrophotometer (Multiscan® FC; Thermo Scientific) at 570-650 nm wavelength filters.

Adalimumab ELISA

Plant sample preparation was performed as follows: six leaf discs were sampled directly into a pre-weighed eppendorf containing grinding buffer (100 mM Tris-HCl pH 8, 25 mM NaCl, 1 mM PMSF, 10 mM EDTA, 1 mM PMBS) by clipping with the 1.5 ml Eppendorf lid on a plant leaf, and immediately placed on ice. Care was taken to sample leaves from lower, middle and upper plant sections. The samples were then weighed and ground for 30 seconds using a plastic mortar at 500 RPM. The soluble fraction was extracted by centrifugation for 15 min at 11,000 RPM in 4° C. Samples were diluted 500 folds before application on Elisa plate. Calibration curve was made from commercial Humira. Adalimumab was serially diluted to achieve a final concentration range of 0-100 ng/ml.

ELISA: untreated 96-well plate were coated with 100 µl of 100 ng/ml rhTNF-α solution and afterwards thoroughly washed. Samples for calibration curve and test samples were loaded in duplicate and incubated for 1 h in 37° C. The plate was washed 4 times with TBST wash solution and then loaded with 1:50,000 goat anti-Human IgG HRP conjugated, and incubated for 1 h in 37° C. After 4 washes with TBST, 100 µl TMB substrate Solution was added. The reaction was stopped after 20 minutes with 100 µl $H_2SO_4$ 0.5 N. Absorbance signal was measured in microplate reader at 450 nm wavelength.

Results

Figure 9:
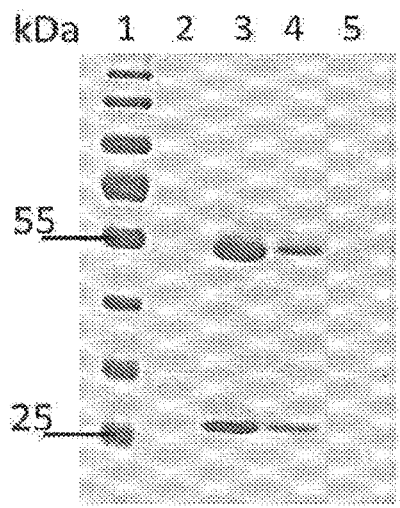

Apoplast expressed adalimimab was purified from 40 g homogenized tobacco leaves on Protein A column. Lines 2-5: 30 µl of the elution fractions were analyzed by SDS PAGE, two bands corresponding to the heavy (55 kDa) and the light chain (25 kDa) of the antibody are seen in the lines 3 and 4 of FIG. 9 (RUBISCO promotor and terminator with Cell signal peptide (RbCell)).

Figure 10:
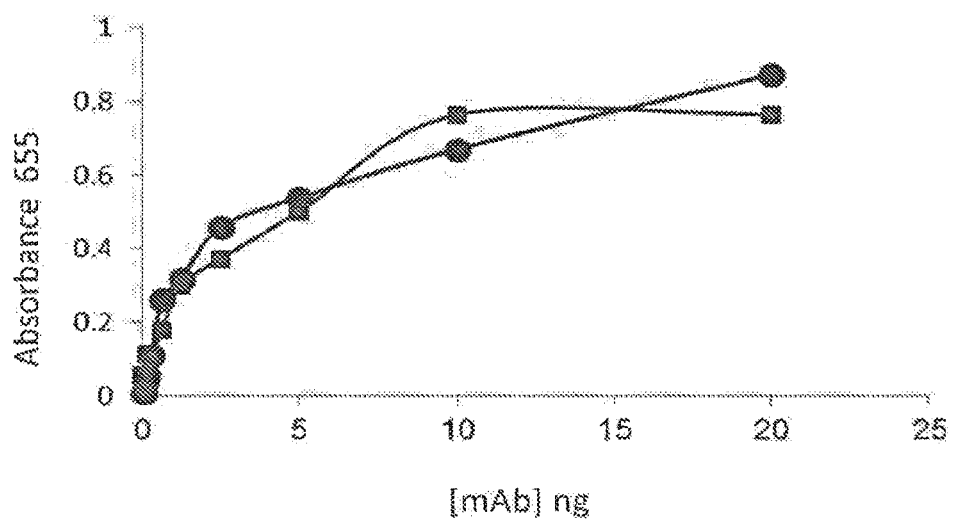

FIG. 10: Plant derived adalimumab shows in-vitro activity similar to the commercial therapeutics. TNF-α precoated ELISA plates were incubated with commercial therapeutics (gray) and plant derived adalimumab (red), binding of the mAb to the target was detected by using anti-human IgG-HRP.

Figure 14:
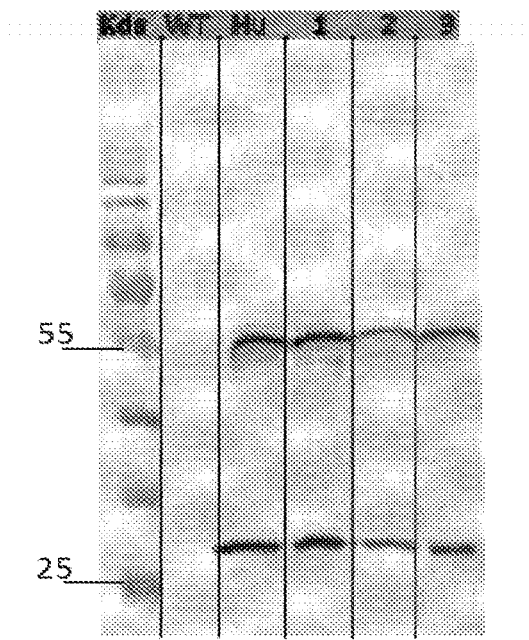
Figure 15:
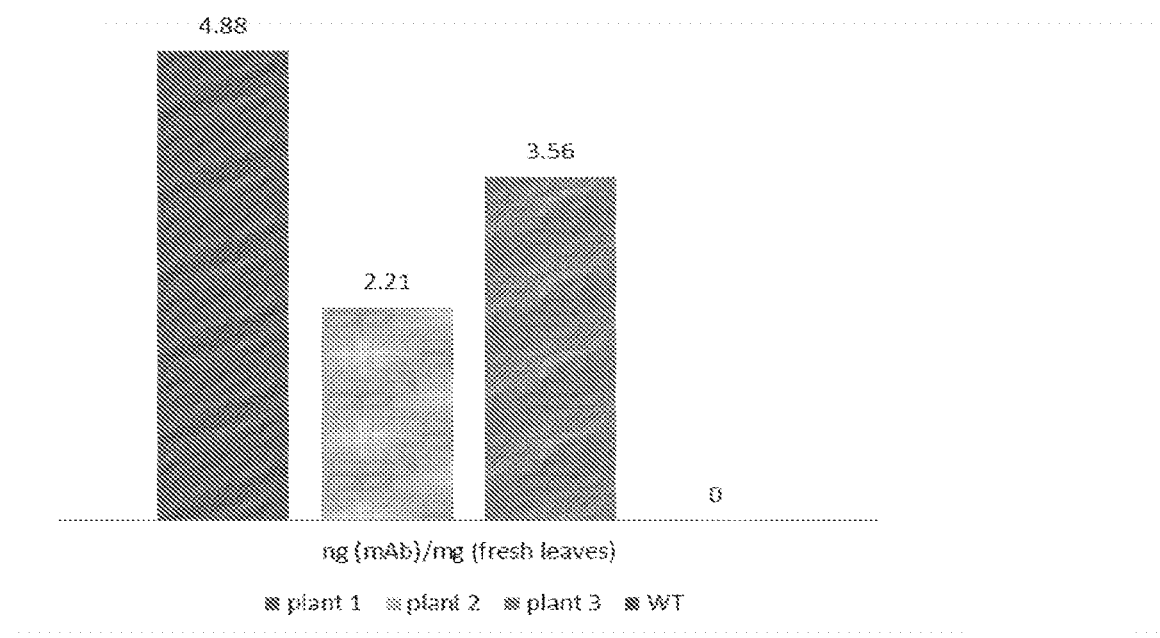

In a separate experiment, apoplast expressed adalimumab was tested for yield quantification. Plant Derived Adalimumab (PDA) was purified from three different transgenic tobacco plant lines with stable expression of PDA and analyzed by SDS-PAGE Western blot and ELISA. Western blot (FIG. 14) showed bands at approximately 55 and 25 kDa, corresponding to adalimumab heavy and light chain, respectively. ELISA quantification (FIG. 15) showed that plants 1, 2 and 3 yielded 4.88, 2.21 and 3.56 mg PDA/kg leaves, respectively. The WB and ELISA results were consistent, with SDS-PAGE bands corresponding in strength to the ELISA quantification.

Figure 16:
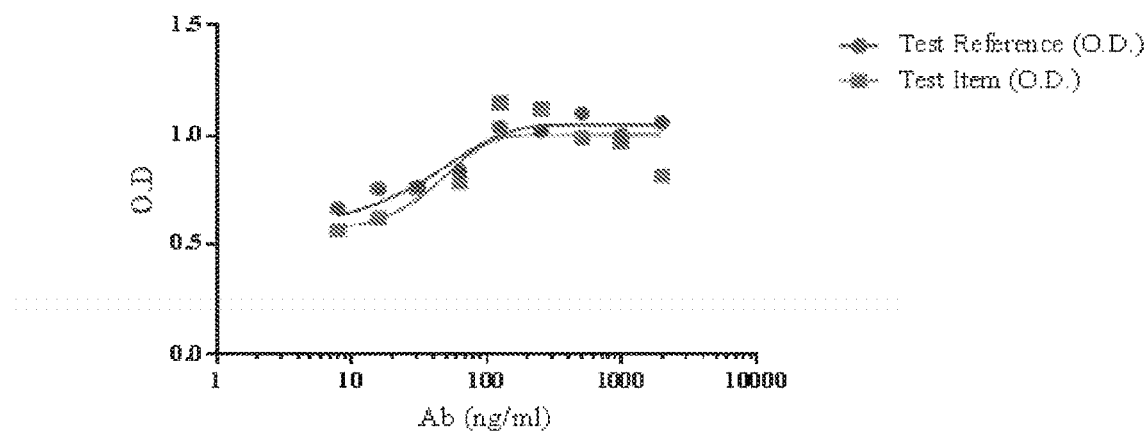

PDA bioactivity, of neutralization of rhTNF-α, was tested in comparison to bioactivity of commercially available Adalimumab (Humira), in L929 cell line. PDA shows almost the same results as commercial Humira (FIG. 16). Downwards trend was observed in PDA.

Example 6

In-Planta Purification of the Plant Derived mAb by Protein a Fusion with Transmembrane Domain (TMD) or a Cellulose Binding Domain (CBD)

Protein A—TMD

The present inventors have also utilized a protein A fusion with membrane anchoring domain in order to attach a mAb to the plasma membrane of the plant cells as a first step of the purification process. The mAb is bound by protein A which is anchored to the plasma membrane by TMD. Thus after the plant is harvested and a pellet is separated from the soup, the mAb is found in the pellet part.—DON'T YOU HAVE TO RUPTURE THE CELLS? WHAT SP WILL THE AB HAVE? No, the procedure is the same as with CBD-ProteinA but instead CBD we use TMD, the detachment of mAb made by pH change. The SP is Cell for targeting to the apoplast.

Figure 12D:
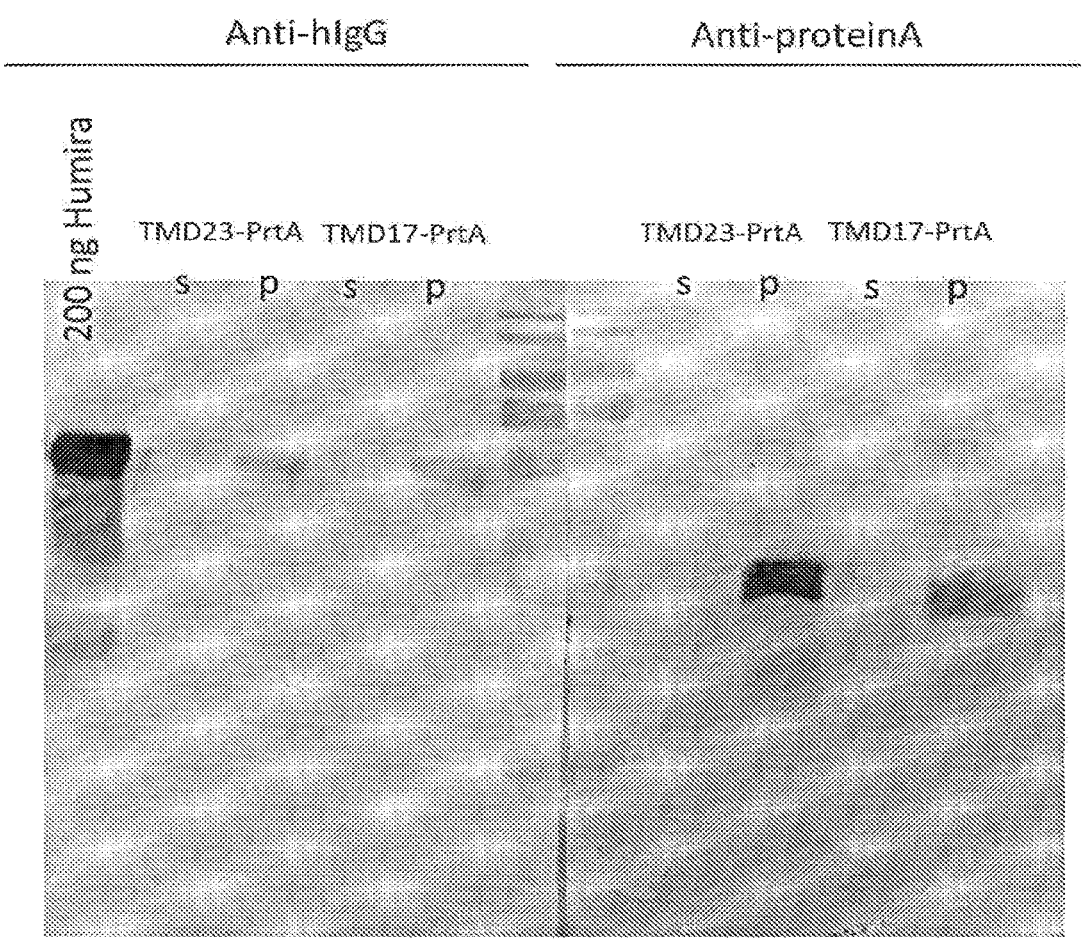

The constructs are shown in FIG. 12A.

Schematic representation of the constructs is shown in FIGS. 12A-C. The transmembrane domain was attached via a linker to protein A (SEQ ID Nos: 30-36). The resultant sequences optimized for protein expression in plant cells are as set forth in SEQ ID NOs: 35-36.

The PrtA-TMD construct was first incorporated into 35S expression cassette in pUC18 plasmid using MunI and SacI restriction sites. Then the full cassette was transferred into pBINPLUS binary plasmid.

Protein A-CBD

In order to obtain a double transgenic plant, expressing both adalimumab and CBD-Protein A, a stable adalimumab expressing transgene (Apoplast expressed) was transiently transfected with a CBD-Protein A construct. Transient expression was performed as described by Li et al., 2008 Plant Physiol. 147(4):1675-1689. Briefly, one single colony of *Agrobacterium* was inoculated in 5 ml LB with 100 µg/ml kanamycin and grown overnight at 28° C. 1 ml of the overnight culture was used to inoculate 25 ml LB (with 100 µg/ml kanamycin and 20 µM Acetosyringone). The inoculate was grown overnight at 28° C. to final A600=0.4. Infiltration was performed with 5 ml syringe.

Plant tissue preparation for In vitro binding assay: plant tissue was ground in Binding buffer (20 mM Sodium Phosphate pH 7.5) or Grinding buffer (100 mM Tris-HCl pH 7.5, 25 mM NaCl, 1 mM PMSF, 10 mM EDTA, 1 mM PMBS) w/v with 50 mg of cellulose. Extracts were incubated for 1 h in 4° C. for better binding. Pellet separation from soluble fraction was made by centrifugation 30 min at 10,000 RPM. Soluble fraction was discarded and kept for further analysis. Pellet was washed with 1 volume binding buffer, followed by centrifugation 15 min at 10000 RPM. Both pellet and soluble fractions were resuspended in Sample Application Buffer, heated for 10 min in 100° C. and analyzed by Western Blot (as described above).

Results

PrtA-TMD

The fusion PrtA-TMD proteins were transiently expressed in mAb expressing tobacco plants. At day 6 the plant tissue was homogenized, the soup (designated by s) was separated from the pellet (p) and both were analyzed by Western blot with anti-human IgG Ab and with anti-protein A Ab. As can be seen at the left side of the figure (FIG. 12D), most of the mAb was found in the pellet part of the sample, where the protein A fusion was found (right side of the figure).

PrtA-CBD

Figures 17A, 17B, 17C:
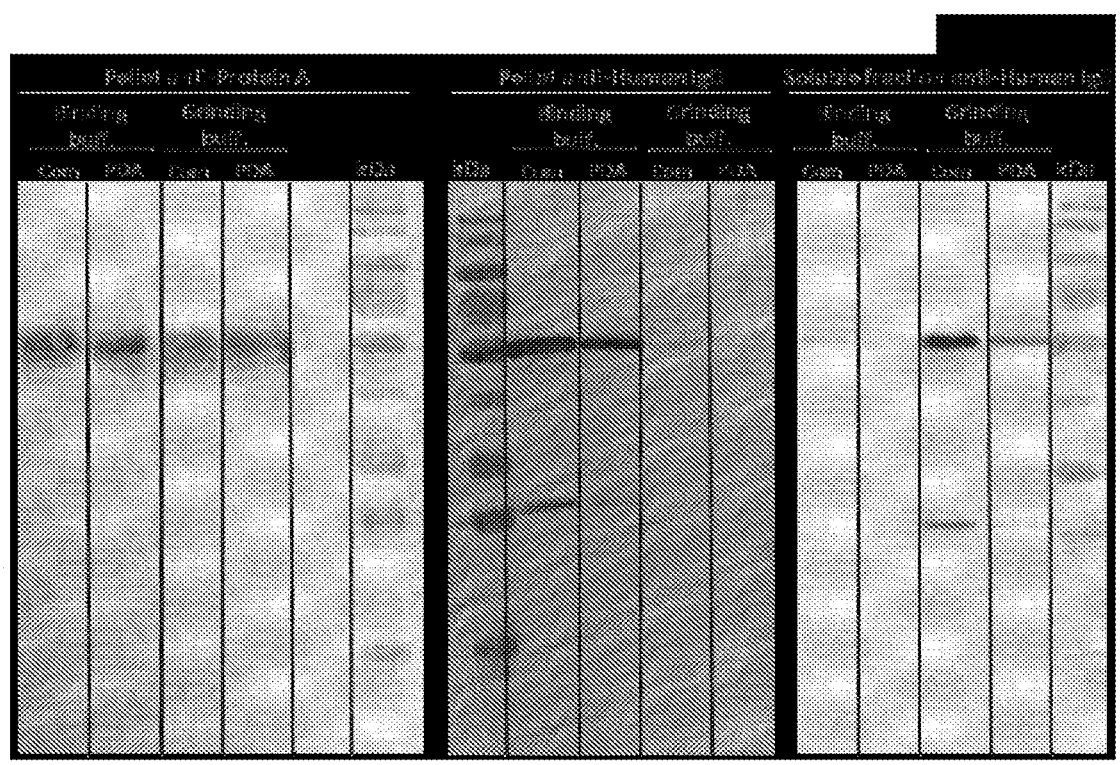
FIGS. 17A-C show the results of SDS-PAGE Western Blotting.

In a separate experiment where a Prt-CBD was used, mAb was extracted and purified from plant leaves and analyzed by western blot with anti-Protein A and anti-Human IgG separately. As a positive control, spiking of 5 µg of Commercial Humira to a CBD-Protein A expressing plants extract, was used at the same conditions. It is shown, that soluble fraction was almost clear when extraction was performed with Binding buffer whereas when Grinding buffer was used bands corresponding to heavy and light chains were detected in both commercial Humira control (Com) and in plant derived adalimumab (PDA) samples (FIG. 17C) in the pellet mAb (FIG. 17B) and CBD Protein A (FIG. 17A) were detected also in both control (Com) and PDA samples also when using Binding buffer, showing that binding of mAb to protein A and CBD to cellulose occurs and Binding buffer is the most efficient one.

Example 7

Suppression of Xylose and Fucose Glycosylation by RNAi (GMD) and RNA Suppression (XylT)

Suppression of Xylose and Fucose glycosylation was performed according to Matsuo, et all, 2014. Briefly, SGDP-mannose-4,6-dehydratase (GMD) RNAi silencing technique was chosen to perform deletion of plant-specific sugar residues in plant N-glycans by repression of GDP-D-mannose 4,6-dehydratase genes. RNAi GMD demolishes α-1,4-Fucose and α-1,3-Fucose residues by interfering in α-1,4-Fucose transferase and α-1,3-Fucose transferase pathway I. Cloning of GMD RNAi to the pBINPLUS Binary Vector for Tobacco Transformation Mediated by *Agrobacterium*:

The genes encoding GMD RNAi fragment were inserted in a 3 step cloning into pUC18 plasmid containing under the 35S promoter (FIG. 18A). Step 1: GMD antisense encoding DNA was inserted by restriction with NotI and BamHI (FIG. 18B) to form the pin structure. Step 2: β-Xylose transferase (XylT) intron encoding DNA from *Arabidopsis* was inserted by restriction with BamHI and MfeI (FIG. 18C) to form the loop structure. Step 3: GMD sense encoding DNA was inserted by restriction with MfeI and NcoI (FIG. 18D) to complete the pin structure of double stranded RNA. The expression cassette was then cloned into pBINPLUS binary plasmid by HindIII and SacI restriction enzymes to generate pBINPLUS GMD RNAi plasmids (FIG. 19A-B).

Plasmids were then transformed into *Agrobacterium* strains LB4404 or EHA105 and into tobacco plants.

II. Cloning of XylT RNA Suppression Construct to the pBINPLUS Binary Vector for Tobacco Transformation Mediated by *Agrobacterium*:

The Xylosyltransferase RNA suppression fragment encoding DNA was obtained from *Nicotiana tabacum* XylT gene for putative β-(1,2)-xylosyltransferase, exon 3 (Sequence ID: emb|AJ627183.1).

Figure 20A:
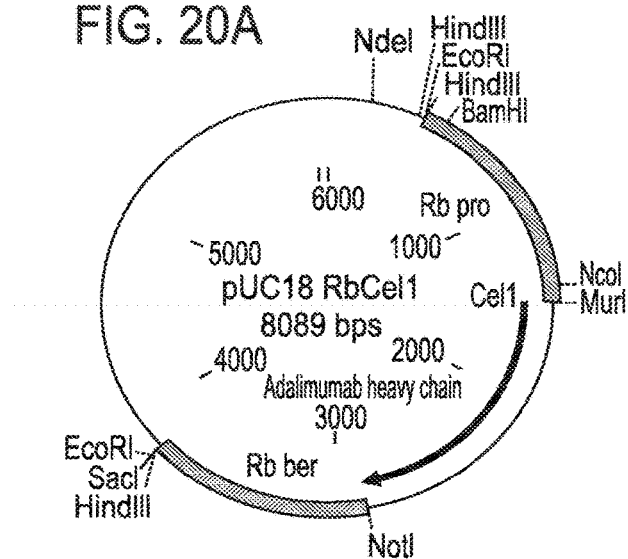
FIGS. 20A-D show the cloning of XylT into pBINPLUS plasmid.
Figure 20B:
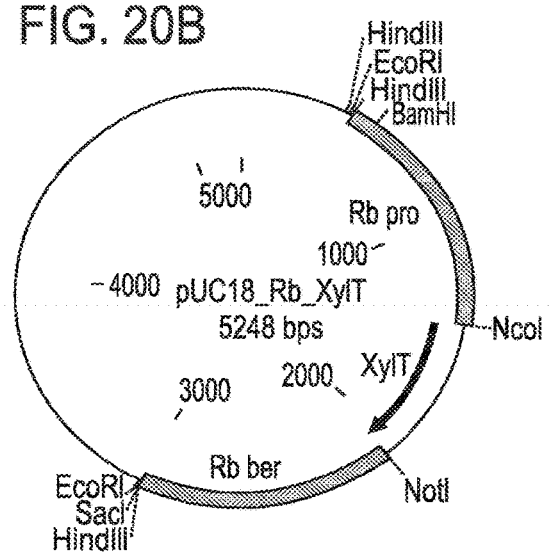
Figure 20C:
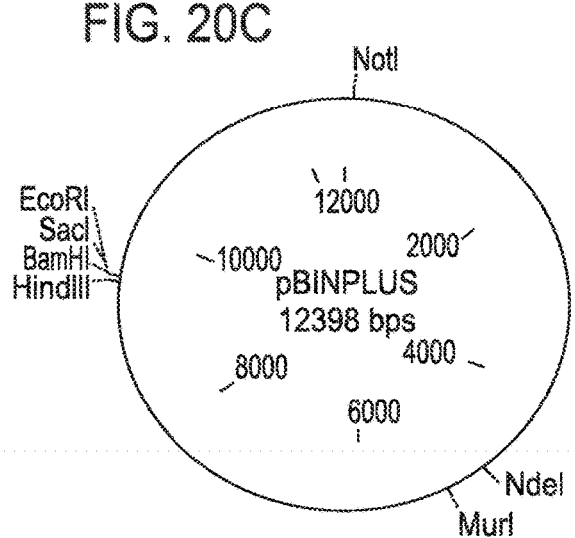
Figure 20D:
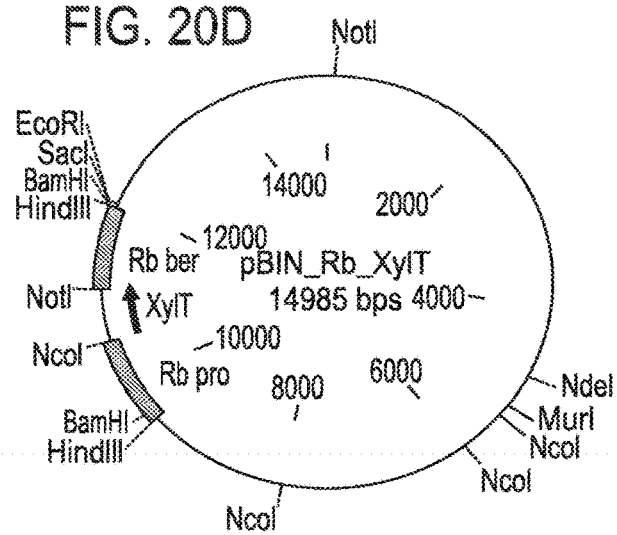

For RNA suppression, a of 617 bp DNA fragment from exon 3 of the XylT gene were amplified by PCR and NcoI and NotI restriction sites were added to the 5' and 3'ends, respectively. The fragment was cloned into pUC18 plasmid under the RUBISCO promotor (FIG. 20A). The Adalimumab heavy chain (1362 bp) was removed by NcoI and NotI restriction and replaced with the XylT fragment (FIG. 20B). The expression cassette was then cloned into pBINPLUS binary plasmid with HindIII restriction enzyme to generate pBINPLUS XylT plasmid (FIGS. 20C-D). Plasmids than were transformed into *agrobacterium* strains LB4404 or EHA105 and then to tobacco plants.

RNA silencing and RNAi sequences for silencing expression of GMD and XylT in tobacco (SEQ ID NOs: 37-40).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Bardor M, Faveeuw C, Fitchette A C, Gilbert D, Galas L, Trottein F, Faye L, Lerouge P (2003) Immunoreactivity in mammals of two typical plant glyco-epitopes, core a(1, 3)-fucose and core xylose. Glycobiology. 13:427-434.

Matsuo K., and T. Matsumura Deletion of fucose residues in plant N-glycans by repression of the GDP-mannose 4, 6-dehydratase gene using virus-induced gene silencing and RNA interference (2011). Plant Biotechnology Journal. 9: 264-281.

Svab Z and Maliga P (1993). High-frequency plastid transformation in tobacco by selection for a chimeric aadA gene. Proc Natl Acad Sci USA. 90(3): 913-917

Wei S., Marton I., Dekel M., Shalitin D., Lewinsohn E., Bravdo B. and Shoseyov O. (2004) Manipulating volatile emission in tobacco leaves by expressing *Aspergillus niger* ß-glucosidase in different subcellular compartments. Plant Biotechnol. J Wilson I B H (2002) Glycosylation of proteins in plants and invertebrates. Curr Opin Struct Biol 12: 569-577

"Biopharmaceuticals in Plants: Toward the Next Century of Medicine" by KATHLEEN LAURA HEFFERON—2010

Brandizzi F. et al. The Destination for Single-Pass Membranes Proteins Is Influenced Markedly by the Length of the Hydrophobic Domain. The Plant Cell May 2002 vol. 14 no. 5 1077-1092

What is claimed is:

1. A method for producing a human polypeptide-of-interest with a modified glycosylation pattern, the method comprising introducing into a plant or plant cell:
   a nucleic acid sequence encoding the human polypeptide-of-interest translationally fused to a signal peptide for localization in a subcellular compartment;
   one or more agents for suppressing expression of a fucosyltransferase and a xylosyltransferase;
   at least one polypeptide which confers an agricultural effective trait; and
   a nucleic acid sequence encoding an affinity moiety translationally fused to a cell wall binding peptide or a signal peptide for localization in the subcellular compartment,
   wherein the affinity moiety is for binding the human polypeptide of interest, and wherein the subcellular compartment is the apoplast or the endoplasmic reticulum.

2. The method of claim 1, wherein the one or more agents comprise one or more CRISPR-Cas9 gene editors.

3. The method of claim 1, wherein the xylosyltransferase comprises beta-(1,2)-xylosyltransferase, and wherein the one or more agents comprise a CRISPR-Cas9 gene editor capable of inactivating beta-(1,2)-xylosyltransferase.

4. The method of claim 1, wherein the fucosyltransferase comprises Alpha-(1, 3)-fucosyltransferase, and wherein the one or more agents comprise a CRISPR-Cas9 gene editor for inactivating Alpha-(1, 3)-fucosyltransferase.

5. The method of claim 1, wherein the one or more agents further comprise a CRISPR-Cas9 gene editor for inactivating GDP-D-mannose 4,6-dehydratase.

6. The method of claim 1, further comprising introducing into the plant or plant cell a nucleic acid sequence encoding at least one glycosidase.

7. The method of claim 1, wherein said polypeptide-of interest is an antibody or an antibody fragment.

8. A plant or plant cell characterized by:
   (i) the plant expressing a nucleic acid sequence encoding a human polypeptide of interest translationally fused to a signal peptide for localization in a subcellular compartment;
   (ii) the plant having reduced endogenous levels of a fucosyltransferase and a xylosyltransferase;
   (iii) the plant expressing a nucleic acid sequence encoding an affinity moiety translationally fused to a cell wall binding peptide or to a signal peptide for localization in the subcellular compartment, wherein the affinity moiety is for binding the human polypeptide of interest; and
   (iv) the plant expressing at least one nucleic acid sequence encoding a polypeptide which confers an agricultural effective trait;
   wherein the subcellular compartment is the apoplast or the endoplasmic reticulum.

9. The plant of claim 8, wherein the reduced endogenous level of the fucosyltransferase and the xylosyltransferase is effected by CRISPR/Cas9.

10. The plant of claim 8, wherein the xylosyltransferase is beta-(1,2)-xylosyltransferase.

11. The plant of claim 8, wherein the fucosyltransferase is Alpha-(1,3)-fucosyltransferase.

12. The plant of claim 8, further comprising a reduced level of GDP-D-mannose 4,6-dehydratase.

13. The plant of claim 8, wherein the plant or plant cell is further modified to express a nucleic acid sequence encoding at least one glycosidase.

14. The plant of claim 8, wherein said polypeptide-of interest is an antibody or an antibody fragment.

15. The plant of claim 8, wherein the agricultural effective trait is improved insect resistance, disease resistance, herbicide resistance, increased yield, increased tolerance to environmental stress or any combination thereof, as compared to that of a wild-type plant of the same species.

16. The plant of claim 8, wherein the plant is of the species *N. tabacum*.

17. The plant of claim 8, wherein the cell wall binding peptide is a Transmembrane Domain (TMD) or a Cellulose Binding Domain (CBD).

18. The plant of claim 8, wherein the affinity moiety is Protein A, Protein G or Protein L.

19. The plant of claim 8, wherein the binding of the affinity moiety to the human polypeptide of interest is releasable by pH change.

* * * * *